United States Patent
Conseiller et al.

(10) Patent No.: US 6,933,373 B2
(45) Date of Patent: Aug. 23, 2005

(54) P53 PROTEIN VARIANTS AND THERAPEUTIC USES THEREOF

(75) Inventors: Emmanuel Conseiller, Paris (FR); Laurent Bracco, Paris (FR)

(73) Assignee: Aventis Pharma S.A., Antony (FR)

( * ) Notice: Subject to any disclaimer, the term of this patent is extended or adjusted under 35 U.S.C. 154(b) by 136 days.

(21) Appl. No.: 09/968,851

(22) Filed: Oct. 3, 2001

(65) Prior Publication Data

US 2002/0193561 A1 Dec. 19, 2002

Related U.S. Application Data

(62) Division of application No. 08/983,035, filed as application No. PCT/FR96/01111 on Jul. 17, 1996, now Pat. No. 6,326,464.

(30) Foreign Application Priority Data

Jul. 19, 1995 (FR) .......................................... 95 08729

(51) Int. Cl.$^7$ .................. C07H 21/04; C12N 15/74
(52) U.S. Cl. .................. 536/23.1; 435/320.1
(58) Field of Search ....................... 536/23.1; 435/320.1

(56) References Cited

U.S. PATENT DOCUMENTS 5,573,925 A    11/1996   Halazonetis ................ 435/69.7

FOREIGN PATENT DOCUMENTS

| WO | WO 94/12202 A1 | 6/1994 | .......... A61K/37/02 |
| WO | WO 95/09916 A1 | 4/1995 | ........... C12N/15/11 |
| WO | WO 95/16771 A1 | 6/1995 | ............ C12N/5/10 |
| WO | WO 95/17213 A1 | 6/1995 | .......... A61K/48/00 |
| WO | WO 96/16989 A1 | 6/1996 | ........... C07K/14/82 |

OTHER PUBLICATIONS

Bowiet et al (Science, 1990, 257:1306–1310).*
Burgess et al (J. Cell Bio., 1990, 111:2129–2138).*
Lazar et al (Mol. Cell. Biol., 1988, 8:1247–1252).*
Orkin et al(REport and Recommendatson of the Panel to Assess the NIH investment in Research on GEne Therapy, 1995).*
Marshall (Science, 1995, 269:1050–1055).*
Culver et al (TTIG, 1994, 1:174–1780).*
Sun et al (J. Clin. Invest., 1995, 96:1535–1547).*
Hodgson (Exp. Opin. THer. Patents, 1995, 5:459–468).*
Miller et al (FASEB J., 1995, 9:190–199).*
Nature Biotechnology, 19976, 15:815).*
Gura (Science 1997, 278:1041–1042).*
Jain (Sci. Am., 1994, 271:58–65).*
Curti (Crit. Rev. in Oncology/Hematology, 1993, 14:29–39).*
Reed et al. "p53 domains: suppression, transformation, and transactivation" *Gene Expression* 3(1):95–107 (1993).
Pietenpol et al. "Sequence–specific transcriptional activation is essential for growth suppression by p53" *Proc. Natl. Acad. Sci. USA* 91:1998–2002 (1994).
Brown et al. "The Tumor Suppressor p53 and the Oncoprotein Simian Virus 40 T Antigen Bind to Overlapping Domains on the MDM2 Protein" *Molecular & Cellular Biology* 13(11):6849–6857 (1993).
Wu et al. "Alternatively Spliced Forms in the Carboxy–Terminal Domain of the p53 Protein Regulate Its Ability to Promote Annealing of Complementary Single Strands of Nucleic Acids" *Molecular & Cellular Biology* 15(1): 497–504 (1995).
Attardi et al. "Transcriptional activation by p53, but not induction of the p21 gene, is essential for oncogene–mediated apoptosis" *The EMBO Journal* 15(14): 3693–3701 (1996).
Hu et al. "Sequence Requirements for Coiled–Coils: Analysis with λ Repressor–GCN4 Leucine Zipper Fusions" *Science* 250: 1400–1403 (1990).

* cited by examiner

*Primary Examiner*—Susan Ungar
(74) *Attorney, Agent, or Firm*—Finnegan, Henderson, Farabow, Garrett & Dunner

(57) ABSTRACT

Proteins derived from the product of tumor suppressor gene p53 and having enhanced functions for therapeutical use are disclosed. The proteins advantageously have enhanced tumour suppressor and programmed cell death inducer functions, particularly in proliferative disease contexts where wild-type p53 protein is inactivated. Nucleic acids coding for such molecules, vectors containing same, and therapeutical use thereof, particularly in gene therapy, are also disclosed.

12 Claims, 18 Drawing Sheets

A: WILD-TYPE p53 / B: V-325 / C: V-336 / *: +E6

US 6,933,373 B2

SEQUENCE LISTING (1) GENERAL INFORMATION:

(iii) NUMBER OF SEQUENCES: 59

(2) INFORMATION FOR SEQ ID NO: 1:

(i) SEQUENCE CHARACTERISTICS:
      (A) LENGTH: 112 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
AGATCTGAAG GCCCTCAAGG AGAAGCTGAA GGCCCTGGAG GAGAAGCTGA AGGCCCTGGA      60

GGAGAAGCTG AAGGCACTAG TGGGGGAGCG ATGATGAATC GATATCGCGG CC             112
```

(2) INFORMATION FOR SEQ ID NO: 2:

(i) SEQUENCE CHARACTERISTICS:
      (A) LENGTH: 266 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

```
AAGCTTGAAT TCGTTAACAT GTCCACGGCC CCCCCGACCG ATGTCAGCCT GGGGGACGAG      60

CTCCACTTAG ACGGCGAGGA CGTGGCGATG GCGCATGCCG ACGCGCTAGA CGATTTCGAT     120

CTGGACATGT TGGGGGACGG GGATTCCCCG GGGCCGGGAT TTACCCCCCA CGACTCCGCC     180

CCCTACGGCG CTCTGGATAT GGCCGACTTC GAGTTTGAGC AGATGTTTAC CGATGCCCTT     240

GGAATTGACG AGTACGGTGG TCGACC                                          266
```

(2) INFORMATION FOR SEQ ID NO: 3:

(i) SEQUENCE CHARACTERISTICS:
      (A) LENGTH: 76 base pairs
      (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO: 3:

TCGAGCCTGC AGCCTAGAGC CTTCCAAGCC CTCATGAAGG AGGAAAGCCC AAACTGCTAG        60

TGAGGATCCG CGGCCG                                                        76

(2) INFORMATION FOR SEQ ID NO: 4:

(i) SEQUENCE CHARACTERISTICS:
        (A) LENGTH: 788 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

GGGAAGCTTG GGCCGGGTCG ACCTGCACCA GCAGCTCCTA CACCGGCGGC CCCTGCACCA        60

GCCCCCTCCT GGCCCCTGTC ATCTTCTGTC CCTTCCCAGA AAACCTACCA GGGCAGCTAC       120

GGTTTCCGTC TGGGCTTCTT GCATTCTGGG ACAGCCAAGT CTGTGACTTG CACGTACTCC       180

CCTGCCCTCA ACAAGATGTT TTGCCAACTG GCCAAGACCT GCCCTGTGCA GCTGTGGGTT       240

GATTCCACAC CCCCGCCCGG CACCCGCGTC CGCGCCATGG CCATCTACAA GCAGTCACAG       300

CACATGACGG AGGTTGTGAG GCGCTGCCCC CACCATGAGC GCTGCTCAGA TAGCGATGGT       360

CTGGCCCCTC CTCAGCATCT TATCCGAGTG GAAGGAAATT TGCGTGTGGA GTATTTGGAT       420

GACAGAAACA CTTTTCGACA TAGTGTGGTG GTGCCCTATG AGCCGCCTGA GGTTGGCTCT       480

GACTGTACCA CCATCCACTA CAACTACATG TGTAACAGTT CCTGCATGGG CGGCATGAAC       540

CGGAGGCCCA TCCTCACCAT CATCACACTG GAAGACTCCA GTGGTAATCT ACTGGGACGG       600

AACAGCTTTG AGGTGCGTGT TTGTGCCTGT CCTGGGAGAG ACCGGCGCAC AGAGGAAGAG       660

AATCTCCGCA AGAAAGGGGA GCCTCACCAC GAGCTGCCCC CAGGGAGCAC TAAGCGAGCA       720

CTGCCCAACA ACACCAGCTC CTCTCCCCAG CCAAAGAAGA AACCACTGGA TGGGGATCCG       780

CGGCCGCC                                                                788

(2) INFORMATION FOR SEQ ID NO: 5:

(i) SEQUENCE CHARACTERISTICS:
        (A) LENGTH: 821 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

GGGAAGCTTG GGCCGGGTCG ACCTGCACCA GCAGCTCCTA CACCGGCGGC CCCTGCACCA        60

GCCCCCTCCT GGCCCCTGTC ATCTTCTGTC CCTTCCCAGA AAACCTACCA GGGCAGCTAC       120

GGTTTCCGTC TGGGCTTCTT GCATTCTGGG ACAGCCAAGT CTGTGACTTG CACGTACTCC       180

CCTGCCCTCA ACAAGATGTT TTGCCAACTG GCCAAGACCT GCCCTGTGCA GCTGTGGGTT       240

GATTCCACAC CCCCGCCCGG CACCCGCGTC CGCGCCATGG CCATCTACAA GCAGTCACAG       300

CACATGACGG AGGTTGTGAG GCGCTGCCCC CACCATGAGC GCTGCTCAGA TAGCGATGGT       360

CTGGCCCCTC CTCAGCATCT TATCCGAGTG GAAGGAAATT TGCGTGTGGA GTATTTGGAT       420
```

```
GACAGAAACA CTTTTCGACA TAGTGTGGTG GTGCCCTATG AGCCGCCTGA GGTTGGCTCT      480

GACTGTACCA CCATCCACTA CAACTACATG TGTAACAGTT CCTGCATGGG CGGCATGAAC      540

CGGAGGCCCA TCCTCACCAT CATCACACTG GAAGACTCCA GTGGTAATCT ACTGGGACGG      600

AACAGCTTTG AGGTGCGTGT TTGTGCCTGT CCTGGGAGAG ACCGGCGCAC AGAGGAAGAG      660

AATCTCCGCA AGAAAGGGGA GCCTCACCAC GAGCTGCCCC CAGGGAGCAC TAAGCGAGCA      720

CTGCCCAACA ACACCAGCTC CTCTCCCCAG CCAAAGAAGA AACCACTGGA TGGAGAATAT      780

TTCACCCTTC AGATCCGTGG GCGTGAGGAT CCGCGGCCGC C                          821

(2) INFORMATION FOR SEQ ID NO: 6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 6:

ATGGAGGAGC CGCAG                                                        15

(2) INFORMATION FOR SEQ ID NO: 7:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 7:

GGCGGCCGCG ATATCGATTC ATCAGTCTGA GTCAGGCCCT TC                          42

(2) INFORMATION FOR SEQ ID NO: 8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 8:

GGCGGCCGCG ATATCGATTC ATCAGCTCGA GTGAGC                                 36

(2) INFORMATION FOR SEQ ID NO: 9:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 9:

TCGAGCCTGC AGCCTAGAGC CTTCCAAGCC CTCATGAAGG AGG                         43
```

(2) INFORMATION FOR SEQ ID NO: 10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 10:

AAAGCCCAAA CTGCTGATGA ATCGATATCG C                      31

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 11:

TGAGGGCTTG GAAGGCTCTA GGCTGCAGGC                       30

(2) INFORMATION FOR SEQ ID NO: 12:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 12:

GGCCGCGATA TCGATTCATC AGCAGTTTGG GCTTTCCTCC TTCA           44

(2) INFORMATION FOR SEQ ID NO: 13:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 13:

GGGAAGCTTG GGCCGGGTCG ACCTGCACCA GCAGCTCCT               39

(2) INFORMATION FOR SEQ ID NO: 14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 14:

GGCGGCCGCG GATCCCCATC CAGTGGTTTC TT                     32

(2) INFORMATION FOR SEQ ID NO: 15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 15:

ATCTGAATGG CGCTC                                                   15

(2) INFORMATION FOR SEQ ID NO: 16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 16:

GGCGGCCGCG GATCCTCACG CCCACGGATC TG                       32

(2) INFORMATION FOR SEQ ID NO: 17:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 17:

AAGCTTGAAT TCGTTAACAT GTCCACGGCC CCCCCGACC              39

(2) INFORMATION FOR SEQ ID NO: 18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 18:

GGTCGACCAC CGTACTCGTC AAT                                  23

(2) INFORMATION FOR SEQ ID NO: 19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 19:

GATCTGAAGG CCCTCAAGGA GAAGCTGAAG GCC                    33

(2) INFORMATION FOR SEQ ID NO: 20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 20:

CTGGAGGAGA AGCTGAAGGC CCTGGAGGAG AAGCTG                              36

(2) INFORMATION FOR SEQ ID NO: 21:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 21:

AAGGCACTAG TGGGGGAGCG ATGATGAATC GATATCGC                            38

(2) INFORMATION FOR SEQ ID NO: 22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 22:

AAGGCACTAG TGGGGGAGCG ATGATGAATC GATATCGC                            38

(2) INFORMATION FOR SEQ ID NO: 23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 23:

TAGTGCCTTC AGCTTCTCCT CCAGGGCCTT CAGCTT                              36

(2) INFORMATION FOR SEQ ID NO: 24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 24:

```
GGCCGCGATA TCGATTCATC ATCGCTCCCC CAC                                  33
```

(2) INFORMATION FOR SEQ ID NO: 25:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1089

(xi) SEQUENCE DESCRIPTION: SEQ ID NO: 25:

```
ATG TCC ACG GCC CCC CCG ACC GAT GTC AGC CTG GGG GAC GAG CTC CAC       48
Met Ser Thr Ala Pro Pro Thr Asp Val Ser Leu Gly Asp Glu Leu His
 1               5                  10                  15

TTA GAC GGC GAG GAC GTG GCG ATG GCG CAT GCC GAC GCG CTA GAC GAT       96
Leu Asp Gly Glu Asp Val Ala Met Ala His Ala Asp Ala Leu Asp Asp
                 20                  25                  30

TTC GAT CTG GAC ATG TTG GGG GAC GGG GAT TCC CCG GGG CCG GGA TTT      144
Phe Asp Leu Asp Met Leu Gly Asp Gly Asp Ser Pro Gly Pro Gly Phe
             35                  40                  45

ACC CCC CAC GAC TCC GCC CCC TAC GGC GCT CTG GAT ATG GCC GAC TTC      192
Thr Pro His Asp Ser Ala Pro Tyr Gly Ala Leu Asp Met Ala Asp Phe
         50                  55                  60

GAG TTT GAG CAG ATG TTT ACC GAT GCC CTT GGA ATT GAC GAG TAC GGT      240
Glu Phe Glu Gln Met Phe Thr Asp Ala Leu Gly Ile Asp Glu Tyr Gly
 65                  70                  75                  80

GGT CGA CCT GCA CCA GCA GCT CCT ACA CCG GCG GCC CCT GCA CCA GCC      288
Gly Arg Pro Ala Pro Ala Ala Pro Thr Pro Ala Ala Pro Ala Pro Ala
                 85                  90                  95

CCC TCC TGG CCC CTG TCA TCT TCT GTC CCT TCC CAG AAA ACC TAC CAG      336
Pro Ser Trp Pro Leu Ser Ser Ser Val Pro Ser Gln Lys Thr Tyr Gln
            100                 105                 110

GGC AGC TAC GGT TTC CGT CTG GGC TTC TTG CAT TCT GGG ACA GCC AAG      384
Gly Ser Tyr Gly Phe Arg Leu Gly Phe Leu His Ser Gly Thr Ala Lys
        115                 120                 125

TCT GTG ACT TGC ACG TAC TCC CCT GCC CTC AAC AAG ATG TTT TGC CAA      432
Ser Val Thr Cys Thr Tyr Ser Pro Ala Leu Asn Lys Met Phe Cys Gln
    130                 135                 140

CTG GCC AAG ACC TGC CCT GTG CAG CTG TGG GTT GAT TCC ACA CCC CCG      480
Leu Ala Lys Thr Cys Pro Val Gln Leu Trp Val Asp Ser Thr Pro Pro
145                 150                 155                 160

CCC GGC ACC CGC GTC CGC GCC ATG GCC ATC TAC AAG CAG TCA CAG CAC      528
Pro Gly Thr Arg Val Arg Ala Met Ala Ile Tyr Lys Gln Ser Gln His
                165                 170                 175

ATG ACG GAG GTT GTG AGG CGC TGC CCC CAC CAT GAG CGC TGC TCA GAT      576
Met Thr Glu Val Val Arg Arg Cys Pro His His Glu Arg Cys Ser Asp
            180                 185                 190

AGC GAT GGT CTG GCC CCT CCT CAG CAT CTT ATC CGA GTG GAA GGA AAT      624
Ser Asp Gly Leu Ala Pro Pro Gln His Leu Ile Arg Val Glu Gly Asn
        195                 200                 205

TTG CGT GTG GAG TAT TTG GAT GAC AGA AAC ACT TTT CGA CAT AGT GTG      672
Leu Arg Val Glu Tyr Leu Asp Asp Arg Asn Thr Phe Arg His Ser Val
    210                 215                 220

GTG GTG CCC TAT GAG CCG CCT GAG GTT GGC TCT GAC TGT ACC ACC ATC      720
Val Val Pro Tyr Glu Pro Pro Glu Val Gly Ser Asp Cys Thr Thr Ile
225                 230                 235                 240
```

```
CAC TAC AAC TAC ATG TGT AAC AGT TCC TGC ATG GGC GGC ATG AAC CGG      768
His Tyr Asn Tyr Met Cys Asn Ser Ser Cys Met Gly Gly Met Asn Arg
            245                 250                 255

AGG CCC ATC CTC ACC ATC ATC ACA CTG GAA GAC TCC AGT GGT AAT CTA      816
Arg Pro Ile Leu Thr Ile Ile Thr Leu Glu Asp Ser Ser Gly Asn Leu
                260                 265                 270

CTG GGA CGG AAC AGC TTT GAG GTG CGT GTT TGT GCC TGT CCT GGG AGA      864
Leu Gly Arg Asn Ser Phe Glu Val Arg Val Cys Ala Cys Pro Gly Arg
                275                 280                 285

GAC CGG CGC ACA GAG GAA GAG AAT CTC CGC AAG AAA GGG GAG CCT CAC      912
Asp Arg Arg Thr Glu Glu Glu Asn Leu Arg Lys Lys Gly Glu Pro His
            290                 295                 300

CAC GAG CTG CCC CCA GGG AGC ACT AAG CGA GCA CTG CCC AAC AAC ACC      960
His Glu Leu Pro Pro Gly Ser Thr Lys Arg Ala Leu Pro Asn Asn Thr
305                 310                 315                 320

AGC TCC TCT CCC CAG CCA AAG AAG AAA CCA CTG GAT GGG GAT CTG AAG     1008
Ser Ser Ser Pro Gln Pro Lys Lys Lys Pro Leu Asp Gly Asp Leu Lys
                325                 330                 335

GCC CTC AAG GAG AAG CTG AAG GCC CTG GAG GAG AAG CTG AAG GCC CTG     1056
Ala Leu Lys Glu Lys Leu Lys Ala Leu Glu Glu Lys Leu Lys Ala Leu
                340                 345                 350

GAG GAG AAG CTG AAG GCA CTA GTG GGG GAG CGA TGATGA                  1095
Glu Glu Lys Leu Lys Ala Leu Val Gly Glu Arg
            355                 360

(2) INFORMATION FOR SEQ ID NO: 26:

(i) SEQUENCE CHARACTERISTICS:
        (A) LENGTH: 363 amino acids
        (B) TYPE: amino acid
        (D) TOPOLOGY: linear (ii) MOLECULE TYPE: protein (xi) SEQUENCE DESCRIPTION: SEQ ID NO: 26:

Met Ser Thr Ala Pro Pro Thr Asp Val Ser Leu Gly Asp Glu Leu His
  1               5                  10                  15

Leu Asp Gly Glu Asp Val Ala Met Ala His Ala Asp Ala Leu Asp Asp
                 20                  25                  30

Phe Asp Leu Asp Met Leu Gly Asp Gly Asp Ser Pro Gly Pro Gly Phe
             35                  40                  45

Thr Pro His Asp Ser Ala Pro Tyr Gly Ala Leu Asp Met Ala Asp Phe
         50                  55                  60

Glu Phe Glu Gln Met Phe Thr Asp Ala Leu Gly Ile Asp Glu Tyr Gly
 65                  70                  75                  80

Gly Arg Pro Ala Pro Ala Ala Pro Thr Pro Ala Ala Pro Ala Pro Ala
                 85                  90                  95

Pro Ser Trp Pro Leu Ser Ser Val Pro Ser Gln Lys Thr Tyr Gln
                100                 105                 110

Gly Ser Tyr Gly Phe Arg Leu Gly Phe Leu His Ser Gly Thr Ala Lys
             115                 120                 125

Ser Val Thr Cys Thr Tyr Ser Pro Ala Leu Asn Lys Met Phe Cys Gln
130                 135                 140

Leu Ala Lys Thr Cys Pro Val Gln Leu Trp Val Asp Ser Thr Pro Pro
145                 150                 155                 160

Pro Gly Thr Arg Val Arg Ala Met Ala Ile Tyr Lys Gln Ser Gln His
                165                 170                 175

Met Thr Glu Val Val Arg Arg Cys Pro His His Glu Arg Cys Ser Asp
             180                 185                 190
```

```
Ser Asp Gly Leu Ala Pro Pro Gln His Leu Ile Arg Val Glu Gly Asn
        195                 200                 205

Leu Arg Val Glu Tyr Leu Asp Asp Arg Asn Thr Phe Arg His Ser Val
    210                 215                 220

Val Val Pro Tyr Glu Pro Pro Glu Val Gly Ser Asp Cys Thr Thr Ile
225                 230                 235                 240

His Tyr Asn Tyr Met Cys Asn Ser Ser Cys Met Gly Gly Met Asn Arg
                245                 250                 255

Arg Pro Ile Leu Thr Ile Ile Thr Leu Glu Asp Ser Ser Gly Asn Leu
            260                 265                 270

Leu Gly Arg Asn Ser Phe Glu Val Arg Val Cys Ala Cys Pro Gly Arg
        275                 280                 285

Asp Arg Arg Thr Glu Glu Glu Asn Leu Arg Lys Lys Gly Glu Pro His
    290                 295                 300

His Glu Leu Pro Pro Gly Ser Thr Lys Arg Ala Leu Pro Asn Asn Thr
305                 310                 315                 320

Ser Ser Ser Pro Gln Pro Lys Lys Lys Pro Leu Asp Gly Asp Leu Lys
                325                 330                 335

Ala Leu Lys Glu Lys Leu Lys Ala Leu Glu Glu Lys Leu Lys Ala Leu
            340                 345                 350

Glu Glu Lys Leu Lys Ala Leu Val Gly Glu Arg
        355                 360

(2) INFORMATION FOR SEQ ID NO: 27:

(i) SEQUENCE CHARACTERISTICS:
        (A) LENGTH: 1128 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1122

(xi) SEQUENCE DESCRIPTION: SEQ ID NO: 27:

ATG TCC ACG GCC CCC CCG ACC GAT GTC AGC CTG GGG GAC GAG CTC CAC      48
Met Ser Thr Ala Pro Pro Thr Asp Val Ser Leu Gly Asp Glu Leu His
 1               5                  10                  15

TTA GAC GGC GAG GAC GTG GCG ATG GCG CAT GCC GAC GCG CTA GAC GAT      96
Leu Asp Gly Glu Asp Val Ala Met Ala His Ala Asp Ala Leu Asp Asp
                20                  25                  30

TTC GAT CTG GAC ATG TTG GGG GAC GGG GAT TCC CCG GGG CCG GGA TTT     144
Phe Asp Leu Asp Met Leu Gly Asp Gly Asp Ser Pro Gly Pro Gly Phe
            35                  40                  45

ACC CCC CAC GAC TCC GCC CCC TAC GGC GCT CTG GAT ATG GCC GAC TTC     192
Thr Pro His Asp Ser Ala Pro Tyr Gly Ala Leu Asp Met Ala Asp Phe
        50                  55                  60

GAG TTT GAG CAG ATG TTT ACC GAT GCC CTT GGA ATT GAC GAG TAC GGT     240
Glu Phe Glu Gln Met Phe Thr Asp Ala Leu Gly Ile Asp Glu Tyr Gly
65                  70                  75                  80

GGT CGA CCT GCA CCA GCA GCT CCT ACA CCG GCG GCC CCT GCA CCA GCC     288
Gly Arg Pro Ala Pro Ala Ala Pro Thr Pro Ala Ala Pro Ala Pro Ala
                85                  90                  95

CCC TCC TGG CCC CTG TCA TCT TCT GTC CCT TCC CAG AAA ACC TAC CAG     336
Pro Ser Trp Pro Leu Ser Ser Ser Val Pro Ser Gln Lys Thr Tyr Gln
            100                 105                 110
```

| | | | | | | | | | | | | | | | |
|---|---|---|---|---|---|---|---|---|---|---|---|---|---|---|---|
|GGC|AGC|TAC|GGT|TTC|CGT|CTG|GGC|TTC|TTG|CAT|TCT|GGG|ACA|GCC|AAG| 384
|Gly|Ser|Tyr|Gly|Phe|Arg|Leu|Gly|Phe|Leu|His|Ser|Gly|Thr|Ala|Lys|
| |115| | | | |120| | | | |125| | | | |

| | | | | | | | | | | | | | | | |
|---|---|---|---|---|---|---|---|---|---|---|---|---|---|---|---|
|TCT|GTG|ACT|TGC|ACG|TAC|TCC|CCT|GCC|CTC|AAC|AAG|ATG|TTT|TGC|CAA| 432
|Ser|Val|Thr|Cys|Thr|Tyr|Ser|Pro|Ala|Leu|Asn|Lys|Met|Phe|Cys|Gln|
| |130| | | | |135| | | | |140| | | | |

| | | | | | | | | | | | | | | | |
|---|---|---|---|---|---|---|---|---|---|---|---|---|---|---|---|
|CTG|GCC|AAG|ACC|TGC|CCT|GTG|CAG|CTG|TGG|GTT|GAT|TCC|ACA|CCC|CCG| 480
|Leu|Ala|Lys|Thr|Cys|Pro|Val|Gln|Leu|Trp|Val|Asp|Ser|Thr|Pro|Pro|
|145| | | | |150| | | | |155| | | | |160|

| | | | | | | | | | | | | | | | |
|---|---|---|---|---|---|---|---|---|---|---|---|---|---|---|---|
|CCC|GGC|ACC|CGC|GTC|CGC|GCC|ATG|GCC|ATC|TAC|AAG|CAG|TCA|CAG|CAC| 528
|Pro|Gly|Thr|Arg|Val|Arg|Ala|Met|Ala|Ile|Tyr|Lys|Gln|Ser|Gln|His|
| | | |165| | | | |170| | | | |175| | |

| | | | | | | | | | | | | | | | |
|---|---|---|---|---|---|---|---|---|---|---|---|---|---|---|---|
|ATG|ACG|GAG|GTT|GTG|AGG|CGC|TGC|CCC|CAC|CAT|GAG|CGC|TGC|TCA|GAT| 576
|Met|Thr|Glu|Val|Val|Arg|Arg|Cys|Pro|His|His|Glu|Arg|Cys|Ser|Asp|
| | | |180| | | | |185| | | | |190| | |

| | | | | | | | | | | | | | | | |
|---|---|---|---|---|---|---|---|---|---|---|---|---|---|---|---|
|AGC|GAT|GGT|CTG|GCC|CCT|CCT|CAG|CAT|CTT|ATC|CGA|GTG|GAA|GGA|AAT| 624
|Ser|Asp|Gly|Leu|Ala|Pro|Pro|Gln|His|Leu|Ile|Arg|Val|Glu|Gly|Asn|
| | | |195| | | | |200| | | | |205| | |

| | | | | | | | | | | | | | | | |
|---|---|---|---|---|---|---|---|---|---|---|---|---|---|---|---|
|TTG|CGT|GTG|GAG|TAT|TTG|GAT|GAC|AGA|AAC|ACT|TTT|CGA|CAT|AGT|GTG| 672
|Leu|Arg|Val|Glu|Tyr|Leu|Asp|Asp|Arg|Asn|Thr|Phe|Arg|His|Ser|Val|
| |210| | | | |215| | | | |220| | | | |

| | | | | | | | | | | | | | | | |
|---|---|---|---|---|---|---|---|---|---|---|---|---|---|---|---|
|GTG|GTG|CCC|TAT|GAG|CCG|CCT|GAG|GTT|GGC|TCT|GAC|TGT|ACC|ACC|ATC| 720
|Val|Val|Pro|Tyr|Glu|Pro|Pro|Glu|Val|Gly|Ser|Asp|Cys|Thr|Thr|Ile|
|225| | | | |230| | | | |235| | | | |240|

| | | | | | | | | | | | | | | | |
|---|---|---|---|---|---|---|---|---|---|---|---|---|---|---|---|
|CAC|TAC|AAC|TAC|ATG|TGT|AAC|AGT|TCC|TGC|ATG|GGC|GGC|ATG|AAC|CGG| 768
|His|Tyr|Asn|Tyr|Met|Cys|Asn|Ser|Ser|Cys|Met|Gly|Gly|Met|Asn|Arg|
| | | |245| | | | |250| | | | |255| | |

| | | | | | | | | | | | | | | | |
|---|---|---|---|---|---|---|---|---|---|---|---|---|---|---|---|
|AGG|CCC|ATC|CTC|ACC|ATC|ATC|ACA|CTG|GAA|GAC|TCC|AGT|GGT|AAT|CTA| 816
|Arg|Pro|Ile|Leu|Thr|Ile|Ile|Thr|Leu|Glu|Asp|Ser|Ser|Gly|Asn|Leu|
| | | |260| | | | |265| | | | |270| | |

| | | | | | | | | | | | | | | | |
|---|---|---|---|---|---|---|---|---|---|---|---|---|---|---|---|
|CTG|GGA|CGG|AAC|AGC|TTT|GAG|GTG|CGT|GTT|TGT|GCC|TGT|CCT|GGG|AGA| 864
|Leu|Gly|Arg|Asn|Ser|Phe|Glu|Val|Arg|Val|Cys|Ala|Cys|Pro|Gly|Arg|
| | | |275| | | | |280| | | | |285| | |

| | | | | | | | | | | | | | | | |
|---|---|---|---|---|---|---|---|---|---|---|---|---|---|---|---|
|GAC|CGG|CGC|ACA|GAG|GAA|GAG|AAT|CTC|CGC|AAG|AAA|GGG|GAG|CCT|CAC| 912
|Asp|Arg|Arg|Thr|Glu|Glu|Glu|Asn|Leu|Arg|Lys|Lys|Gly|Glu|Pro|His|
| |290| | | | |295| | | | |300| | | | |

| | | | | | | | | | | | | | | | |
|---|---|---|---|---|---|---|---|---|---|---|---|---|---|---|---|
|CAC|GAG|CTG|CCC|CCA|GGG|AGC|ACT|AAG|CGA|GCA|CTG|CCC|AAC|AAC|ACC| 960
|His|Glu|Leu|Pro|Pro|Gly|Ser|Thr|Lys|Arg|Ala|Leu|Pro|Asn|Asn|Thr|
|305| | | | |310| | | | |315| | | | |320|

| | | | | | | | | | | | | | | | |
|---|---|---|---|---|---|---|---|---|---|---|---|---|---|---|---|
|AGC|TCC|TCT|CCC|CAG|CCA|AAG|AAG|AAA|CCA|CTG|GAT|GGA|GAA|TAT|TTC| 1008
|Ser|Ser|Ser|Pro|Gln|Pro|Lys|Lys|Lys|Pro|Leu|Asp|Gly|Glu|Tyr|Phe|
| | | |325| | | | |330| | | | |335| | |

| | | | | | | | | | | | | | | | |
|---|---|---|---|---|---|---|---|---|---|---|---|---|---|---|---|
|ACC|CTT|CAG|ATC|CGT|GGG|CGT|GAG|GAT|CTG|AAG|GCC|CTC|AAG|GAG|AAG| 1056
|Thr|Leu|Gln|Ile|Arg|Gly|Arg|Glu|Asp|Leu|Lys|Ala|Leu|Lys|Glu|Lys|
| | | |340| | | | |345| | | | |350| | |

| | | | | | | | | | | | | | | | |
|---|---|---|---|---|---|---|---|---|---|---|---|---|---|---|---|
|CTG|AAG|GCC|CTG|GAG|GAG|AAG|CTG|AAG|GCC|CTG|GAG|GAG|AAG|CTG|AAG| 1104
|Leu|Lys|Ala|Leu|Glu|Glu|Lys|Leu|Lys|Ala|Leu|Glu|Glu|Lys|Leu|Lys|
| |355| | | | |360| | | | |365| | | | |

| | | | | |
|---|---|---|---|---|
|GCA|CTA|GTG|GGG|GAG|CGA|TGATGA| 1128
|Ala|Leu|Val|Gly|Glu|Arg|
| |370| | | | |

(2) INFORMATION FOR SEQ ID NO: 28:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO: 28:

```
Met Ser Thr Ala Pro Pro Thr Asp Val Ser Leu Gly Asp Glu Leu His
  1               5                  10                  15

Leu Asp Gly Glu Asp Val Ala Met Ala His Ala Asp Ala Leu Asp Asp
              20                  25                  30

Phe Asp Leu Asp Met Leu Gly Asp Gly Asp Ser Pro Gly Pro Gly Phe
          35                  40                  45

Thr Pro His Asp Ser Ala Pro Tyr Gly Ala Leu Asp Met Ala Asp Phe
      50                  55                  60

Glu Phe Glu Gln Met Phe Thr Asp Ala Leu Gly Ile Asp Glu Tyr Gly
 65                  70                  75                  80

Gly Arg Pro Ala Pro Ala Ala Pro Thr Pro Ala Ala Pro Ala Pro Ala
                 85                  90                  95

Pro Ser Trp Pro Leu Ser Ser Ser Val Pro Ser Gln Lys Thr Tyr Gln
                100                 105                 110

Gly Ser Tyr Gly Phe Arg Leu Gly Phe Leu His Ser Gly Thr Ala Lys
            115                 120                 125

Ser Val Thr Cys Thr Tyr Ser Pro Ala Leu Asn Lys Met Phe Cys Gln
        130                 135                 140

Leu Ala Lys Thr Cys Pro Val Gln Leu Trp Val Asp Ser Thr Pro Pro
145                 150                 155                 160

Pro Gly Thr Arg Val Arg Ala Met Ala Ile Tyr Lys Gln Ser Gln His
                165                 170                 175

Met Thr Glu Val Val Arg Arg Cys Pro His His Glu Arg Cys Ser Asp
                180                 185                 190

Ser Asp Gly Leu Ala Pro Pro Gln His Leu Ile Arg Val Glu Gly Asn
            195                 200                 205

Leu Arg Val Glu Tyr Leu Asp Asp Arg Asn Thr Phe Arg His Ser Val
        210                 215                 220

Val Val Pro Tyr Glu Pro Pro Glu Val Gly Ser Asp Cys Thr Thr Ile
225                 230                 235                 240

His Tyr Asn Tyr Met Cys Asn Ser Ser Cys Met Gly Gly Met Asn Arg
                245                 250                 255

Arg Pro Ile Leu Thr Ile Ile Thr Leu Glu Asp Ser Ser Gly Asn Leu
            260                 265                 270

Leu Gly Arg Asn Ser Phe Glu Val Arg Val Cys Ala Cys Pro Gly Arg
        275                 280                 285

Asp Arg Arg Thr Glu Glu Glu Asn Leu Arg Lys Lys Gly Glu Pro His
290                 295                 300

His Glu Leu Pro Pro Gly Ser Thr Lys Arg Ala Leu Pro Asn Asn Thr
305                 310                 315                 320

Ser Ser Ser Pro Gln Pro Lys Lys Lys Pro Leu Asp Gly Glu Tyr Phe
                325                 330                 335

Thr Leu Gln Ile Arg Gly Arg Glu Asp Leu Lys Ala Leu Lys Glu Lys
            340                 345                 350

Leu Lys Ala Leu Glu Glu Lys Leu Lys Ala Leu Glu Glu Lys Leu Lys
        355                 360                 365

Ala Leu Val Gly Glu Arg
        370

(2) INFORMATION FOR SEQ ID NO: 29:

(i) SEQUENCE CHARACTERISTICS:
        (A) LENGTH: 765 base pairs
        (B) TYPE: nucleic acid
```

-continued (C) STRANDEDNESS: single
        (D) TOPOLOGY: linear (ii) MOLECULE TYPE: cDNA (ix) FEATURE:
        (A) NAME/KEY: CDS
        (B) LOCATION: 1..759

(xi) SEQUENCE DESCRIPTION: SEQ ID NO: 29:

```
ATG TCC ACG GCC CCC CCG ACC GAT GTC AGC CTG GGG GAC GAG CTC CAC      48
Met Ser Thr Ala Pro Pro Thr Asp Val Ser Leu Gly Asp Glu Leu His
 1               5                  10                  15

TTA GAC GGC GAG GAC GTG GCG ATG GCG CAT GCC GAC GCG CTA GAC GAT      96
Leu Asp Gly Glu Asp Val Ala Met Ala His Ala Asp Ala Leu Asp Asp
                20                  25                  30

TTC GAT CTG GAC ATG TTG GGG GAC GGG GAT TCC CCG GGG CCG GGA TTT     144
Phe Asp Leu Asp Met Leu Gly Asp Gly Asp Ser Pro Gly Pro Gly Phe
         35                  40                  45

ACC CCC CAC GAC TCC GCC CCC TAC GGC GCT CTG GAT ATG GCC GAC TTC     192
Thr Pro His Asp Ser Ala Pro Tyr Gly Ala Leu Asp Met Ala Asp Phe
     50                  55                  60

GAG TTT GAG CAG ATG TTT ACC GAT GCC CTT GGA ATT GAC GAG TAC GGT     240
Glu Phe Glu Gln Met Phe Thr Asp Ala Leu Gly Ile Asp Glu Tyr Gly
 65                  70                  75                  80

GGT CGA CCT GCA CCA GCA GCT CCT ACA CCG GCG GCC CCT GCA CCA GCC     288
Gly Arg Pro Ala Pro Ala Ala Pro Thr Pro Ala Ala Pro Ala Pro Ala
                 85                  90                  95

CCC TCC TGG CCC CTG TCA TCT TCT GTC CCT TCC CAG AAA ACC TAC CAG     336
Pro Ser Trp Pro Leu Ser Ser Ser Val Pro Ser Gln Lys Thr Tyr Gln
            100                 105                 110

GGC AGC TAC GGT TTC CGT CTG GGC TTC TTG CAT TCT GGG ACA GCC AAG     384
Gly Ser Tyr Gly Phe Arg Leu Gly Phe Leu His Ser Gly Thr Ala Lys
        115                 120                 125

TCT GTG ACT TGC ACG TAC TCC CCT GCC CTC AAC AAG ATG TTT TGC CAA     432
Ser Val Thr Cys Thr Tyr Ser Pro Ala Leu Asn Lys Met Phe Cys Gln
    130                 135                 140

CTG GCC AAG ACC TGC CCT GTG CAG CTG TGG GTT GAT TCC ACA CCC CCG     480
Leu Ala Lys Thr Cys Pro Val Gln Leu Trp Val Asp Ser Thr Pro Pro
145                 150                 155                 160

CCC GGC ACC CGC GTC CGC GCC ATG GCC ATC TAC AAG CAG TCA CAG CAC     528
Pro Gly Thr Arg Val Arg Ala Met Ala Ile Tyr Lys Gln Ser Gln His
                165                 170                 175

ATG ACG GAG GTT GTG AGG CGC TGC CCC CAC CAT GAG CGC TGC TCA GAT     576
Met Thr Glu Val Val Arg Arg Cys Pro His His Glu Arg Cys Ser Asp
            180                 185                 190

AGC GAT GGT CTG GCC CCT CCT CAG CAT CTT ATC CGA GTG GAA GGA AAT     624
Ser Asp Gly Leu Ala Pro Pro Gln His Leu Ile Arg Val Glu Gly Asn
        195                 200                 205

TTG CGT GTG GAG TAT TTC ACC CTT CAG ATC CGT GGG CGT GAG CGC TTC     672
Leu Arg Val Glu Tyr Phe Thr Leu Gln Ile Arg Gly Arg Glu Arg Phe
    210                 215                 220

GAG ATG TTC CGA GAG CTG AAT GAG GCC TTG GAA CTC AAG GAT GCC CAG     720
Glu Met Phe Arg Glu Leu Asn Glu Ala Leu Glu Leu Lys Asp Ala Gln
225                 230                 235                 240

GCT GGG AAG GAG CCA GGG GGG AGC AGG GCT CAC TCG AGC TGATGA          765
Ala Gly Lys Glu Pro Gly Gly Ser Arg Ala His Ser Ser
                245                 250
```

(2) INFORMATION FOR SEQ ID NO: 30:

(i) SEQUENCE CHARACTERISTICS:

(A) LENGTH: 253 amino acids
        (B) TYPE: amino acid
        (D) TOPOLOGY: linear (ii) MOLECULE TYPE: protein (xi) SEQUENCE DESCRIPTION: SEQ ID NO: 30:

Met Ser Thr Ala Pro Pro Thr Asp Val Ser Leu Gly Asp Glu Leu His
1               5                   10                  15

Leu Asp Gly Glu Asp Val Ala Met Ala His Ala Asp Ala Leu Asp Asp
                20                  25                  30

Phe Asp Leu Asp Met Leu Gly Asp Gly Asp Ser Pro Gly Pro Gly Phe
            35                  40                  45

Thr Pro His Asp Ser Ala Pro Tyr Gly Ala Leu Asp Met Ala Asp Phe
        50                  55                  60

Glu Phe Glu Gln Met Phe Thr Asp Ala Leu Gly Ile Asp Glu Tyr Gly
65                  70                  75                  80

Gly Arg Pro Ala Pro Ala Ala Pro Thr Pro Ala Ala Pro Ala Pro Ala
                85                  90                  95

Pro Ser Trp Pro Leu Ser Ser Ser Val Pro Ser Gln Lys Thr Tyr Gln
                100                 105                 110

Gly Ser Tyr Gly Phe Arg Leu Gly Phe Leu His Ser Gly Thr Ala Lys
                115                 120                 125

Ser Val Thr Cys Thr Tyr Ser Pro Ala Leu Asn Lys Met Phe Cys Gln
            130                 135                 140

Leu Ala Lys Thr Cys Pro Val Gln Leu Trp Val Asp Ser Thr Pro Pro
145                 150                 155                 160

Pro Gly Thr Arg Val Arg Ala Met Ala Ile Tyr Lys Gln Ser Gln His
                165                 170                 175

Met Thr Glu Val Val Arg Arg Cys Pro His His Glu Arg Cys Ser Asp
            180                 185                 190

Ser Asp Gly Leu Ala Pro Pro Gln His Leu Ile Arg Val Glu Gly Asn
        195                 200                 205

Leu Arg Val Glu Tyr Phe Thr Leu Gln Ile Arg Gly Arg Glu Arg Phe
210                 215                 220

Glu Met Phe Arg Glu Leu Asn Glu Ala Leu Glu Leu Lys Asp Ala Gln
225                 230                 235                 240

Ala Gly Lys Glu Pro Gly Gly Ser Arg Ala His Ser Ser
                245                 250

(2) INFORMATION FOR SEQ ID NO: 31:

(i) SEQUENCE CHARACTERISTICS:
        (A) LENGTH: 816 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..810

(xi) SEQUENCE DESCRIPTION: SEQ ID NO: 31:

```
ATG TCC ACG GCC CCC CCG ACC GAT GTC AGC CTG GGG GAC GAG CTC CAC      48
Met Ser Thr Ala Pro Pro Thr Asp Val Ser Leu Gly Asp Glu Leu His
1               5                   10                  15

TTA GAC GGC GAG GAC GTG GCG ATG GCG CAT GCC GAC GCG CTA GAC GAT      96
Leu Asp Gly Glu Asp Val Ala Met Ala His Ala Asp Ala Leu Asp Asp
```

```
            20                  25                  30
TTC GAT CTG GAC ATG TTG GGG GAC GGG GAT TCC CCG GGG CCG GGA TTT       144
Phe Asp Leu Asp Met Leu Gly Asp Gly Asp Ser Pro Gly Pro Gly Phe
            35                  40                  45

ACC CCC CAC GAC TCC GCC CCC TAC GGC GCT CTG GAT ATG GCC GAC TTC       192
Thr Pro His Asp Ser Ala Pro Tyr Gly Ala Leu Asp Met Ala Asp Phe
 50                  55                  60

GAG TTT GAG CAG ATG TTT ACC GAT GCC CTT GGA ATT GAC GAG TAC GGT       240
Glu Phe Glu Gln Met Phe Thr Asp Ala Leu Gly Ile Asp Glu Tyr Gly
 65                  70                  75                  80

GGT CGA CCT GCA CCA GCA GCT CCT ACA CCG GCG GCC CCT GCA CCA GCC       288
Gly Arg Pro Ala Pro Ala Ala Pro Thr Pro Ala Ala Pro Ala Pro Ala
                 85                  90                  95

CCC TCC TGG CCC CTG TCA TCT TCT GTC CCT TCC CAG AAA ACC TAC CAG       336
Pro Ser Trp Pro Leu Ser Ser Ser Val Pro Ser Gln Lys Thr Tyr Gln
                100                 105                 110

GGC AGC TAC GGT TTC CGT CTG GGC TTC TTG CAT TCT GGG ACA GCC AAG       384
Gly Ser Tyr Gly Phe Arg Leu Gly Phe Leu His Ser Gly Thr Ala Lys
                115                 120                 125

TCT GTG ACT TGC ACG TAC TCC CCT GCC CTC AAC AAG ATG TTT TGC CAA       432
Ser Val Thr Cys Thr Tyr Ser Pro Ala Leu Asn Lys Met Phe Cys Gln
            130                 135                 140

CTG GCC AAG ACC TGC CCT GTG CAG CTG TGG GTT GAT TCC ACA CCC CCG       480
Leu Ala Lys Thr Cys Pro Val Gln Leu Trp Val Asp Ser Thr Pro Pro
145                 150                 155                 160

CCC GGC ACC CGT GTC CGC GCC ATG GCC ATC TAC AAG CAG TCA CAG CAC       528
Pro Gly Thr Arg Val Arg Ala Met Ala Ile Tyr Lys Gln Ser Gln His
                165                 170                 175

ATG ACG GAG GTT GTG AGG CGC TGC CCC CAC CAT GAG CGC TGC TCA GAT       576
Met Thr Glu Val Val Arg Arg Cys Pro His His Glu Arg Cys Ser Asp
                180                 185                 190

AGC GAT GGT CTG GCC CCT CCT CAG CAT CTT ATC CGA GTG GAA GGA AAT       624
Ser Asp Gly Leu Ala Pro Pro Gln His Leu Ile Arg Val Glu Gly Asn
            195                 200                 205

TTG CGT GTG GAG TAT TTC ACC CTT CAG ATC CGT GGG CGT GAG CGC TTC       672
Leu Arg Val Glu Tyr Phe Thr Leu Gln Ile Arg Gly Arg Glu Arg Phe
            210                 215                 220

GAG ATG TTC CGA GAG CTG AAT GAG GCC TTG GAA CTC AAG GAT GCC CAG       720
Glu Met Phe Arg Glu Leu Asn Glu Ala Leu Glu Leu Lys Asp Ala Gln
225                 230                 235                 240

GCT GGG AAG GAG CCA GGG GGG AGC AGG GCT CAC TCG AGC CTG CAG CCT       768
Ala Gly Lys Glu Pro Gly Gly Ser Arg Ala His Ser Ser Leu Gln Pro
                245                 250                 255

AGA GCC TTC CAA GCC CTC ATG AAG GAG GAA AGC CCA AAG TGC                810
Arg Ala Phe Gln Ala Leu Met Lys Glu Glu Ser Pro Lys Cys
                260                 265                 270

TGATGA                                                                 816

(2) INFORMATION FOR SEQ ID NO: 32:

(i) SEQUENCE CHARACTERISTICS:
        (A) LENGTH: 270 amino acids
        (B) TYPE: amino acid
        (D) TOPOLOGY: linear (ii) MOLECULE TYPE: protein (xi) SEQUENCE DESCRIPTION: SEQ ID NO: 32:

Met Ser Thr Ala Pro Pro Thr Asp Val Ser Leu Gly Asp Glu Leu His
 1               5                  10                  15
```

```
Leu Asp Gly Glu Asp Val Ala Met Ala His Ala Asp Ala Leu Asp Asp
                20                  25                  30

Phe Asp Leu Asp Met Leu Gly Asp Gly Asp Ser Pro Gly Pro Gly Phe
            35                  40                  45

Thr Pro His Asp Ser Ala Pro Tyr Gly Ala Leu Asp Met Ala Asp Phe
        50                  55                  60

Glu Phe Glu Gln Met Phe Thr Asp Ala Leu Gly Ile Asp Glu Tyr Gly
 65                  70                  75                  80

Gly Arg Pro Ala Pro Ala Ala Pro Thr Pro Ala Ala Pro Ala Pro Ala
                85                  90                  95

Pro Ser Trp Pro Leu Ser Ser Ser Val Pro Ser Gln Lys Thr Tyr Gln
            100                 105                 110

Gly Ser Tyr Gly Phe Arg Leu Gly Phe Leu His Ser Gly Thr Ala Lys
        115                 120                 125

Ser Val Thr Cys Thr Tyr Ser Pro Ala Leu Asn Lys Met Phe Cys Gln
130                 135                 140

Leu Ala Lys Thr Cys Pro Val Gln Leu Trp Val Asp Ser Thr Pro Pro
145                 150                 155                 160

Pro Gly Thr Arg Val Arg Ala Met Ala Ile Tyr Lys Gln Ser Gln His
                165                 170                 175

Met Thr Glu Val Val Arg Arg Cys Pro His His Glu Arg Cys Ser Asp
            180                 185                 190

Ser Asp Gly Leu Ala Pro Pro Gln His Leu Ile Arg Val Glu Gly Asn
        195                 200                 205

Leu Arg Val Glu Tyr Phe Thr Leu Gln Ile Arg Gly Arg Glu Arg Phe
210                 215                 220

Glu Met Phe Arg Glu Leu Asn Glu Ala Leu Glu Leu Lys Asp Ala Gln
225                 230                 235                 240

Ala Gly Lys Glu Pro Gly Gly Ser Arg Ala His Ser Ser Leu Gln Pro
                245                 250                 255

Arg Ala Phe Gln Ala Leu Met Lys Glu Glu Ser Pro Lys Cys
            260                 265                 270
```

(2) INFORMATION FOR SEQ ID NO: 33:

(i) SEQUENCE CHARACTERISTICS:
        (A) LENGTH: 1209 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1203

(xi) SEQUENCE DESCRIPTION: SEQ ID NO: 33:

```
ATG TCC ACG GCC CCC CCG ACC GAT GTC AGC CTG GGG GAC GAG CTC CAC     48
Met Ser Thr Ala Pro Pro Thr Asp Val Ser Leu Gly Asp Glu Leu His
 1               5                  10                  15

TTA GAC GGC GAG GAC GTG GCG ATG GCG CAT GCC GAC GCG CTA GAC GAT     96
Leu Asp Gly Glu Asp Val Ala Met Ala His Ala Asp Ala Leu Asp Asp
                20                  25                  30

TTC GAT CTG GAC ATG TTG GGG GAC GGG GAT TCC CCG GGG CCG GGA TTT    144
Phe Asp Leu Asp Met Leu Gly Asp Gly Asp Ser Pro Gly Pro Gly Phe
            35                  40                  45

ACC CCC CAC GAC TCC GCC CCC TAC GGC GCT CTG GAT ATG GCC GAC TTC    192
Thr Pro His Asp Ser Ala Pro Tyr Gly Ala Leu Asp Met Ala Asp Phe
```

```
            50                      55                      60
GAG TTT GAG CAG ATG TTT ACC GAT GCC CTT GGA ATT GAC GAG TAC GGT      240
Glu Phe Glu Gln Met Phe Thr Asp Ala Leu Gly Ile Asp Glu Tyr Gly
 65                  70                  75                  80

GGT CGA CCT GCA CCA GCA GCT CCT ACA CCG GCG GCC CCT GCA CCA GCC      288
Gly Arg Pro Ala Pro Ala Ala Pro Thr Pro Ala Ala Pro Ala Pro Ala
                 85                  90                  95

CCC TCC TGG CCC CTG TCA TCT TCT GTC CCT TCC CAG AAA ACC TAC CAG      336
Pro Ser Trp Pro Leu Ser Ser Ser Val Pro Ser Gln Lys Thr Tyr Gln
            100                 105                 110

GGC AGC TAC GGT TTC CGT CTG GGC TTC TTG CAT TCT GGG ACA GCC AAG      384
Gly Ser Tyr Gly Phe Arg Leu Gly Phe Leu His Ser Gly Thr Ala Lys
            115                 120                 125

TCT GTG ACT TGC ACG TAC TCC CCT GCC CTC AAC AAG ATG TTT TGC CAA      432
Ser Val Thr Cys Thr Tyr Ser Pro Ala Leu Asn Lys Met Phe Cys Gln
            130                 135                 140

CTG GCC AAG ACC TGC CCT GTG CAG CTG TGG GTT GAT TCC ACA CCC CCG      480
Leu Ala Lys Thr Cys Pro Val Gln Leu Trp Val Asp Ser Thr Pro Pro
145                 150                 155                 160

CCC GGC ACC CGC GTC CGC GCC ATG GCC ATC TAC AAG CAG TCA CAG CAC      528
Pro Gly Thr Arg Val Arg Ala Met Ala Ile Tyr Lys Gln Ser Gln His
                165                 170                 175

ATG ACG GAG GTT GTG AGG CGC TGC CCC CAC CAT GAG CGC TGC TCA GAT      576
Met Thr Glu Val Val Arg Arg Cys Pro His His Glu Arg Cys Ser Asp
                180                 185                 190

AGC GAT GGT CTG GCC CCT CCT CAG CAT CTT ATC CGA GTG GAA GGA AAT      624
Ser Asp Gly Leu Ala Pro Pro Gln His Leu Ile Arg Val Glu Gly Asn
            195                 200                 205

TTG CGT GTG GAG TAT TTG GAT GAC AGA AAC ACT TTT CGA CAT AGT GTG      672
Leu Arg Val Glu Tyr Leu Asp Asp Arg Asn Thr Phe Arg His Ser Val
    210                 215                 220

GTG GTG CCC TAT GAG CCG CCT GAG GTT GGC TCT GAC TGT ACC ACC ATC      720
Val Val Pro Tyr Glu Pro Pro Glu Val Gly Ser Asp Cys Thr Thr Ile
225                 230                 235                 240

CAC TAC AAC TAC ATG TGT AAC AGT TCC TGC ATG GGC GGC ATG AAC CGG      768
His Tyr Asn Tyr Met Cys Asn Ser Ser Cys Met Gly Gly Met Asn Arg
                245                 250                 255

AGG CCC ATC CTC ACC ATC ATC ACA CTG GAA GAC TCC AGT GGT AAT CTA      816
Arg Pro Ile Leu Thr Ile Ile Thr Leu Glu Asp Ser Ser Gly Asn Leu
            260                 265                 270

CTG GGA CGG AAC AGC TTT GAG GTG CGT GTT TGT GCC TGT CCT GGG AGA      864
Leu Gly Arg Asn Ser Phe Glu Val Arg Val Cys Ala Cys Pro Gly Arg
            275                 280                 285

GAC CGG CGC ACA GAG GAA GAG AAT CTC CGC AAG AAA GGG GAG CCT CAC      912
Asp Arg Arg Thr Glu Glu Glu Asn Leu Arg Lys Lys Gly Glu Pro His
            290                 295                 300

CAC GAG CTG CCC CCA GGG AGC ACT AAG CGA GCA CTG CCC AAC AAC ACC      960
His Glu Leu Pro Pro Gly Ser Thr Lys Arg Ala Leu Pro Asn Asn Thr
305                 310                 315                 320

AGC TCC TCT CCC CAG CCA AAG AAG AAA CCA CTG GAT GGA GAA TAT TTC     1008
Ser Ser Ser Pro Gln Pro Lys Lys Lys Pro Leu Asp Gly Glu Tyr Phe
                325                 330                 335

ACC CTT CAG ATC CGT GGG CGT GAG CGC TTC GAG ATG TTC CGA GAG CTG     1056
Thr Leu Gln Ile Arg Gly Arg Glu Arg Phe Glu Met Phe Arg Glu Leu
                340                 345                 350

AAT GAG GCC TTG GAA CTC AAG GAT GCC CAG GCT GGG AAG GAG CCA GGG     1104
Asn Glu Ala Leu Glu Leu Lys Asp Ala Gln Ala Gly Lys Glu Pro Gly
            355                 360                 365

GGG AGC AGG GCT CAC TCC AGC CAC CTG AAG TCC AAA AAG GGT CAG TCT     1152
```

```
                                                   -continued

Gly Ser Arg Ala His Ser Ser His Leu Lys Ser Lys Lys Gly Gln Ser
    370                 375                 380

ACC TCC CGC CAT AAA AAA CTC ATG TTC AAG ACA GAA GGG CCT GAC TCA      1200
Thr Ser Arg His Lys Lys Leu Met Phe Lys Thr Glu Gly Pro Asp Ser
385                 390                 395                 400

GAC TGATGA                                                            1209
Asp (2) INFORMATION FOR SEQ ID NO: 34:

(i) SEQUENCE CHARACTERISTICS:
         (A) LENGTH: 401 amino acids
         (B) TYPE: amino acid
         (D) TOPOLOGY: linear (ii) MOLECULE TYPE: protein (xi) SEQUENCE DESCRIPTION: SEQ ID NO: 34:

Met Ser Thr Ala Pro Pro Thr Asp Val Ser Leu Gly Asp Glu Leu His
1               5                   10                  15

Leu Asp Gly Glu Asp Val Ala Met Ala His Ala Asp Ala Leu Asp Asp
                20                  25                  30

Phe Asp Leu Asp Met Leu Gly Asp Gly Asp Ser Pro Gly Pro Gly Phe
            35                  40                  45

Thr Pro His Asp Ser Ala Pro Tyr Gly Ala Leu Asp Met Ala Asp Phe
        50                  55                  60

Glu Phe Glu Gln Met Phe Thr Asp Ala Leu Gly Ile Asp Glu Tyr Gly
65                  70                  75                  80

Gly Arg Pro Ala Pro Ala Ala Pro Thr Pro Ala Ala Pro Ala Pro Ala
                85                  90                  95

Pro Ser Trp Pro Leu Ser Ser Val Pro Ser Gln Lys Thr Tyr Gln
            100                 105                 110

Gly Ser Tyr Gly Phe Arg Leu Gly Phe Leu His Ser Gly Thr Ala Lys
        115                 120                 125

Ser Val Thr Cys Thr Tyr Ser Pro Ala Leu Asn Lys Met Phe Cys Gln
130                 135                 140

Leu Ala Lys Thr Cys Pro Val Gln Leu Trp Val Asp Ser Thr Pro Pro
145                 150                 155                 160

Pro Gly Thr Arg Val Arg Ala Met Ala Ile Tyr Lys Gln Ser Gln His
                165                 170                 175

Met Thr Glu Val Val Arg Arg Cys Pro His His Glu Arg Cys Ser Asp
            180                 185                 190

Ser Asp Gly Leu Ala Pro Pro Gln His Leu Ile Arg Val Glu Gly Asn
        195                 200                 205

Leu Arg Val Glu Tyr Leu Asp Asp Arg Asn Thr Phe Arg His Ser Val
    210                 215                 220

Val Val Pro Tyr Glu Pro Pro Glu Val Gly Ser Asp Cys Thr Thr Ile
225                 230                 235                 240

His Tyr Asn Tyr Met Cys Asn Ser Ser Cys Met Gly Gly Met Asn Arg
                245                 250                 255

Arg Pro Ile Leu Thr Ile Ile Thr Leu Glu Asp Ser Ser Gly Asn Leu
            260                 265                 270

Leu Gly Arg Asn Ser Phe Glu Val Arg Val Cys Ala Cys Pro Gly Arg
        275                 280                 285

Asp Arg Arg Thr Glu Glu Glu Asn Leu Arg Lys Lys Gly Glu Pro His
    290                 295                 300
```

-continued

```
His Glu Leu Pro Pro Gly Ser Thr Lys Arg Ala Leu Pro Asn Asn Thr
305                 310                 315                 320

Ser Ser Ser Pro Gln Pro Lys Lys Pro Leu Asp Gly Glu Tyr Phe
                325                 330                 335

Thr Leu Gln Ile Arg Gly Arg Glu Arg Phe Glu Met Phe Arg Glu Leu
            340                 345                 350

Asn Glu Ala Leu Glu Leu Lys Asp Ala Gln Ala Gly Lys Glu Pro Gly
        355                 360                 365

Gly Ser Arg Ala His Ser Ser His Leu Lys Ser Lys Lys Gly Gln Ser
    370                 375                 380

Thr Ser Arg His Lys Lys Leu Met Phe Lys Thr Glu Gly Pro Asp Ser
385                 390                 395                 400

Asp
```

(2) INFORMATION FOR SEQ ID NO: 35:

(i) SEQUENCE CHARACTERISTICS:
        (A) LENGTH: 1149 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1143

(xi) SEQUENCE DESCRIPTION: SEQ ID NO: 35:

```
ATG GCC ACG GCC CCC CCG ACC GAT GTC AGC CTG GGG GAC GAG CTC CAC      48
Met Ala Thr Ala Pro Pro Thr Asp Val Ser Leu Gly Asp Glu Leu His
1               5                   10                  15

TTA GAC GGC GAG GAC GTG GCG ATG GCG CAT GCC GAC GCG CTA GAC GAT      96
Leu Asp Gly Glu Asp Val Ala Met Ala His Ala Asp Ala Leu Asp Asp
                20                  25                  30

TTC GAT CTG GAC ATG TTG GGG GAC GGG GAT TCC CCG GGG CCG GGA TTT     144
Phe Asp Leu Asp Met Leu Gly Asp Gly Asp Ser Pro Gly Pro Gly Phe
            35                  40                  45

ACC CCC CAC GAC TCC GCC CCC TAC GGC GCT CTG GAT ATG GCC GAC TTC     192
Thr Pro His Asp Ser Ala Pro Tyr Gly Ala Leu Asp Met Ala Asp Phe
        50                  55                  60

GAG TTT GAG CAG ATG TTT ACC GAT GCC CTT GGA ATT GAC GAG TAC GGT     240
Glu Phe Glu Gln Met Phe Thr Asp Ala Leu Gly Ile Asp Glu Tyr Gly
65                  70                  75                  80

GGT CGA CCT GCA CCA GCA GCT CCT ACA CCG GCG GCC CCT GCA CCA GCC     288
Gly Arg Pro Ala Pro Ala Ala Pro Thr Pro Ala Ala Pro Ala Pro Ala
                85                  90                  95

CCC TCC TGG CCC CTG TCA TCT TCT GTC CCT TCC CAG AAA ACC TAC CAG     336
Pro Ser Trp Pro Leu Ser Ser Ser Val Pro Ser Gln Lys Thr Tyr Gln
            100                 105                 110

GGC AGC TAC GGT TTC CGT CTG GGC TTC TTG CAT TCT GGG ACA GCC AAG     384
Gly Ser Tyr Gly Phe Arg Leu Gly Phe Leu His Ser Gly Thr Ala Lys
        115                 120                 125

TCT GTG ACT TGC ACG TAC TCC CCT GCC CTC AAC AAG ATG TTT TGC CAA     432
Ser Val Thr Cys Thr Tyr Ser Pro Ala Leu Asn Lys Met Phe Cys Gln
130                 135                 140

CTG GCC AAG ACC TGC CCT GTG CAG CTG TGG GTT GAT TCC ACA CCC CCG     480
Leu Ala Lys Thr Cys Pro Val Gln Leu Trp Val Asp Ser Thr Pro Pro
145                 150                 155                 160

CCC GGC ACC CGC GTC CGC GCC ATG GCC ATC TAC AAG CAG TCA CAG CAC     528
Pro Gly Thr Arg Val Arg Ala Met Ala Ile Tyr Lys Gln Ser Gln His
```

-continued

```
                 165                 170                 175
ATG ACG GAG GTT GTG AGG CGC TGC CCC CAC CAT GAG CGC TGC TCA GAT      576
Met Thr Glu Val Val Arg Arg Cys Pro His His Glu Arg Cys Ser Asp
            180                 185                 190

AGC GAT GGT CTG GCC CCT CCT CAG CAT CTT ATC CGA GTG GAA GGA AAT      624
Ser Asp Gly Leu Ala Pro Pro Gln His Leu Ile Arg Val Glu Gly Asn
        195                 200                 205

TTG CGT GTG GAG TAT TTG GAT GAC AGA AAC ACT TTT CGA CAT AGT GTG      672
Leu Arg Val Glu Tyr Leu Asp Asp Arg Asn Thr Phe Arg His Ser Val
    210                 215                 220

GTG GTG CCC TAT GAG CCG CCT GAG GTT GGC TCT GAC TGT ACC ACC ATC      720
Val Val Pro Tyr Glu Pro Pro Glu Val Gly Ser Asp Cys Thr Thr Ile
225                 230                 235                 240

CAC TAC AAC TAC ATG TGT AAC AGT TCC TGC ATG GGC GGC ATG AAC CGG      768
His Tyr Asn Tyr Met Cys Asn Ser Ser Cys Met Gly Gly Met Asn Arg
                245                 250                 255

AGG CCC ATC CTC ACC ATC ATC ACA CTG GAA GAC TCC AGT GGT AAT CTA      816
Arg Pro Ile Leu Thr Ile Ile Thr Leu Glu Asp Ser Ser Gly Asn Leu
            260                 265                 270

CTG GGA CGG AAC AGC TTT GAG GTG CGT GTT TGT GCC TGT CCT GGG AGA      864
Leu Gly Arg Asn Ser Phe Glu Val Arg Val Cys Ala Cys Pro Gly Arg
        275                 280                 285

GAC CGG CGC ACA GAG GAA GAG AAT CTC CGC AAG AAA GGG GAG CCT CAC      912
Asp Arg Arg Thr Glu Glu Glu Asn Leu Arg Lys Lys Gly Glu Pro His
    290                 295                 300

CAC GAG CTG CCC CCA GGG AGC ACT AAG CGA GCA CTG CCC AAC AAC ACC      960
His Glu Leu Pro Pro Gly Ser Thr Lys Arg Ala Leu Pro Asn Asn Thr
305                 310                 315                 320

AGC TCC TCT CCC CAG CCA AAG AAG AAA CCA CTG GAT GGA GAA TAT TTC     1008
Ser Ser Ser Pro Gln Pro Lys Lys Lys Pro Leu Asp Gly Glu Tyr Phe
                325                 330                 335

ACC CTT CAG ATC CGT GGG CGT GAG CGC TTC GAG ATG TTC CGA GAG GAT     1056
Thr Leu Gln Ile Arg Gly Arg Glu Arg Phe Glu Met Phe Arg Glu Asp
            340                 345                 350

CTG AAG GCC CTC AAG GAG AAG CTG AAG GCC CTG GAG GAG AAG CTG AAG     1104
Leu Lys Ala Leu Lys Glu Lys Leu Lys Ala Leu Glu Glu Lys Leu Lys
        355                 360                 365

GCC CTG GAG GAG AAG CTG AAG GCA CTA GTG GGG GAG CGA TGA TGA         1149
Ala Leu Glu Glu Lys Leu Lys Ala Leu Val Gly Glu Arg
    370                 375                 380
```

(2) INFORMATION FOR SEQ ID NO: 36:

(i) SEQUENCE CHARACTERISTICS:
        (A) LENGTH: 381 amino acids
        (B) TYPE: amino acid
        (D) TOPOLOGY: linear (ii) MOLECULE TYPE: protein (xi) SEQUENCE DESCRIPTION: SEQ ID NO: 36:

```
Met Ala Thr Ala Pro Pro Thr Asp Val Ser Leu Gly Asp Glu Leu His
 1               5                  10                  15

Leu Asp Gly Glu Asp Val Ala Met Ala His Ala Asp Ala Leu Asp Asp
            20                  25                  30

Phe Asp Leu Asp Met Leu Gly Asp Gly Asp Ser Pro Gly Pro Gly Phe
        35                  40                  45

Thr Pro His Asp Ser Ala Pro Tyr Gly Ala Leu Asp Met Ala Asp Phe
    50                  55                  60

Glu Phe Glu Gln Met Phe Thr Asp Ala Leu Gly Ile Asp Glu Tyr Gly
```

```
                65                  70                  75                  80
            Gly Arg Pro Ala Pro Ala Ala Pro Thr Pro Ala Ala Pro Ala Pro Ala
                                85                  90                  95
            Pro Ser Trp Pro Leu Ser Ser Val Pro Ser Gln Lys Thr Tyr Gln
                        100                 105                 110
            Gly Ser Tyr Gly Phe Arg Leu Gly Phe Leu His Ser Gly Thr Ala Lys
                        115                 120                 125
            Ser Val Thr Cys Thr Tyr Ser Pro Ala Leu Asn Lys Met Phe Cys Gln
                130                 135                 140
            Leu Ala Lys Thr Cys Pro Val Gln Leu Trp Val Asp Ser Thr Pro Pro
            145                 150                 155                 160
            Pro Gly Thr Arg Val Arg Ala Met Ala Ile Tyr Lys Gln Ser Gln His
                                165                 170                 175
            Met Thr Glu Val Val Arg Arg Cys Pro His His Glu Arg Cys Ser Asp
                            180                 185                 190
            Ser Asp Gly Leu Ala Pro Pro Gln His Leu Ile Arg Val Glu Gly Asn
                        195                 200                 205
            Leu Arg Val Glu Tyr Leu Asp Asp Arg Asn Thr Phe Arg His Ser Val
                210                 215                 220
            Val Val Pro Tyr Glu Pro Pro Glu Val Gly Ser Asp Cys Thr Thr Ile
            225                 230                 235                 240
            His Tyr Asn Tyr Met Cys Asn Ser Ser Cys Met Gly Gly Met Asn Arg
                                245                 250                 255
            Arg Pro Ile Leu Thr Ile Ile Thr Leu Glu Asp Ser Ser Gly Asn Leu
                            260                 265                 270
            Leu Gly Arg Asn Ser Phe Glu Val Arg Val Cys Ala Cys Pro Gly Arg
                        275                 280                 285
            Asp Arg Arg Thr Glu Glu Asn Leu Arg Lys Lys Gly Glu Pro His
                290                 295                 300
            His Glu Leu Pro Pro Gly Ser Thr Lys Arg Ala Leu Pro Asn Asn Thr
            305                 310                 315                 320
            Ser Ser Ser Pro Gln Pro Lys Lys Lys Pro Leu Asp Gly Glu Tyr Phe
                                325                 330                 335
            Thr Leu Gln Ile Arg Gly Arg Glu Arg Phe Glu Met Phe Arg Glu Asp
                            340                 345                 350
            Leu Lys Ala Leu Lys Glu Lys Leu Lys Ala Leu Glu Glu Lys Leu Lys
                        355                 360                 365
            Ala Leu Glu Glu Lys Leu Lys Ala Leu Val Gly Glu Arg
                370                 375                 380

(2) INFORMATION FOR SEQ ID NO: 37:

(i) SEQUENCE CHARACTERISTICS:
            (A) LENGTH: 1611 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..1605

(xi) SEQUENCE DESCRIPTION: SEQ ID NO: 37:

ATG GCC CAG GTG CAG CTG CAG GAG TCA GGG GCA GAG CTT GTG GGG TCA           48
Met Ala Gln Val Gln Leu Gln Glu Ser Gly Ala Glu Leu Val Gly Ser
 1               5                  10                  15
```

-continued

| | |
|---|---|
| GGG GCC TCA GTC AAG TTG TCC TGC ACA GCT TCT GGC TTC AAC ATT AAA<br>Gly Ala Ser Val Lys Leu Ser Cys Thr Ala Ser Gly Phe Asn Ile Lys<br>                20                       25                      30 | 96 |
| GAC TAC TAT ATG CAC TGG GTG AAG CAG AGG CCT GAA CAG GGC CTG GAG<br>Asp Tyr Tyr Met His Trp Val Lys Gln Arg Pro Glu Gln Gly Leu Glu<br>              35                      40                      45 | 144 |
| TGG ATT GGA TGG ATT GAT CCT GAG AAT GGT GAT ACT GAA TAT GCC CCG<br>Trp Ile Gly Trp Ile Asp Pro Glu Asn Gly Asp Thr Glu Tyr Ala Pro<br>50                      55                      60 | 192 |
| AAG TTC CAG GGC AAG GCC ACT ATG ACT GCA GAC ACA TCC TCC AAT ACA<br>Lys Phe Gln Gly Lys Ala Thr Met Thr Ala Asp Thr Ser Ser Asn Thr<br>65                      70                      75                      80 | 240 |
| GCC TAC CTG CAG CTC AGC AGC CTG GCA TCT GAG GAC ACT GCC GTC TAT<br>Ala Tyr Leu Gln Leu Ser Ser Leu Ala Ser Glu Asp Thr Ala Val Tyr<br>              85                      90                      95 | 288 |
| TAT TGT AAT TTT TAC GGG GAT GCT TTG GAC TAC TGG GGC CAA GGG ACC<br>Tyr Cys Asn Phe Tyr Gly Asp Ala Leu Asp Tyr Trp Gly Gln Gly Thr<br>          100                      105                    110 | 336 |
| ACG GTC ACC GTC TCC TCA GGT GGA GGC GGT TCA GGC GGA GGT GGC TCT<br>Thr Val Thr Val Ser Ser Gly Gly Gly Gly Ser Gly Gly Gly Gly Ser<br>          115                      120                    125 | 384 |
| GGC GGT GGC GGA TCG GAT GTT TTG ATG ACC CAA ACT CCA CTC ACT TTG<br>Gly Gly Gly Gly Ser Asp Val Leu Met Thr Gln Thr Pro Leu Thr Leu<br>130                      135                      140 | 432 |
| TCG GTT ACC ATT GGA CAA CCA GCC TCC ATC TCT TGC AAG TCA AGT CAG<br>Ser Val Thr Ile Gly Gln Pro Ala Ser Ile Ser Cys Lys Ser Ser Gln<br>145                      150                      155                    160 | 480 |
| AGC CTC TTG GAT AGT GAT GGA AAG ACA TAT TTG AAT TGG TTG TTA CAG<br>Ser Leu Leu Asp Ser Asp Gly Lys Thr Tyr Leu Asn Trp Leu Leu Gln<br>                  165                      170                    175 | 528 |
| AGG CCA GGC CAG TCT CCA AAG CGC CTA ATC TAT CTG GTG TCT AAA CTG<br>Arg Pro Gly Gln Ser Pro Lys Arg Leu Ile Tyr Leu Val Ser Lys Leu<br>          180                      185                    190 | 576 |
| GAC TCT GGA GTC CCT GAC AGG TTC ACT GGC AGT GGA TCA GGG ACA GAT<br>Asp Ser Gly Val Pro Asp Arg Phe Thr Gly Ser Gly Ser Gly Thr Asp<br>          195                      200                    205 | 624 |
| TTC ACA CTG AAA ATC AAC AGA GTG GAG GCT GAG GAT TTG GGA GTT TAT<br>Phe Thr Leu Lys Ile Asn Arg Val Glu Ala Glu Asp Leu Gly Val Tyr<br>210                      215                      220 | 672 |
| TAT TGC TGG CAA GGT ACA CAT TCT CCG CTC ACG TTC GGT GCT GGG ACC<br>Tyr Cys Trp Gln Gly Thr His Ser Pro Leu Thr Phe Gly Ala Gly Thr<br>225                      230                      235                    240 | 720 |
| AAG CTG GAG CTG AAA CGG GCG GCC GCA TTG CAG ACG CGT CGA CCT GCA<br>Lys Leu Glu Leu Lys Arg Ala Ala Ala Leu Gln Thr Arg Arg Pro Ala<br>          245                      250                    255 | 768 |
| CCA GCA GCT CCT ACA CCG GCG GCC CCT GCA CCA GCC CCC TCC TGG CCC<br>Pro Ala Ala Pro Thr Pro Ala Ala Pro Ala Pro Ala Pro Ser Trp Pro<br>                  260                      265                    270 | 816 |
| CTG TCA TCT TCT GTC CCT TCC CAG AAA ACC TAC CAG GGC AGC TAC GGT<br>Leu Ser Ser Ser Val Pro Ser Gln Lys Thr Tyr Gln Gly Ser Tyr Gly<br>          275                      280                    285 | 864 |
| TTC CGT CTG GGC TTC TTG CAT TCT GGG ACA GCC AAG TCT GTG ACT TGC<br>Phe Arg Leu Gly Phe Leu His Ser Gly Thr Ala Lys Ser Val Thr Cys<br>290                      295                      300 | 912 |
| ACG TAC TCC CCT GCC CTC AAC AAG ATG TTT TGC CAA CTG GCC AAG ACC<br>Thr Tyr Ser Pro Ala Leu Asn Lys Met Phe Cys Gln Leu Ala Lys Thr<br>305                      310                      315                    320 | 960 |
| TGC CCT GTG CAG CTG TGG GTT GAT TCC ACA CCC CCG CCC GGC ACC CGC<br>Cys Pro Val Gln Leu Trp Val Asp Ser Thr Pro Pro Pro Gly Thr Arg | 1008 |

```
                    325                 330                 335
GTC CGC GCC ATG GCC ATC TAC AAG CAG TCA CAG CAC ATG ACG GAG GTT         1056
Val Arg Ala Met Ala Ile Tyr Lys Gln Ser Gln His Met Thr Glu Val
            340                 345                 350

GTG AGG CGC TGC CCC CAC CAT GAG CGC TGC TCA GAT AGC GAT GGT CTG         1104
Val Arg Arg Cys Pro His His Glu Arg Cys Ser Asp Ser Asp Gly Leu
            355                 360                 365

GCC CCT CCT CAG CAT CTT ATC CGA GTG GAA GGA AAT TTG CGT GTG GAG         1152
Ala Pro Pro Gln His Leu Ile Arg Val Glu Gly Asn Leu Arg Val Glu
370                 375                 380

TAT TTG GAT GAC AGA AAC ACT TTT CGA CAT AGT GTG GTG GTG CCC TAT         1200
Tyr Leu Asp Asp Arg Asn Thr Phe Arg His Ser Val Val Val Pro Tyr
385                 390                 395                 400

GAG CCG CCT GAG GTT GGC TCT GAC TGT ACC ACC ATC CAC TAC AAC TAC         1248
Glu Pro Pro Glu Val Gly Ser Asp Cys Thr Thr Ile His Tyr Asn Tyr
                405                 410                 415

ATG TGT AAC AGT TCC TGC ATG GGC GGC ATG AAC CGG AGG CCC ATC CTC         1296
Met Cys Asn Ser Ser Cys Met Gly Gly Met Asn Arg Arg Pro Ile Leu
            420                 425                 430

ACC ATC ATC ACA CTG GAA GAC TCC AGT GGT AAT CTA CTG GGA CGG AAC         1344
Thr Ile Ile Thr Leu Glu Asp Ser Ser Gly Asn Leu Leu Gly Arg Asn
            435                 440                 445

AGC TTT GAG GTG CGT GTT TGT GCC TGT CCT GGG AGA GAC CGG CGC ACA         1392
Ser Phe Glu Val Arg Val Cys Ala Cys Pro Gly Arg Asp Arg Arg Thr
450                 455                 460

GAG GAA GAG AAT CTC CGC AAG AAA GGG GAG CCT CAC CAC GAG CTG CCC         1440
Glu Glu Glu Asn Leu Arg Lys Lys Gly Glu Pro His His Glu Leu Pro
465                 470                 475                 480

CCA GGG AGC ACT AAG CGA GCA CTG CCC AAC AAC ACC AGC TCC TCT CCC         1488
Pro Gly Ser Thr Lys Arg Ala Leu Pro Asn Asn Thr Ser Ser Ser Pro
                485                 490                 495

CAG CCA AAG AAG AAA CCA CTG GAT GGG GAT CTG AAG GCC CTC AAG GAG         1536
Gln Pro Lys Lys Lys Pro Leu Asp Gly Asp Leu Lys Ala Leu Lys Glu
            500                 505                 510

AAG CTG AAG GCC CTG GAG GAG AAG CTG AAG GCC CTG GAG GAG AAG CTG         1584
Lys Leu Lys Ala Leu Glu Glu Lys Leu Lys Ala Leu Glu Glu Lys Leu
            515                 520                 525

AAG GCA CTA GTG GGG GAG CGA TGATGA                                      1611
Lys Ala Leu Val Gly Glu Arg
530                 535

(2) INFORMATION FOR SEQ ID NO: 38:

(i) SEQUENCE CHARACTERISTICS:
        (A) LENGTH: 535 amino acids
        (B) TYPE: amino acid
        (D) TOPOLOGY: linear (ii) MOLECULE TYPE: protein (xi) SEQUENCE DESCRIPTION: SEQ ID NO: 38:

Met Ala Gln Val Gln Leu Gln Glu Ser Gly Ala Glu Leu Val Gly Ser
 1               5                  10                  15

Gly Ala Ser Val Lys Leu Ser Cys Thr Ala Ser Gly Phe Asn Ile Lys
                20                  25                  30

Asp Tyr Tyr Met His Trp Val Lys Gln Arg Pro Glu Gln Gly Leu Glu
            35                  40                  45

Trp Ile Gly Trp Ile Asp Pro Glu Asn Gly Asp Thr Glu Tyr Ala Pro
        50                  55                  60

Lys Phe Gln Gly Lys Ala Thr Met Thr Ala Asp Thr Ser Ser Asn Thr
```

-continued

```
                65                  70                  75                  80
Ala Tyr Leu Gln Leu Ser Ser Leu Ala Ser Glu Asp Thr Ala Val Tyr
                        85                  90                  95
Tyr Cys Asn Phe Tyr Gly Asp Ala Leu Asp Tyr Trp Gly Gln Gly Thr
                100                 105                 110
Thr Val Thr Val Ser Ser Gly Gly Gly Gly Ser Gly Gly Gly Gly Ser
                115                 120                 125
Gly Gly Gly Gly Ser Asp Val Leu Met Thr Gln Thr Pro Leu Thr Leu
        130                 135                 140
Ser Val Thr Ile Gly Gln Pro Ala Ser Ile Ser Cys Lys Ser Ser Gln
145                 150                 155                 160
Ser Leu Leu Asp Ser Asp Gly Lys Thr Tyr Leu Asn Trp Leu Leu Gln
                165                 170                 175
Arg Pro Gly Gln Ser Pro Lys Arg Leu Ile Tyr Leu Val Ser Lys Leu
                180                 185                 190
Asp Ser Gly Val Pro Asp Arg Phe Thr Gly Ser Gly Ser Gly Thr Asp
            195                 200                 205
Phe Thr Leu Lys Ile Asn Arg Val Glu Ala Glu Asp Leu Gly Val Tyr
        210                 215                 220
Tyr Cys Trp Gln Gly Thr His Ser Pro Leu Thr Phe Gly Ala Gly Thr
225                 230                 235                 240
Lys Leu Glu Leu Lys Arg Ala Ala Ala Leu Gln Thr Arg Arg Pro Ala
                245                 250                 255
Pro Ala Ala Pro Thr Pro Ala Ala Pro Ala Pro Ala Pro Ser Trp Pro
                260                 265                 270
Leu Ser Ser Ser Val Pro Ser Gln Lys Thr Tyr Gln Gly Ser Tyr Gly
            275                 280                 285
Phe Arg Leu Gly Phe Leu His Ser Gly Thr Ala Lys Ser Val Thr Cys
        290                 295                 300
Thr Tyr Ser Pro Ala Leu Asn Lys Met Phe Cys Gln Leu Ala Lys Thr
305                 310                 315                 320
Cys Pro Val Gln Leu Trp Val Asp Ser Thr Pro Pro Gly Thr Arg
                325                 330                 335
Val Arg Ala Met Ala Ile Tyr Lys Gln Ser Gln His Met Thr Glu Val
                340                 345                 350
Val Arg Arg Cys Pro His His Glu Arg Cys Ser Asp Ser Asp Gly Leu
            355                 360                 365
Ala Pro Pro Gln His Leu Ile Arg Val Glu Gly Asn Leu Arg Val Glu
        370                 375                 380
Tyr Leu Asp Asp Arg Asn Thr Phe Arg His Ser Val Val Val Pro Tyr
385                 390                 395                 400
Glu Pro Pro Glu Val Gly Ser Asp Cys Thr Thr Ile His Tyr Asn Tyr
                405                 410                 415
Met Cys Asn Ser Ser Cys Met Gly Gly Met Asn Arg Arg Pro Ile Leu
                420                 425                 430
Thr Ile Ile Thr Leu Glu Asp Ser Ser Gly Asn Leu Leu Gly Arg Asn
            435                 440                 445
Ser Phe Glu Val Arg Val Cys Ala Cys Pro Gly Arg Asp Arg Arg Thr
        450                 455                 460
Glu Glu Glu Asn Leu Arg Lys Lys Gly Glu Pro His His Glu Leu Pro
465                 470                 475                 480
Pro Gly Ser Thr Lys Arg Ala Leu Pro Asn Asn Thr Ser Ser Ser Pro
                485                 490                 495
```

```
Gln Pro Lys Lys Lys Pro Leu Asp Gly Asp Leu Lys Ala Leu Lys Glu
            500                 505                 510

Lys Leu Lys Ala Leu Glu Glu Lys Leu Lys Ala Leu Glu Glu Lys Leu
            515                 520                 525

Lys Ala Leu Val Gly Glu Arg
            530                 535

(2) INFORMATION FOR SEQ ID NO: 39:

(i) SEQUENCE CHARACTERISTICS:
        (A) LENGTH: 1065 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1059

(xi) SEQUENCE DESCRIPTION: SEQ ID NO: 39:

ATG GGA GAA TAT TTC ACC CTT CAG ATC CGT GGG CGT GAG CGC TTC GAG        48
Met Gly Glu Tyr Phe Thr Leu Gln Ile Arg Gly Arg Glu Arg Phe Glu
 1               5                  10                  15

ATG TTC CGA GAG CTG AAT GAG GCC TTG GAA CTC AAG GAT GCC CAG GCT        96
Met Phe Arg Glu Leu Asn Glu Ala Leu Glu Leu Lys Asp Ala Gln Ala
                20                  25                  30

GGG AAG GAG CCA GGG GGG AGC AGG GCT CAC TCC AGC CAC CTG AAG TCC       144
Gly Lys Glu Pro Gly Gly Ser Arg Ala His Ser Ser His Leu Lys Ser
            35                  40                  45

AAA AAG GGT CAG TCT ACC TCC CGC CAT AAA AAA CTC ATG TTC AAG ACA       192
Lys Lys Gly Gln Ser Thr Ser Arg His Lys Lys Leu Met Phe Lys Thr
    50                  55                  60

GAA GGG CCT GAC TCA GAC GGT CGA CCT GCA CCA GCA GCT CCT ACA CCG       240
Glu Gly Pro Asp Ser Asp Gly Arg Pro Ala Pro Ala Ala Pro Thr Pro
65                  70                  75                  80

GCG GCC CCT GCA CCA GCC CCC TCC TGG CCC CTG TCA TCT TCT GTC CCT       288
Ala Ala Pro Ala Pro Ala Pro Ser Trp Pro Leu Ser Ser Ser Val Pro
                85                  90                  95

TCC CAG AAA ACC TAC CAG GGC AGC TAC GGT TTC CGT CTG GGC TTC TTG       336
Ser Gln Lys Thr Tyr Gln Gly Ser Tyr Gly Phe Arg Leu Gly Phe Leu
            100                 105                 110

CAT TCT GGG ACA GCC AAG TCT GTG ACT TGC ACG TAC TCC CCT GCC CTC       384
His Ser Gly Thr Ala Lys Ser Val Thr Cys Thr Tyr Ser Pro Ala Leu
        115                 120                 125

AAC AAG ATG TTT TGC CAA CTG GCC AAG ACC TGC CCT GTG CAG CTG TGG       432
Asn Lys Met Phe Cys Gln Leu Ala Lys Thr Cys Pro Val Gln Leu Trp
    130                 135                 140

GTT GAT TCC ACA CCC CCG CCC GGC ACC CGC GTC CGC GCC ATG GCC ATC       480
Val Asp Ser Thr Pro Pro Pro Gly Thr Arg Val Arg Ala Met Ala Ile
145                 150                 155                 160

TAC AAG CAG TCA CAG CAC ATG ACG GAG GTT GTG AGG CGC TGC CCC CAC       528
Tyr Lys Gln Ser Gln His Met Thr Glu Val Val Arg Arg Cys Pro His
                165                 170                 175

CAT GAG CGC TGC TCA GAT AGC GAT GGT CTG GCC CCT CCT CAG CAT CTT       576
His Glu Arg Cys Ser Asp Ser Asp Gly Leu Ala Pro Pro Gln His Leu
            180                 185                 190

ATC CGA GTG GAA GGA AAT TTG CGT GTG GAG TAT TTG GAT GAC AGA AAC       624
Ile Arg Val Glu Gly Asn Leu Arg Val Glu Tyr Leu Asp Asp Arg Asn
        195                 200                 205
```

```
ACT TTT CGA CAT AGT GTG GTG GTG CCC TAT GAG CCG CCT GAG GTT GGC     672
Thr Phe Arg His Ser Val Val Val Pro Tyr Glu Pro Pro Glu Val Gly
    210                 215                 220

TCT GAC TGT ACC ACC ATC CAC TAC AAC TAC ATG TGT AAC AGT TCC TGC     720
Ser Asp Cys Thr Thr Ile His Tyr Asn Tyr Met Cys Asn Ser Ser Cys
225                 230                 235                 240

ATG GGC GGC ATG AAC CGG AGG CCC ATC CTC ACC ATC ATC ACA CTG GAA     768
Met Gly Gly Met Asn Arg Arg Pro Ile Leu Thr Ile Ile Thr Leu Glu
                245                 250                 255

GAC TCC AGT GGT AAT CTA CTG GGA CGG AAC AGC TTT GAG GTG CGT GTT     816
Asp Ser Ser Gly Asn Leu Leu Gly Arg Asn Ser Phe Glu Val Arg Val
            260                 265                 270

TGT GCC TGT CCT GGG AGA GAC CGG CGC ACA GAG GAA GAG AAT CTC CGC     864
Cys Ala Cys Pro Gly Arg Asp Arg Arg Thr Glu Glu Glu Asn Leu Arg
        275                 280                 285

AAG AAA GGG GAG CCT CAC CAC GAG CTG CCC CCA GGG AGC ACT AAG CGA     912
Lys Lys Gly Glu Pro His His Glu Leu Pro Pro Gly Ser Thr Lys Arg
    290                 295                 300

GCA CTG CCC AAC AAC ACC AGC TCC TCT CCC CAG CCA AAG AAG AAA CCA     960
Ala Leu Pro Asn Asn Thr Ser Ser Ser Pro Gln Pro Lys Lys Lys Pro
305                 310                 315                 320

CTG GAT GGG GAT CTG AAG GCC CTC AAG GAG AAG CTG AAG GCC CTG GAG    1008
Leu Asp Gly Asp Leu Lys Ala Leu Lys Glu Lys Leu Lys Ala Leu Glu
                325                 330                 335

GAG AAG CTG AAG GCC CTG GAG GAG AAG CTG AAG GCA CTA GTG GGG GAG    1056
Glu Lys Leu Lys Ala Leu Glu Glu Lys Leu Lys Ala Leu Val Gly Glu
            340                 345                 350

CGA TGATGA                                                         1065
Arg (2) INFORMATION FOR SEQ ID NO: 40:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO: 40:

Met Gly Glu Tyr Phe Thr Leu Gln Ile Arg Gly Arg Glu Arg Phe Glu
 1               5                  10                  15

Met Phe Arg Glu Leu Asn Glu Ala Leu Glu Leu Lys Asp Ala Gln Ala
                20                  25                  30

Gly Lys Glu Pro Gly Gly Ser Arg Ala His Ser Ser His Leu Lys Ser
            35                  40                  45

Lys Lys Gly Gln Ser Thr Ser Arg His Lys Lys Leu Met Phe Lys Thr
        50                  55                  60

Glu Gly Pro Asp Ser Asp Gly Arg Pro Ala Pro Ala Pro Thr Pro
65                  70                  75                  80

Ala Ala Pro Ala Pro Ala Pro Ser Trp Pro Leu Ser Ser Val Pro
                85                  90                  95

Ser Gln Lys Thr Tyr Gln Gly Ser Tyr Gly Phe Arg Leu Gly Phe Leu
                100                 105                 110

His Ser Gly Thr Ala Lys Ser Val Thr Cys Thr Tyr Ser Pro Ala Leu
            115                 120                 125

Asn Lys Met Phe Cys Gln Leu Ala Lys Thr Cys Pro Val Gln Leu Trp
        130                 135                 140

Val Asp Ser Thr Pro Pro Pro Gly Thr Arg Val Arg Ala Met Ala Ile
```

-continued

```
           145                 150                 155                 160
Tyr Lys Gln Ser Gln His Met Thr Glu Val Val Arg Arg Cys Pro His
                    165                 170                 175

His Glu Arg Cys Ser Asp Ser Asp Gly Leu Ala Pro Pro Gln His Leu
                180                 185                 190

Ile Arg Val Glu Gly Asn Leu Arg Val Glu Tyr Leu Asp Asp Arg Asn
            195                 200                 205

Thr Phe Arg His Ser Val Val Val Pro Tyr Glu Pro Pro Glu Val Gly
        210                 215                 220

Ser Asp Cys Thr Thr Ile His Tyr Asn Tyr Met Cys Asn Ser Ser Cys
225                 230                 235                 240

Met Gly Gly Met Asn Arg Arg Pro Ile Leu Thr Ile Ile Thr Leu Glu
                245                 250                 255

Asp Ser Ser Gly Asn Leu Leu Gly Arg Asn Ser Phe Glu Val Arg Val
                260                 265                 270

Cys Ala Cys Pro Gly Arg Asp Arg Arg Thr Glu Glu Asn Leu Arg
                275                 280                 285

Lys Lys Gly Glu Pro His His Glu Leu Pro Pro Gly Ser Thr Lys Arg
290                 295                 300

Ala Leu Pro Asn Asn Thr Ser Ser Ser Pro Gln Pro Lys Lys Lys Pro
305                 310                 315                 320

Leu Asp Gly Asp Leu Lys Ala Leu Lys Glu Lys Leu Lys Ala Leu Glu
                325                 330                 335

Glu Lys Leu Lys Ala Leu Glu Glu Lys Leu Lys Ala Leu Val Gly Glu
                340                 345                 350

Arg
```

(2) INFORMATION FOR SEQ ID NO: 41:

(i) SEQUENCE CHARACTERISTICS:
        (A) LENGTH: 963 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..957

(xi) SEQUENCE DESCRIPTION: SEQ ID NO: 41:

```
ATG GGA GAA TAT TTC ACC CTT CAG ATC CGT GGG CGT GAG CGC TTC GAG      48
Met Gly Glu Tyr Phe Thr Leu Gln Ile Arg Gly Arg Glu Arg Phe Glu
1               5                   10                  15

ATG TTC CGA GAG CTG AAT GAG GCC TTG GAA CTC AAG GAT GCC CAG GCT      96
Met Phe Arg Glu Leu Asn Glu Ala Leu Glu Leu Lys Asp Ala Gln Ala
            20                  25                  30

GGG AAG GAG CCA GGT CGA CCT GCA CCA GCA GCT CCT ACA CCG GCG GCC     144
Gly Lys Glu Pro Gly Arg Pro Ala Pro Ala Ala Pro Thr Pro Ala Ala
        35                  40                  45

CCT GCA CCA GCC CCC TCC TGG CCC CTG TCA TCT TCT GTC CCT TCC CAG     192
Pro Ala Pro Ala Pro Ser Trp Pro Leu Ser Ser Ser Val Pro Ser Gln
    50                  55                  60

AAA ACC TAC CAG GGC AGC TAC GGT TTC CGT CTG GGC TTC TTG CAT TCT     240
Lys Thr Tyr Gln Gly Ser Tyr Gly Phe Arg Leu Gly Phe Leu His Ser
65                  70                  75                  80

GGG ACA GCC AAG TCT GTG ACT TGC ACG TAC TCC CCT GCC CTC AAC AAG     288
Gly Thr Ala Lys Ser Val Thr Cys Thr Tyr Ser Pro Ala Leu Asn Lys
```

-continued

```
                        85                      90                       95
ATG TTT TGC CAA CTG GCC AAG ACC TGC CCT GTG CAG CTG TGG GTT GAT           336
Met Phe Cys Gln Leu Ala Lys Thr Cys Pro Val Gln Leu Trp Val Asp
                100                 105                 110

TCC ACA CCC CCG CCC GGC ACC CGC GTC CGC GCC ATG GCC ATC TAC AAG           384
Ser Thr Pro Pro Pro Gly Thr Arg Val Arg Ala Met Ala Ile Tyr Lys
            115                 120                 125

CAG TCA CAG CAC ATG ACG GAG GTT GTG AGG CGC TGC CCC CAC CAT GAG           432
Gln Ser Gln His Met Thr Glu Val Val Arg Arg Cys Pro His His Glu
        130                 135                 140

CGC TGC TCA GAT AGC GAT GGT CTG GCC CCT CCT CAG CAT CTT ATC CGA           480
Arg Cys Ser Asp Ser Asp Gly Leu Ala Pro Pro Gln His Leu Ile Arg
145                 150                 155                 160

GTG GAA GGA AAT TTG CGT GTG GAG TAT TTG GAT GAC AGA AAC ACT TTT           528
Val Glu Gly Asn Leu Arg Val Glu Tyr Leu Asp Asp Arg Asn Thr Phe
                165                 170                 175

CGA CAT AGT GTG GTG GTG CCC TAT GAG CCG CCT GAG GTT GGC TCT GAC           576
Arg His Ser Val Val Val Pro Tyr Glu Pro Pro Glu Val Gly Ser Asp
            180                 185                 190

TGT ACC ACC ATC CAC TAC AAC TAC ATG TGT AAC AGT TCC TGC ATG GGC           624
Cys Thr Thr Ile His Tyr Asn Tyr Met Cys Asn Ser Ser Cys Met Gly
        195                 200                 205

GGC ATG AAC CGG AGG CCC ATC CTC ACC ATC ATC ACA CTG GAA GAC TCC           672
Gly Met Asn Arg Arg Pro Ile Leu Thr Ile Ile Thr Leu Glu Asp Ser
    210                 215                 220

AGT GGT AAT CTA CTG GGA CGG AAC AGC TTT GAG GTG CGT GTT TGT GCC           720
Ser Gly Asn Leu Leu Gly Arg Asn Ser Phe Glu Val Arg Val Cys Ala
225                 230                 235                 240

TGT CCT GGG AGA GAC CGG CGC ACA GAG GAA GAG AAT CTC CGC AAG AAA           768
Cys Pro Gly Arg Asp Arg Arg Thr Glu Glu Glu Asn Leu Arg Lys Lys
                245                 250                 255

GGG GAG CCT CAC CAC GAG CTG CCC CCA GGG AGC ACT AAG CGA GCA CTG           816
Gly Glu Pro His His Glu Leu Pro Pro Gly Ser Thr Lys Arg Ala Leu
            260                 265                 270

CCC AAC AAC ACC AGC TCC TCT CCC CAG CCA AAG AAG AAA CCA CTG GAT           864
Pro Asn Asn Thr Ser Ser Ser Pro Gln Pro Lys Lys Lys Pro Leu Asp
        275                 280                 285

GGG GAT CTG AAG GCC CTC AAG GAG AAG CTG AAG GCC CTG GAG GAG AAG           912
Gly Asp Leu Lys Ala Leu Lys Glu Lys Leu Lys Ala Leu Glu Glu Lys
    290                 295                 300

CTG AAG GCC CTG GAG GAG AAG CTG AAG GCA CTA GTG GGG GAG CGA               957
Leu Lys Ala Leu Glu Glu Lys Leu Lys Ala Leu Val Gly Glu Arg
305                 310                 315

TGATGA                                                                    963
```

(2) INFORMATION FOR SEQ ID NO: 42:

(i) SEQUENCE CHARACTERISTICS:
        (A) LENGTH: 319 amino acids
        (B) TYPE: amino acid
        (D) TOPOLOGY: linear (ii) MOLECULE TYPE: protein (xi) SEQUENCE DESCRIPTION: SEQ ID NO: 42:

```
Met Gly Glu Tyr Phe Thr Leu Gln Ile Arg Gly Arg Glu Arg Phe Glu
1               5                   10                  15

Met Phe Arg Glu Leu Asn Glu Ala Leu Glu Leu Lys Asp Ala Gln Ala
            20                  25                  30

Gly Lys Glu Pro Gly Arg Pro Ala Pro Ala Ala Pro Thr Pro Ala Ala
```

-continued

```
                    35                  40                  45
        Pro Ala Pro Ala Pro Ser Trp Pro Leu Ser Ser Val Pro Ser Gln
                    50                  55                  60
        Lys Thr Tyr Gln Gly Ser Tyr Gly Phe Arg Leu Gly Phe Leu His Ser
        65                  70                  75                  80
        Gly Thr Ala Lys Ser Val Thr Cys Thr Tyr Ser Pro Ala Leu Asn Lys
                        85                  90                  95
        Met Phe Cys Gln Leu Ala Lys Thr Cys Pro Val Gln Leu Trp Val Asp
                        100                 105                 110
        Ser Thr Pro Pro Gly Thr Arg Val Arg Ala Met Ala Ile Tyr Lys
                    115                 120                 125
        Gln Ser Gln His Met Thr Glu Val Val Arg Arg Cys Pro His His Glu
            130                 135                 140
        Arg Cys Ser Asp Ser Asp Gly Leu Ala Pro Pro Gln His Leu Ile Arg
        145                 150                 155                 160
        Val Glu Gly Asn Leu Arg Val Glu Tyr Leu Asp Asp Arg Asn Thr Phe
                        165                 170                 175
        Arg His Ser Val Val Val Pro Tyr Glu Pro Pro Glu Val Gly Ser Asp
                    180                 185                 190
        Cys Thr Thr Ile His Tyr Asn Tyr Met Cys Asn Ser Ser Cys Met Gly
                    195                 200                 205
        Gly Met Asn Arg Arg Pro Ile Leu Thr Ile Ile Thr Leu Glu Asp Ser
                210                 215                 220
        Ser Gly Asn Leu Leu Gly Arg Asn Ser Phe Glu Val Arg Val Cys Ala
        225                 230                 235                 240
        Cys Pro Gly Arg Asp Arg Arg Thr Glu Glu Glu Asn Leu Arg Lys Lys
                        245                 250                 255
        Gly Glu Pro His His Glu Leu Pro Pro Gly Ser Thr Lys Arg Ala Leu
                    260                 265                 270
        Pro Asn Asn Thr Ser Ser Ser Pro Gln Pro Lys Lys Lys Pro Leu Asp
                    275                 280                 285
        Gly Asp Leu Lys Ala Leu Lys Glu Lys Leu Lys Ala Leu Glu Glu Lys
                290                 295                 300
        Leu Lys Ala Leu Glu Glu Lys Leu Lys Ala Leu Val Gly Glu Arg
        305                 310                 315
```

(2) INFORMATION FOR SEQ ID NO: 43:

(i) SEQUENCE CHARACTERISTICS:
        (A) LENGTH: 1011 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1005

(xi) SEQUENCE DESCRIPTION: SEQ ID NO: 43:

```
ATG GGA GAA TAT TTC ACC CTT CAG ATC CGT GGG CGT GAG CGC TTC GAG      48
Met Gly Glu Tyr Phe Thr Leu Gln Ile Arg Gly Arg Glu Arg Phe Glu
 1               5                  10                  15

ATG TTC CGA GAG CTG AAT GAG GCC TTG GAA CTC AAG GAT GCC CAG GCT      96
Met Phe Arg Glu Leu Asn Glu Ala Leu Glu Leu Lys Asp Ala Gln Ala
             20                  25                  30

GGG AAG GAG CCA GGT CGA GGA GGT GGT GGC TCT GGA GGC GGA GGA TCC     144
```

```
Gly Lys Glu Pro Gly Arg Gly Gly Gly Ser Gly Gly Gly Ser
         35                  40                  45

GGC GGT GGA GGT TCT CGA CCT GCA CCA GCA GCT CCT ACA CCG GCG GCC       192
Gly Gly Gly Gly Ser Arg Pro Ala Pro Ala Ala Pro Thr Pro Ala Ala
 50                  55                  60

CCT GCA CCA GCC CCC TCC TGG CCC CTG TCA TCT TCT GTC CCT TCC CAG       240
Pro Ala Pro Ala Pro Ser Trp Pro Leu Ser Ser Ser Val Pro Ser Gln
 65                  70                  75                  80

AAA ACC TAC CAG GGC AGC TAC GGT TTC CGT CTG GGC TTC TTG CAT TCT       288
Lys Thr Tyr Gln Gly Ser Tyr Gly Phe Arg Leu Gly Phe Leu His Ser
                     85                  90                  95

GGG ACA GCC AAG TCT GTG ACT TGC ACG TAC TCC CCT GCC CTC AAC AAG       336
Gly Thr Ala Lys Ser Val Thr Cys Thr Tyr Ser Pro Ala Leu Asn Lys
                100                 105                 110

ATG TTT TGC CAA CTG GCC AAG ACC TGC CCT GTG CAG CTG TGG GTT GAT       384
Met Phe Cys Gln Leu Ala Lys Thr Cys Pro Val Gln Leu Trp Val Asp
            115                 120                 125

TCC ACA CCC CCG CCC GGC ACC CGC GTC CGC GCC ATG GCC ATC TAC AAG       432
Ser Thr Pro Pro Pro Gly Thr Arg Val Arg Ala Met Ala Ile Tyr Lys
130                 135                 140

CAG TCA CAG CAC ATG ACG GAG GTT GTG AGG CGC TGC CCC CAC CAT GAG       480
Gln Ser Gln His Met Thr Glu Val Val Arg Arg Cys Pro His His Glu
145                 150                 155                 160

CGC TGC TCA GAT AGC GAT GGT CTG GCC CCT CCT CAG CAT CTT ATC CGA       528
Arg Cys Ser Asp Ser Asp Gly Leu Ala Pro Pro Gln His Leu Ile Arg
                165                 170                 175

GTG GAA GGA AAT TTG CGT GTG GAG TAT TTG GAT GAC AGA AAC ACT TTT       576
Val Glu Gly Asn Leu Arg Val Glu Tyr Leu Asp Asp Arg Asn Thr Phe
                180                 185                 190

CGA CAT AGT GTG GTG GTG CCC TAT GAG CCG CCT GAG GTT GGC TCT GAC       624
Arg His Ser Val Val Val Pro Tyr Glu Pro Pro Glu Val Gly Ser Asp
            195                 200                 205

TGT ACC ACC ATC CAC TAC AAC TAC ATG TGT AAC AGT TCC TGC ATG GGC       672
Cys Thr Thr Ile His Tyr Asn Tyr Met Cys Asn Ser Ser Cys Met Gly
210                 215                 220

GGC ATG AAC CGG AGG CCC ATC CTC ACC ATC ATC ACA CTG GAA GAC TCC       720
Gly Met Asn Arg Arg Pro Ile Leu Thr Ile Ile Thr Leu Glu Asp Ser
225                 230                 235                 240

AGT GGT AAT CTA CTG GGA CGG AAC AGC TTT GAG GTG CGT GTT TGT GCC       768
Ser Gly Asn Leu Leu Gly Arg Asn Ser Phe Glu Val Arg Val Cys Ala
                245                 250                 255

TGT CCT GGG AGA GAC CGG CGC ACA GAG GAA GAG AAT CTC CGC AAG AAA       816
Cys Pro Gly Arg Asp Arg Arg Thr Glu Glu Glu Asn Leu Arg Lys Lys
                260                 265                 270

GGG GAG CCT CAC CAC GAG CTG CCC CCA GGG AGC ACT AAG CGA GCA CTG       864
Gly Glu Pro His His Glu Leu Pro Pro Gly Ser Thr Lys Arg Ala Leu
            275                 280                 285

CCC AAC AAC ACC AGC TCC TCT CCC CAG CCA AAG AAG AAA CCA CTG GAT       912
Pro Asn Asn Thr Ser Ser Ser Pro Gln Pro Lys Lys Lys Pro Leu Asp
290                 295                 300

GGG GAT CTG AAG GCC CTC AAG GAG AAG CTG AAG GCC CTG GAG GAG AAG       960
Gly Asp Leu Lys Ala Leu Lys Glu Lys Leu Lys Ala Leu Glu Glu Lys
305                 310                 315                 320

CTG AAG GCC CTG GAG GAG AAG CTG AAG GCA CTA GTG GGG GAG CGA          1005
Leu Lys Ala Leu Glu Glu Lys Leu Lys Ala Leu Val Gly Glu Arg
                325                 330                 335

TGATGA                                                                1011
```

(2) INFORMATION FOR SEQ ID NO: 44:

(i) SEQUENCE CHARACTERISTICS:
    (A) LENGTH: 335 amino acids
    (B) TYPE: amino acid
    (D) TOPOLOGY: linear (ii) MOLECULE TYPE: protein (xi) SEQUENCE DESCRIPTION: SEQ ID NO: 44:

```
Met Gly Glu Tyr Phe Thr Leu Gln Ile Arg Gly Arg Glu Arg Phe Glu
 1               5                  10                  15

Met Phe Arg Glu Leu Asn Glu Ala Leu Glu Leu Lys Asp Ala Gln Ala
                20                  25                  30

Gly Lys Glu Pro Gly Arg Gly Gly Gly Ser Gly Gly Gly Gly Ser
            35                  40                  45

Gly Gly Gly Gly Ser Arg Pro Ala Pro Ala Pro Thr Pro Ala Ala
        50                  55                  60

Pro Ala Pro Ala Pro Ser Trp Pro Leu Ser Ser Ser Val Pro Ser Gln
 65                  70                  75                  80

Lys Thr Tyr Gln Gly Ser Tyr Gly Phe Arg Leu Gly Phe Leu His Ser
                85                  90                  95

Gly Thr Ala Lys Ser Val Thr Cys Thr Tyr Ser Pro Ala Leu Asn Lys
                100                 105                 110

Met Phe Cys Gln Leu Ala Lys Thr Cys Pro Val Gln Leu Trp Val Asp
                115                 120                 125

Ser Thr Pro Pro Pro Gly Thr Arg Val Arg Ala Met Ala Ile Tyr Lys
130                 135                 140

Gln Ser Gln His Met Thr Glu Val Val Arg Arg Cys Pro His His Glu
145                 150                 155                 160

Arg Cys Ser Asp Ser Asp Gly Leu Ala Pro Pro Gln His Leu Ile Arg
                165                 170                 175

Val Glu Gly Asn Leu Arg Val Glu Tyr Leu Asp Asp Arg Asn Thr Phe
                180                 185                 190

Arg His Ser Val Val Val Pro Tyr Glu Pro Pro Glu Val Gly Ser Asp
                195                 200                 205

Cys Thr Thr Ile His Tyr Asn Tyr Met Cys Asn Ser Ser Cys Met Gly
210                 215                 220

Gly Met Asn Arg Arg Pro Ile Leu Thr Ile Ile Thr Leu Glu Asp Ser
225                 230                 235                 240

Ser Gly Asn Leu Leu Gly Arg Asn Ser Phe Glu Val Arg Val Cys Ala
                245                 250                 255

Cys Pro Gly Arg Asp Arg Arg Thr Glu Glu Glu Asn Leu Arg Lys Lys
                260                 265                 270

Gly Glu Pro His His Glu Leu Pro Pro Gly Ser Thr Lys Arg Ala Leu
                275                 280                 285

Pro Asn Asn Thr Ser Ser Ser Pro Gln Pro Lys Lys Lys Pro Leu Asp
                290                 295                 300

Gly Asp Leu Lys Ala Leu Lys Glu Lys Leu Lys Ala Leu Glu Glu Lys
305                 310                 315                 320

Leu Lys Ala Leu Glu Glu Lys Leu Lys Ala Leu Val Gly Glu Arg
                325                 330                 335
```

(2) INFORMATION FOR SEQ ID NO: 45:

(i) SEQUENCE CHARACTERISTICS:
        (A) LENGTH: 24 base pairs
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO: 45:

CGGATCCTCT CGGAACATCT CGAA                                          24

(2) INFORMATION FOR SEQ ID NO: 46:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

GCCATGGCCC AGGTGCAGCT GCAGGAGTCA GGGGCAGAGC TTGTGGGGTC AGGGGCCTCA      60

GTCAAGTTGT CCTGCACAGC TTCTGGCTTC AACATTAAAG ACTACTATAT GCACTGGGTG     120

AAGCAGAGGC CTGAACAGGG CCTGGAGTGG ATTGGATGGA TTGATCCTGA GAATGGTGAT     180

ACTGAATATG CCCCGAAGTT CCAGGGCAAG GCCACTATGA CTGCAGACAC ATCCTCCAAT     240

ACAGCCTACC TGCAGCTCAG CAGCCTGGCA TCTGAGGACA CTGCCGTCTA TTATTGTAAT     300

TTTTACGGGG ATGCTTTGGA CTACTGGGGC CAAGGGACCA CGGTCACCGT CTCCTCAGGT     360

GGAGGCGGTT CAGGCGGAGG TGGCTCTGGC GGTGGCGGAT CGGATGTTTT GATGACCCAA     420

ACTCCACTCA CTTTGTCGGT TACCATTGGA CAACCAGCCT CCATCTCTTG CAAGTCAAGT     480

CAGAGCCTCT TGGATAGTGA TGGAAAGACA TATTTGAATT GGTTGTTACA GAGGCCAGGC     540

CAGTCTCCAA AGCGCCTAAT CTATCTGGTG TCTAAACTGG ACTCTGGAGT CCCTGACAGG     600

TTCACTGGCA GTGGATCAGG GACAGATTTC ACACTGAAAA TCAACAGAGT GGAGGCTGAG     660

GATTTGGGAG TTTATTATTG CTGGCAAGGT ACACATTCTC CGCTCACGTT CGGTGCTGGG     720

ACCAAGCTGG AGCTGAAACG GGCGGCCGC                                     749

(2) INFORMATION FOR SEQ ID NO: 47:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 47:

AAGCTTGAAT TCGTTAACGC CACCATGGGA GAATATTTCA CCCTT                    45

(2) INFORMATION FOR SEQ ID NO: 48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 48:

GGGTCGACCT GGCTCCTTCC CAGC                                          24
```

(2) INFORMATION FOR SEQ ID NO: 49:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 49:

```
AAGCTTGAAT TCGTTAACGC CACCATGGGA GAATATTTCA CCCTTCAGAT CCGTGGGCGT    60

GAGCGCTTCG AGATGTTCCG AGAGCTGAAT GAGGCCTTGG AACTCAAGGA TGCCCAGGCT   120

GGGAAGGAGC CAGGTCGACC C                                             141
```

(2) INFORMATION FOR SEQ ID NO: 50:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 50:

```
GGGTCGACCG TCTGAGTCAG GCCCTTC                                       27
```

(2) INFORMATION FOR SEQ ID NO: 51:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO: 51:

```
AAGCTTGAAT TCGTTAACGC CACCATGGGA GAATATTTCA CCCTTCAGAT CCGTGGGCGT    60

GAGCGCTTCG AGATGTTCCG AGAGCTGAAT GAGGCCTTGG AACTCAAGGA TGCCCAGGCT   120

GGGAAGGAGC CAGGGGGGAG CAGGGCTCAC TCCAGCCACC TGAAGTCCAA AAAGGGTCAG   180

TCTACCTCCC GCCATAAAAA ACTCATGTTC AAGACAGAAG GGCCTGACTC AGACGGTCGA   240

CCC                                                                 243
```

(2) INFORMATION FOR SEQ ID NO: 52:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 52:

```
TCGAGGAGGT GGTGGCTCTG GAGGCGGAGG ATCCGGCGGT GGAGGTTC                48
```

(2) INFORMATION FOR SEQ ID NO: 53:

(i) SEQUENCE CHARACTERISTICS:
        (A) LENGTH: 48 base pairs
        (B) TYPE: nucleic acid (C) STRANDEDNESS: single
        (D) TOPOLOGY: linear (ii) MOLECULE TYPE: cDNA (xi) SEQUENCE DESCRIPTION: SEQ ID NO: 53:

TCGAGAACCC CTACCGCCGG ATCCTCCGCC TCCAGAGCCA CCACCTCC                48

(2) INFORMATION FOR SEQ ID NO: 54:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 54:

Gly Gly Gly Ser Gly Gly Gly Ser Gly Gly Gly Ser Gly Gly Gly Se
1               5                   10                  15

(2) INFORMATION FOR SEQ ID NO: 55:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 55:

GATCCGAACA TGTCCCAACA TGTTGA                                       26

(2) INFORMATION FOR SEQ ID NO: 56:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 56:

AGCTTCAACA TGTTGGGACA TGGTCG                                       26

(2) INFORMATION FOR SEQ ID NO: 57:

(i) SEQUENCE CHARACTERISTICS:
        (A) LENGTH: 31 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 57:

Ala His Ser Ser His Leu Lys Ser Lys Lys Gly Gln Ser Thr Ser Ar
1               5                   10                  15

His Lys Lys Leu Met Phe Lys Thr Glu Gly Pro Asp Ser Asp Xaa
                20                  25                  30

(2) INFORMATION FOR SEQ ID NO: 58:

(i) SEQUENCE CHARACTERISTICS:
        (A) LENGTH: 23 amino acids

-continued

```
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 58:

Ala His Ser Ser Leu Gln Pro Arg Ala Phe Gln Ala Leu Met Lys Gl
1               5                   10                  15

Glu Ser Pro Asn Cys Xaa Xaa
            20

(2) INFORMATION FOR SEQ ID NO: 59:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 59:

Ala His Ser Ser Xaa Xaa
1               5
```

P53 PROTEIN VARIANTS AND THERAPEUTIC USES THEREOF

Figure 1:
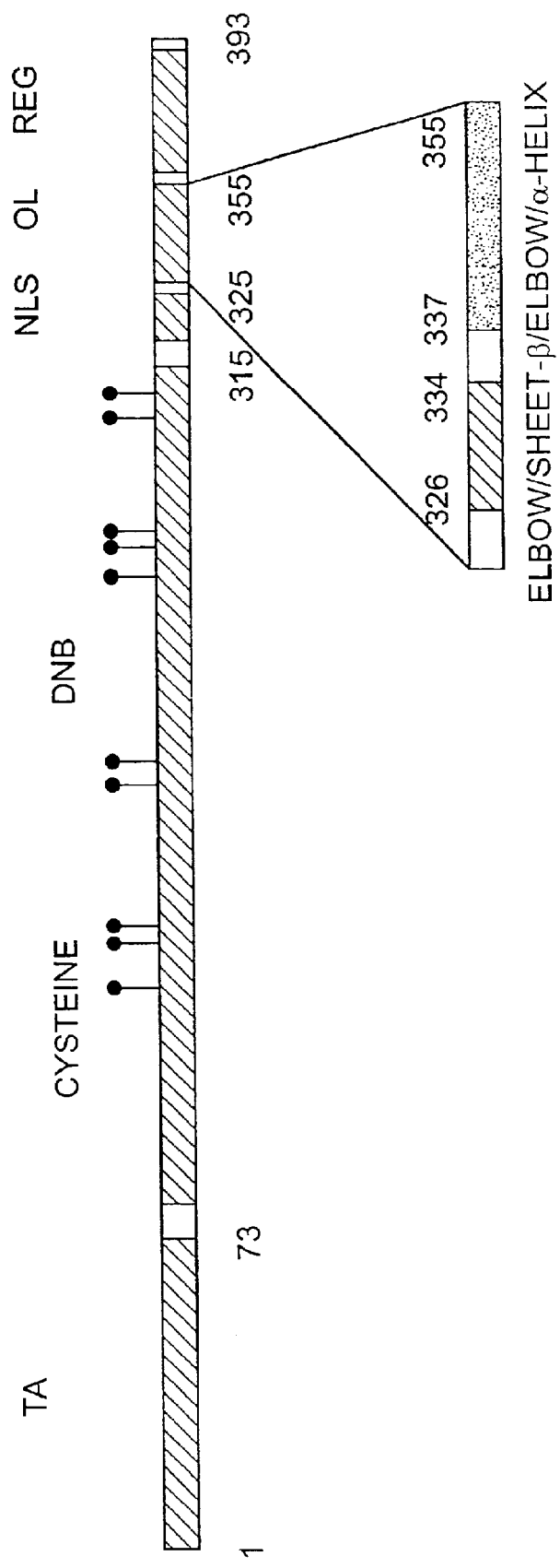

This is a division of application Ser. No. 08/983,035, filed Feb. 20, 1998 (now U.S. Pat. No. 6,326,464 B1), which is the U.S. National Stage of PCT/FR96/01111, filed Jul. 17, 1996, which is incorporated herein by reference.

The present invention relates to proteins derived from the product of the tumour suppressor gene p53, having improved functions for therapeutic use. It relates advantageously to proteins having tumour suppressor and programmed cell death inducing functions superior to that of the wild-type p53 protein, more particularly in pathological situations of proliferation in which the wild-type p53 protein is inactivated. It also relates to the nucleic acids encoding these molecules, the vectors containing them and their therapeutic use, especially in gene therapy. The products of the invention are particularly adapted to the restoration of the functions of p53 in pathological situations such as especially cancers.

The wild-type p53 protein is involved in regulating the cell cycle and in maintaining the integrity of the cell genome. This protein, whose main function is to be an activator of the transcription of some genes, is capable, by a process not yet well defined, of blocking the cell in the G1 phase of the cell cycle during the appearance of mutations during the replication of the genome, and of triggering a number of DNA repair processes. Furthermore, in the event of a malfunctioning of these repair processes or in the event of the appearance of mutation events which are too many to be corrected, this protein is capable of inducing the phenomenon of programmed cell death called apoptosis.

In this manner, the p53 protein acts as a tumour suppressor, by eliminating abnormally differentiated cells or cells whose genome has been damaged.

This principal function of p53 depends on its function as transcription factor, that is to say, in other words, on its double capacity to recognize specific sequences at the level of the genomic DNA and to recruit the general transcription machinery.

The p53 protein comprises 393 amino acids which define 5 functional domains (see FIG. 1):

the transcription activating domain consisting of amino acids 1 to 73 and capable of binding some factors of the general transcription machinery such as the TBP protein. This domain is also the seat for a number of post-translational modifications. It is also the seat of numerous interactions of the p53 protein with numerous other proteins and especially with the cellular protein mdm2 or the protein EBNA5 of the Epstein-Barr virus (EBV), which are capable of blocking the function of the wild-type protein. Furthermore, this domain has amino acid sequences termed PEST for susceptibility to proteolytic degradation;

the DNA-binding domain located between amino acids 73 and 315. The conformation of this central domain of p53 regulates the recognition of DNA sequences specific for the p53 protein. This domain is the seat of two types of alterations which affect the function of the wild-type protein:

(i) the interaction with proteins blocking the function of p53, such as the "large T" antigen of the SV40 virus or the E6 viral proteins of the HPV16 and HPV18 viruses which are capable of causing its degradation by the ubiquitin system. The latter interaction can only occur in the presence of the cellular protein E6ap (enzyme E3 of the ubiquitinilation cascade);

(ii) the point mutations which affect the function of p53, practically all of which are located in this region;

the nuclear localization signal consisting of amino acids 315 to 325 and essential for the correct directing of the protein in the compartment where it will exert its principal function;

the oligomerization domain consisting of amino acids 325 to 355. This 325 to 355 region forms a structure of the type: β sheet (326–334)-elbow (335–336)-α helix (337–355). The alterations of functions located in this region are essentially due to the interaction of the wild-type protein with the various mutant forms which may lead to variable effects on the function of the wild-type protein;

the regulatory domain, consisting of amino acids 365 to 393, which is the seat of a number of post-translational modifications (glycosylations, phosphorylations, attachment of RNA and the like) which modulate the function of the p53 protein in a positive or negative manner. This domain plays an extremely important role in the modulation of the activity of the wild-type protein.

The function of the p53 protein can be disrupted in various ways:

blocking of its function by a number of factors such as for example the "large T" antigen of the SV40 virus, the EBNA5 protein of the Epstein-Barr virus, or the cellular protein mdm2;

destabilization of the protein by increasing its susceptibility to proteolysis, especially by interaction with the E6 protein of the human papilloma viruses HPV16 and HPV18, which promotes the entry of p53 into the ubiquitinilation cycle. In this case, the interaction between these two proteins can only occur through the prior attachment of a cellular protein, the E6ap protein whose site of attachment is poorly known;

point mutations at the level of the p53 gene;

deletion of one or both p53 alleles.

The latter two types of modifications are found in about 50% of the various types of cancer. In this regard, the mutations of the p53 gene recorded in cancer cells affect a very large portion of the gene encoding this protein, and they result in varying modifications of the function of this protein. It can, however, be noted that the great majority of these mutations are located in the central part of the p53 protein which is known to be the region of contact with the genomic sequences specific for the p53 protein.

This explains why most of the mutants of the p53 protein have the principal characteristic of no longer being able to attach to the DNA sequences recognized by the wild-type protein and thus of no longer being able to exert their role as transcription factor. Moreover, some mutants appear to have acquired new functions such as the activation of some genes at the transcriptional level.

The range of these modifications is currently classified into three categories:

the so-called weak mutants, of which the product is a nonfunctional protein which, in the case of a mutation on only one of the two alleles, does not affect the function of the wild-type protein encoded by the other allele. The principal representatives of this category are the H273 and W248 mutants, the latter being specific for the familial Li-Fraumeni syndrome for hypersensitivity to cancerous conditions.

the dominant-negative mutants, of which the product is a nonfunctional protein which, in the case of a mutation on only one of the two alleles and through interaction with the wild-type protein, is capable of blocking the function of the latter by forming nonactive mixed oligomers which can no longer attach to the DNA sequences specific for the wild-type protein. The main representative of this category is the G281 mutant.

the dominant-oncogenic mutants, of which the product is a protein which is capable, on the one hand, of blocking the function of the wild-type protein like the mutants of the previous category and, on the other hand, of promoting tumour development through poorly known mechanisms, thereby offering a gain in function. The principal representative of this category is the H175 mutant.

Taking into account its antitumour and apoptotic properties and its involvement in numerous pathologies of the hyperproliferative type, the wild-type p53 gene has been used in gene and cell therapy procedures. It has in particular been proposed to treat certain hyperproliferative pathologies, and especially cancers, by in vivo administration of the wild-type p53 gene and by restoring the functions of p53. The administration may be preferably carried out by viral and especially adenoviral (WO 94/24297) or retroviral (WO 94/06910) vectors.

It has thus been shown that the introduction of a nucleic acid encoding the wild-type p53 protein made it possible partially to restore a normal regulation of cell growth. However, while these results are encouraging, the effectiveness of these procedures is limited by the therapeutic efficacy of the p53 protein after transfer and expression in vivo in hyperproliferative cells. Indeed, hyperproliferative pathological situations such as cancers result from the disruption of the equilibrium which is established in a network of negative and positive controls of cell growth. The inactivation of the negative control exerted by the wild-type p53 protein through the appearance of a dominant-negative p53 mutant from one of the two alleles, the overexpression of a p53-inactivating cellular partner such as for example mdm2, or even the presence of a viral inactivator following an infection, constitute an unfavourable context for a therapy based on the reintroduction of a wild-type p53 protein which has a high risk of also being inactivated.

It is therefore particularly important to be able to have p53 type proteins having enhanced therapeutic properties. In particular, it would be particularly advantageous to have p53 molecules which are active constitutively and insensitive to the inactivating effects of the dominant-negative and oncogenic mutants or of other cellular or viral proteins such as E6 from HPV18 and HPV16, MDM2, EBNA5 from EBV, and the like, found in tumour cells.

Some modifications of the p53 protein have been described in the prior art. Thus, application WO 95/06661 describes modifications on some residues of the homologous regions of the p53 protein, that is to say in regions 343–351, 372–380 and 381–393. However, these modifications are very minor and do not allow the resulting products to escape the mechanisms of inactivation of the p53 protein in vivo. Furthermore, these proteins do not appear to have an improved activity compared with the wild-type p53 protein.

Hupp et al. (Cell Vol 71 (1992) 875) have described a derivative of p53 comprising a deletion of the 30 C-terminal residues (p53ΔC-ter30). However, while this protein conserves a capacity to bind DNA, its apoptotic properties have not been demonstrated. Furthermore, it is not resistant to the inactivation by the dominant-negative mutants.

Pietenpol et al. (PNAS 91 (1994) 1998) have described chimeric molecules derived from the p53 protein, especially a protein VP16-p53 (80–343)-GCN4. However, this molecule has a substantially reduced DNA-binding and trans-activation capacity compared with the wild-type p53 protein (40%). Moreover, it has a nonselective oligomerization region, with the risk of interacting with other cellular components and thus of inducing a nonspecific cellular response. Moreover, its properties of resistance to the mechanisms of inactivation are not indicated.

The present invention describes new variants of the p53 protein which have improved therapeutic properties. It describes, in particular, variants adapted to use in gene, especially anticancer, therapy. The variants of the invention are derived from the p53 protein by structural modification (s), conserve a p53-type activity and, expressed in hyperproliferative cells, exhibit at least an enhanced property compared with the p53 protein. This may be in particular the antiproliferative and/or apoptotic activity. The it variants of the invention advantageously possess an enhanced antiproliferative and/or apoptotic activity, or one which is more specific for the hyperproliferative cells or which is less sensitive to the various alterations to which the wild-type p53 is subject.

A first subject of the invention relates more particularly to a variant of the p53 protein in which all or part of the oligomerization domain is deleted and replaced by an artificial leucine zipper domain. As indicated above, the p53 protein is inactivated by some mutants, and especially the dominant-negative and oncogenic mutants, found in tumour cells. This inactivation is the result of the formation of inactive mixed oligomers between the wild-type p53 protein and the mutant, which can no longer attach to the specific sequences recognized by the wild-type p53 protein. The present invention now describes variants of the p53 protein which are resistant to the dominant-negative effect of some mutants, that is to say variants which are active in a cellular context exhibiting one or two mutated alleles, which is the case for nearly 90% of p53-dependent human cancers.

In the variants according to the invention, all or part of the natural oligomerization domain of the protein, which does not distinguish between the wild-type and the mutant forms, is thus replaced by an equivalent domain having a specific oligomerization capacity. This modification is carried out using an optimized artificial leucine zipper in order to form a dimer. The molecules according to the invention, comprising such an artificial leucine zipper, are particularly advantageous because they form oligomers only with other molecules carrying the same leucine zipper. They do not therefore form oligomers with the dominant-negative or oncogenic mutants of the p53 protein, which are capable of inactivating them. Neither do they form oligomers with other cellular proteins carrying oligomerization domains, which are also capable of inactivating them or of inducing undesirable effects. They can only form homo-oligomers and therefore possess a high selectivity, ensuring a better activity in a context of hyperproliferative pathology.

According to the present invention, the artificial leucine zipper domain is therefore advantageously a domain not present in the natural state, which ensures selectivity of oligomerization. Most preferably, the oligomerization domain is represented by the sequence SEQ ID No. 1.

In a preferred embodiment of the invention, the variants comprise a deletion of all or part of the oligomerization domain and of all or part of the regulatory domain. As indicated above, the oligomerization domain is located between residues 325–355 inclusive and the regulatory domain between residues 365–393 inclusive. This type of variant is completely advantageous because it lacks all or some of the effects of negative regulation exerted via the C-terminal part (aa 365–393). These variants constitute potentially constitutively active proteins having a non-modulable and possibly enhanced activity. The entire regulatory region is advantageously eliminated. The preferred variants according to the invention comprise a deletion of the C-terminal part of the p53 protein, from residue 326 or 337 inclusive.

Examples of intermediates used for the construction of these variants are especially:

pEC107 (75-325-lz) comprising a deletion of the C-terminal part of the p53 protein, from residue 326, substituted by an artificial oligomerization domain of sequence SEQ ID No. 1;

pEC110 (75-336-lz) comprising a deletion of the C-terminal part of the p53 protein, from residue 337, substituted by an artificial oligomerization domain of sequence SEQ ID No. 1.

According to an advantageous embodiment, in the variants of the invention, the cysteine residue in position 182 of the p53 protein is replaced by a histidine. This mutation makes it possible advantageously to increase the affinity of the variant for the specific binding nucleotide sequences. The introduction of this additional modification therefore makes it possible to obtain a molecule having, in addition, an increased transactivating potential.

Precise examples of intermediate constructs for the preparation of variants according to the invention combining these various modifications are especially:

pEC139 (75-325(H182)-lz) comprising a deletion of the C-terminal part of the p53 protein, from residue 326, substituted by an artificial oligomerization domain of sequence SEQ ID No. 1, and a histidine in position 182;

pEC140 (75-336(H182)-lz) comprising a deletion of the C-terminal part of the p53 protein, from residue 337, substituted by an artificial oligomerization domain of sequence SEQ ID No. 1, and a histidine in position 182.

Advantageously, in the variants according to the invention, all or part of the transactivating domain is also deleted and replaced by a heterologous transactivating domain. It was also indicated above that the transactivating functions of p53 are essential for its activity as tumour suppressor or as inducer of apoptosis. To increase the therapeutic potential of the variants according to the invention, it is particularly advantageous to substitute the natural transactivating domain by a powerful heterologous transactivating domain. These variants thus exhibit numerous advantages. They of course possess a high transactivating activity. However, they are also made insensitive to the effects of negative regulation which are exerted via the N-terminal part (aa 1–73). Indeed, this region contains the PEST sequences responsible for its proteolytic degradation. The substitution of this region by a heterologous transactivating domain lacking PEST sequences makes it possible to reduce this negative regulation. These variants are also characterized by the decrease, or even the suppression, of any interaction with the E6 protein from the human papilloma virus (HPV) which is capable of inducing their degradation. They are also less sensitive to interactions with other cellular proteins such as MDM2 and EBNA which affect the activity of the wild-type p53 protein. The variants thus obtained therefore possess an enhanced stability. The elimination of the domains sensitive to a negative regulation (regulatory and transactivating domains) leads, in a particularly advantageous manner, to molecules which are no longer the target of proteins inducing their proteolysis or their inactivation.

Advantageously, in the variants of the invention, the transactivating domain is eliminated by deletion of residues 1 to 74. The intermediate constructs used for producing such molecules are especially pEC107 (75-325-lz), pEC110 (75-336-lz), pEC139 (75-325(H182)-lz) and pEC140 (75-336 (H182)-lz).

According to a first embodiment, the heterologous transactivating domain is the transactivating domain of VP16. It consists advantageously of residues 411 to 490 of VP16, whose sequence is given in SEQ ID No. 2. Precise examples of variants according to the invention, combining these various modifications, are especially:

pEC114 (VP16-75-325-lz) comprising a deletion of the N-terminal part of the p53 protein comprising residues 1–74, substituted by the transactivating domain of VP16 of sequence SEQ ID No. 2 and a deletion of the C-terminal part of the p53 protein, from residue 326, substituted by an artificial oligomerization domain of sequence SEQ ID No. 1. The complete sequence of the variant pEC114 is represented in SEQ ID No. 25;

pEC116 (VP16-75-336-lz) comprising a deletion of the N-terminal part of the p53 protein comprising residues 1–74, substituted by the transactivating domain of VP16 of sequence SEQ ID No. 2 and a deletion of the C-terminal part of the p53 protein, from residue 337, substituted by an artificial oligomerization domain of sequence SEQ ID No. 1. The complete sequence of the variant pEC116 is represented in SEQ ID No. 26;

pEC147 (VP16-75-325(H182)-lz) comprising a deletion of the N-terminal part of the p53 protein comprising residues 1–74, substituted by the transactivating domain of VP16 of sequence SEQ ID No. 2; a deletion of the C-terminal part of the p53 protein, from residue 326, substituted by an artificial oligomerization domain of sequence SEQ ID No. 1, and a histidine in position 182;

pEC149 (VP16-75-336(H182)-lz) comprising a deletion of the N-terminal part of the p53 protein comprising residues 1–74, substituted by the transactivating domain of VP16 of sequence SEQ ID No. 2; a deletion of the C-terminal part of the p53 protein, from residue 337, substituted by an artificial oligomerization domain of sequence SEQ ID No. 1, and a histidine in position 182.

Because of the abovementioned modifications, the variants of the invention also have potentially enhanced "killer" properties which are the stoppage of the cell cycle and apoptosis. The combination of the modifications mentioned, including the presence of a selective oligomerization domain and an improve transactivating power by substitution of the domain of origin and by the presence of a histidine in 182 indeed confer on the variants of the invention considerably improved therapeutic potentials. In addition, the variants according to the invention make it possible to avoid the appearance of some (dominant-oncogenic) mutants. The gains in function of some mutants of p53 are still poorly defined both at the level of their mechanisms and at the level of the domains of the p53 protein which are involved. It is highly probable that some of these new functions will depend on the combination with some effector cellular partners.

The elimination of the domains involved in these interactions, and whose transforming properties have been demonstrated, within the molecules described in the present application are of the type which prevent the appearance of these gains in oncogenic functions. Thus, the mutations which would appear randomly during the preparation of clinical batches of plasmids encoding the polypeptides described or during the production of clinical batches of viral or chemical vectors encoding these same polypeptides would not create a subpopulation of oncogenic molecules.

Moreover, because of the elimination of some domains of p53 which are essential for the attachment of some molecules which inhibit its function, the variants of the invention also have a higher and more stable therapeutic activity. Finally, the existence of foreign units in the various constructs of the invention (murine AS protein for example, artificial oligomerization domain, and the like) is capable of triggering an immune reaction during the death of the transfected cells and the release, into the extracellular medium, of these various fragments, thus increasing the capacity of the immune system to combat tumour cells.

According to another embodiment, the heterologous transactivating domain is a transactivating domain preferably active in the transformed cells and not in the neighbouring healthy cells. The present invention indeed also describes molecules whose function is exerted essentially in transformed cells and not in the neighbouring healthy cells. Although it seems that the exogenous expression of a wild-type p53 within a differentiated cell comprising endogenous wild-type p53 has little or no effect on viability, it is nevertheless advantageous to be able to have a protein which would be functional only within the targeted cell. This specificity for the tumour cell versus the normal cell is currently greatly worked upon at the level of the specificity of the targeting of the viral vector or of the design of specific expression systems. The present invention now describes derivatives of p53 in which one of the functional domains is switched off in the absence of a cellular activator present essentially in the transformed cells.

Thus, another subject of the invention relates to a variant of the p53 protein which is preferably active in the transformed cells, in which at least one of the functional domains of p53 is deleted completely or in part and is substituted by a heterologous domain which is preferably active in the transformed cells. Preferably, the functional domain of p53 in question is the transactivating domain. Thus, a particularly preferred subject of the invention relates to a variant of the p53 protein which is preferably active in the transformed cells, in which the natural transactivating domain is deleted completely or in part and is substituted by a transactivating domain which is preferably active in the transformed cells. Advantageously, the natural transactivating domain is deleted by elimination of residues 1–74 inclusive from p53.

The invention relates more particularly to variants of p53 which are functional specifically in the presence of an oncogenic Ras protein or of a mutant of p53. These molecules are obtained especially by replacing the transactivating domain of the wild-type p53 protein with a protein domain capable of specifically binding a transactivator or a transactivating complex present in a transformed cell.

The protein domain capable of specifically binding the transcriptional transactivator or the transcriptional transactivating complex present in the molecules of the invention may be of various types. It may be in particular an oligomerization domain in the case where the transactivator or the transactivating complex targeted also comprises such a domain. It may also be any synthetic or natural domain known to interact with the said transactivator or transactivating complex. It may also be an antibody or a fragment or derivative of an antibody directed against the transactivator or transactivating complex.

Advantageously, the heterologous domain consists of an antibody or an antibody fragment or derivative. The antibody fragments or derivatives are for example the fragments Fab or F(ab)'2, the regions VH or VL of an antibody or alternatively single-chain antibodies (ScFv) comprising a VH region bound to a VL region by an arm. The construction of nucleic acid sequences encoding such antibodies modified according to the invention has been described for example in patent U.S. Pat. No. 4,946,778 or in applications WO 94/02610, WO 94/29446.

A preferred construct according to the present invention comprises an ScFv directed against a mutant of the p53 protein. These mutants appear in the transformed cells and possess a transactivating domain. Their recruitment by a variant according to the invention creates a chimeric molecule which is selectively active in the transformed cells.

According to another preferred mode, the ScFv is directed against a transactivating complex, that is to say a complex between a target molecule selectively present in the transformed cells, but lacking transcriptional transactivator activity (for example an oncogenic ras), and a molecule carrying a transactivating domain. The latter advantageously comprises a transactivating domain and a domain for selective binding to the said cellular molecule (for example an anti-ras ScFv). The attachment of this molecule allows the formation of a transcriptional transactivating binary complex, which complex is then recruited by the variant of the invention.

Any other type of modification leading to this specificity of activity can of course be used within the framework of the present invention, such as especially any transactivating domain specific for a cell type.

These selective variants advantageously comprise additional modifications in the C-terminal part as indicated above so as further to improve their properties. Thus, they advantageously comprise a deletion of all or part of the oligomerization domain, which may be replaced by any heterologous oligomerization domain. This is more preferably an artificial oligomerization domain, as defined above.

Precise examples of variants according to the invention which are preferably active in the transformed cells are especially:

ScFv.antip53*-75-325-lz, comprising a deletion of the N-terminal part of the p53 protein comprising residues 1–74, substituted by a protein domain capable of specifically binding a mutant of the p53 protein which is present in a transformed cell, and a deletion of the C-terminal part of the p53 protein, from residue 326, substituted by an artificial oligomerization domain of sequence SEQ ID No. 1;

ScFv.antip53*-75-325(H182)-lz, comprising, in addition, a His182 mutation;

ScFv.antip53*-75-336-lz, comprising a deletion of the N-terminal part of the p53 protein comprising residues 1–74, substituted by a protein domain capable of specifically binding a mutant of the p53 protein which is present in a transformed cell, and a deletion of the C-terminal part of the p53 protein, from residue 337, substituted by an artificial oligomerization domain of sequence SEQ ID No. 1;

ScFv.antip53*-75-336(H182)-lz, comprising, in addition, a His182 mutation;

ScFv.antip53*-75-393, comprising a deletion of the N-terminal part of the p53 protein comprising residues 1–74, substituted by a protein domain capable of specifically binding a mutant of the p53 protein present in a transformed cell;

ScFv.antip53*-75-393(H182), comprising, in addition, a histidine in position 182;

ScFv.antip53*-75-367, comprising a deletion of the N-terminal part of the p53 protein comprising residues 1–74, substituted by a protein domain capable of specifically binding a mutant of the p53 protein present in a transformed cell; and a deletion of the C-terminal part, from residue 368;

ScFv.antip53*-75-367(H182), comprising, in addition, a histidine in position 182;

ScFv.antip53*-75-AS, comprising a deletion of the N-terminal part of the p53 protein comprising residues 1–74, substituted by a protein domain capable of specifically binding a mutant of the p53 protein present in a transformed cell; and a deletion of the C-terminal part, from residue 367, supplemented with the 19 amino acids of sequence SEQ ID No. 3;

ScFv.antip53*-75-AS(H182), comprising, in addition, a histidine in position 182.

In addition, the term preferably active indicates that these variants exert their activity essentially when they are expressed in transformed cells. A residual activity may however exist in the A nontransformed cells, but less than that observed in the transformed cells.

Another subject of the present invention relates to a variant of the p53 protein comprising a deletion of the C-terminal part, from residue 367, fused with the sequence SEQ ID No. 3 (AS). This sequence corresponds to the last 19 amino acids of the alternative splicing product of the murine p53 protein. This variant therefore exhibits a modification of the oligomerization domain based on a protein described in mice as alternative splicing variant of the wild-type protein in which the 27 C-terminal amino acids are replaced by 19 different amino acids.

This variant has an affinity for the sequences specific for binding DNA which is potentially enhanced.

This variant advantageously comprises modifications in the N-terminal part as indicated above so as to further improve its properties. Thus, it advantageously comprises a deletion of all or part of the transactivating domain, which may be replaced by any heterologous transactivating domain. It is more preferably the transactivating domain derived from the protein VP16 or a protein domain capable of specifically binding a transactivator or a transactivating complex present in a transformed cell. In addition, the residue 182 of the p53 protein is advantageously replaced by a histidine.

Precise examples of this type of variants according to the invention are especially:

ScFv.antip53*-75-AS, described above, pEC143 (VP16-75-AS), comprising a deletion of the N-terminal part of the p53 protein comprising residues 1–74, substituted by the transactivating domain of VP16 of sequence SEQ ID No. 2; and a deletion of the C-terminal part, from residue 367, supplemented with the 19 amino acids of sequence SEQ ID No. 3. The complete sequence of the variant pEC143 is represented SEQ ID No. 28;

ScFv.antip53*-75-AS(H182), described above;

pEC153 (VP16-75-AS(H182)), corresponds to pEC143 with a histidine in position 182.

In a more general way, the invention relates to any chimeric protein comprising a transactivating domain, a DNA-binding domain, a domain for directing into the nucleus and an oligomerization domain, in which the domains for binding to DNA and for directing into the nucleus consist of amino acids 75 to 325 of the human wild-type p53 protein (SEQ ID No. 4). The applicant has indeed shown that this region of the p53 protein, coupled with appropriate transactivating and oligomerization domains, allows the creation of p53 type molecules having particularly advantageous properties in terms of stability, of resistance to the negative effects of the mutants of p53 and of sensitivity to inactivation by some cellular factors.

According to one variant, the domains for binding DNA and for directing into the nucleus consist of amino acids 75 to 336 of the human wild-type p53 protein (SEQ ID No. 5).

The chimeric proteins according to the invention may comprise various types of transactivating domains. This may be the transactivating domain of the p53 protein. Preferably, it is a heterologous transactivating domain, chosen for example from the transactivating domain of VP16 or a protein domain capable of specifically binding a transactivator or a transactivating complex present in a transformed cell.

As regards the oligomerization domain, this is preferably an artificial, and therefore a specific, domain such as for example an artificial leucine zipper, in particular of sequence SEQ ID No. 1.

The chimeric proteins according to the invention may, in addition, comprise a histidine residue in position 182.

Precise examples of chimeric proteins as described in the present application are especially pEC114, pEC116, pEC147 and pEC149.

The subject of the present invention is also any nucleic acid encoding a variant or a chimeric protein as defined above.

The nucleic acid according to the invention may be a ribonucleic acid (RNA) or a deoxyribonucleic acid (DNA). In addition, it may be a complementary DNA (cDNA) which may comprise one or more introns of the p53 gene. It may be of human, animal, viral, synthetic or semisynthetic origin. It may be obtained in various ways, and especially by chemical synthesis using the sequences presented in the application and for example a nucleic acid synthesizer. It may also be obtained by the screening of libraries by means of specific probes, especially as described in the application. It may also be obtained by a combination of techniques including the chemical modification (elongation, deletion, substitution and the like) of sequences screened from libraries. In general, the nucleic acids of the invention may be prepared according to any technique known to a person skilled in the art.

Preferably, the nucleic acid according to the invention is a cDNA or an RNA.

The nucleic acid according to the invention is advantageously chosen from:

(a) all or part of the sequences SED ID No. 25, 26, 27, 28, 29, 31, 32, 33 and 34 or of their complementary strand, (b) any sequence hybridizing with the (a) sequences and encoding a derivative according to the invention, (c) variants of (a) and (b) resulting from the degeneracy of the genetic code.

As indicated above, the applicant has now constructed new nucleic acid sequences encoding variant polypeptides of p53, having completely remarkable antiproliferative and apoptotic properties. These nucleic acids can be used as therapeutic agents to produce, in cells, derivatives according to the invention which are capable of destroying or of correcting cellular dysfunctions. To this end, the present invention also relates to any expression cassette comprising a nucleic acid as defined above, a promoter allowing its expression and a signal for termination of transcription. The promoter is advantageously chosen from promoters which are functional in mammalian, preferably human, cells. More preferably, this is a promoter allowing the expression of a nucleic acid in a hyperproliferative cell (cancerous, restenosis and the like). In this regard, various promoters can be used. This may be for example the promoter of the p53 gene itself. It may also be regions of different origin (which are responsible for the expression of other proteins, or which are even synthetic). It may thus be any promoter or derived sequence stimulating or repressing the transcription of a gene in a specific manner or otherwise, inducible or otherwise, strong or weak. There may be mentioned in particular the promoter sequences of eukaryotic or viral genes. For example, they may be promoter sequences derived from the genome of the target cell. Among the eukaryotic promoters, there may be used in particular ubiquitous promoters (promoter of the genes for HPRT, PGK, α-actin, tubulin and the like), of promoters of the intermediate filaments (promoter of the genes for GFAP, desmin, vimentin, neurofilaments, keratin and the like), promoters of therapeutic genes (for example the promoter of the genes for MDR, CFTR, Factor VIII, ApoAI, and the like), tissue-specific promoters (promoter of the gene for pyruvate kinase, villin, fatty acid-binding intestinal protein, smooth muscle α-actin and the like) or alternatively promoters responding to a stimulus (receptor for the steroid hormones, receptor for retinoic acid and the like). Likewise, there may be promoter sequences derived from the genome of a virus, such as for example the promoters of the adenovirus E1A and MLP genes, the CMV early promoter, or alternatively the RSV LTR promoter and the like. In addition, these promoter regions may be modified by addition of activation or regulatory sequences or of sequences allowing a tissue-specific or predominant expression.

The present invention now provides new therapeutic agents which make it possible, through their antiproliferative and/or apoptotic properties, to interfere with numerous cell dysfunctions. To this end, the nucleic acids or cassettes according to the invention may be injected as they are at the level of the site to be treated, or incubated directly with the cells to be destroyed or to be treated. It has indeed been described that naked nucleic acids could penetrate into cells without any special vector. Nevertheless, it is preferred, within the framework of the present invention, to use a vector for administration which makes it possible to improve (i) the efficiency of cell penetration, (ii) the targeting, and (iii) the extra and intracellular stability.

In a particularly preferred embodiment of the present invention, the nucleic acid or the cassette is incorporated into a vector. The vector used may be of chemical origin (liposome, nanoparticle, peptide complex, lipids or cationic polymers, and the like), or viral origin (retrovirus, adenovirus, herpes virus, AAV, vaccinia virus and the like) or of plasmid origin. The use of viral vectors rests on the natural transfection properties of viruses. It is thus possible to use, for example, adenoviruses, herpes viruses, retroviruses and adeno-associated viruses. These vectors are particularly efficient from the transfection standpoint. In this regard, a preferred subject according to the invention consists in a defective recombinant retrovirus whose genome comprises a nucleic acid as defined above. Another specific subject of the invention consists in a defective recombinant adenovirus whose genome comprises a nucleic acid as defined above.

The vector according to the invention may also be a nonviral agent capable of promoting the transfer and expression of nucleic acids in eukaryotic cells. Chemical or biochemical, synthetic or natural vectors represent an advantageous alternative to natural viruses in particular for reasons of convenience, safety and also by the absence of a theoretical limit as regards the size of the DNA to be transfected. These synthetic vectors have two principal functions, to compact the nucleic acid to be transfected and to promote its cellular attachment as well as its passage through the plasma membrane and, where appropriate, the two nuclear membranes. To overcome the polyanionic nature of nucleic acids, the nonviral vectors all possess polycationic charges.

The nucleic acid or vector used in the present invention may be formulated for topical, oral, parenteral, intranasal, intravenous, intramuscular, subcutaneous, intraocular and transdermal administration and the like. Preferably, the nucleic acid or vector is used in an injectable form. It may therefore be mixed with any vehicle, pharmaceutically acceptable for an injectable formulation, especially for a direct injection at the level of the site to be treated. This may be, in particular, sterile or isotonic solutions, or dry, especially freeze-dried, compositions which, upon addition, depending on the case, of sterilized water or of physiological saline, allow the preparation of injectable solutions. A direct injection of nucleic acid into the patient's tumour is advantageous because it makes it possible to concentrate the therapeutic effect at the level of the affected tissues. The doses of nucleic acid used may be adjusted according to various parameters, and especially according to the gene, vector, mode of administration used, pathology in question or alternatively the desired duration of treatment.

The invention also relates to any pharmaceutical composition comprising at least one nucleic acid as defined above.

It also relates to any pharmaceutical composition comprising at least one vector as defined above.

It also relates to any pharmaceutical composition comprising at least one variant of p53 as defined above.

Because of their antiproliferative properties, the pharmaceutical compositions according to the invention are most particularly suitable for the treatment of hyperproliferative disorders, such as especially cancers and restenosis. The present invention thus provides a particularly effective method for the destruction of cells, especially of hyperproliferative cells. It can be used in vivo or ex vivo. Ex vivo, it essentially consists in incubating the cells in the presence of one or more nucleic acids (or of a vector or cassette or directly of the derivative). In vivo, it consists in administering to the organism an active quantity of a vector (or of a cassette) according to the invention, preferably directly at the level of the site to be treated (tumour in particular). In this regard, the subject of the invention is also a method for destroying hyperproliferative cells comprising bringing the said cells or some of them into contact with a nucleic acid as defined above.

The present invention is advantageously used in vivo for the destruction of hyperproliferating cells (i.e. undergoing abnormal proliferation). It is thus applicable to the destruction of tumour cells or of the smooth muscle cells of the vascular wall (restenosis). It is most particularly appropriate for the treatment of cancers in which a mutant of p53 is observed. By way of example, there may be mentioned: colon adenocarcinomas, thyroid cancers, lung carcinomas, myeloid leukaemias, colorectal cancers, breast cancers, lung cancers, gastric cancers, oesophageal cancers, B lymphomas, ovarian cancers, cancers of the bladder, glioblastomas, hepatocarcinomas, cancers of the bones, skin, pancreas or alternatively cancers of the kidney and of the prostate, oesophageal cancers, cancers of the larynx, head or neck cancers, HPV-positive anogenital cancers, EBV-positive cancers of the nasopharynx, cancers in which the cellular protein mdm2 is overexpressed, and the like.

The variants of the invention are particularly effective for the treatment of cancers in which the MDM2 protein is, in addition, overexpressed, as well as cancers linked to the HPV virus, such as HPV-positive anogenital cancers.

The present invention is described in greater detail in the examples which follow, which should be considered as illustrative and nonlimiting.

LEGEND TO THE FIGURES

FIG. 1: Functional domains of the wild-type p53 protein. TA: transcription-activating domain; DNB: DNA-binding domain; NLS: nuclear localization signal; OL: oligomerization domain; REG: regulatory domain.

Figure 2:
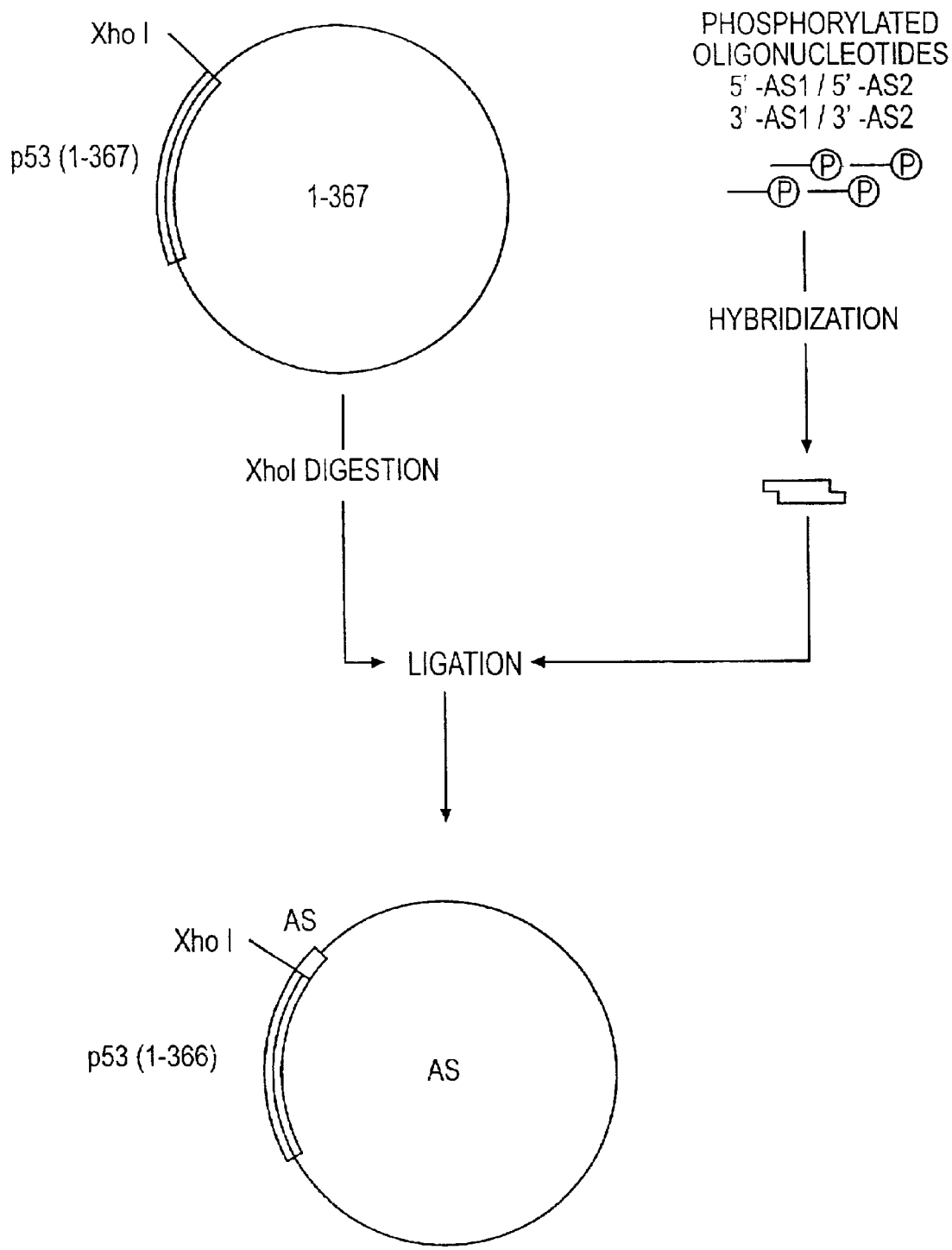

FIG. 2: Construction of a cDNA encoding the AS form of p53.

Figure 3:
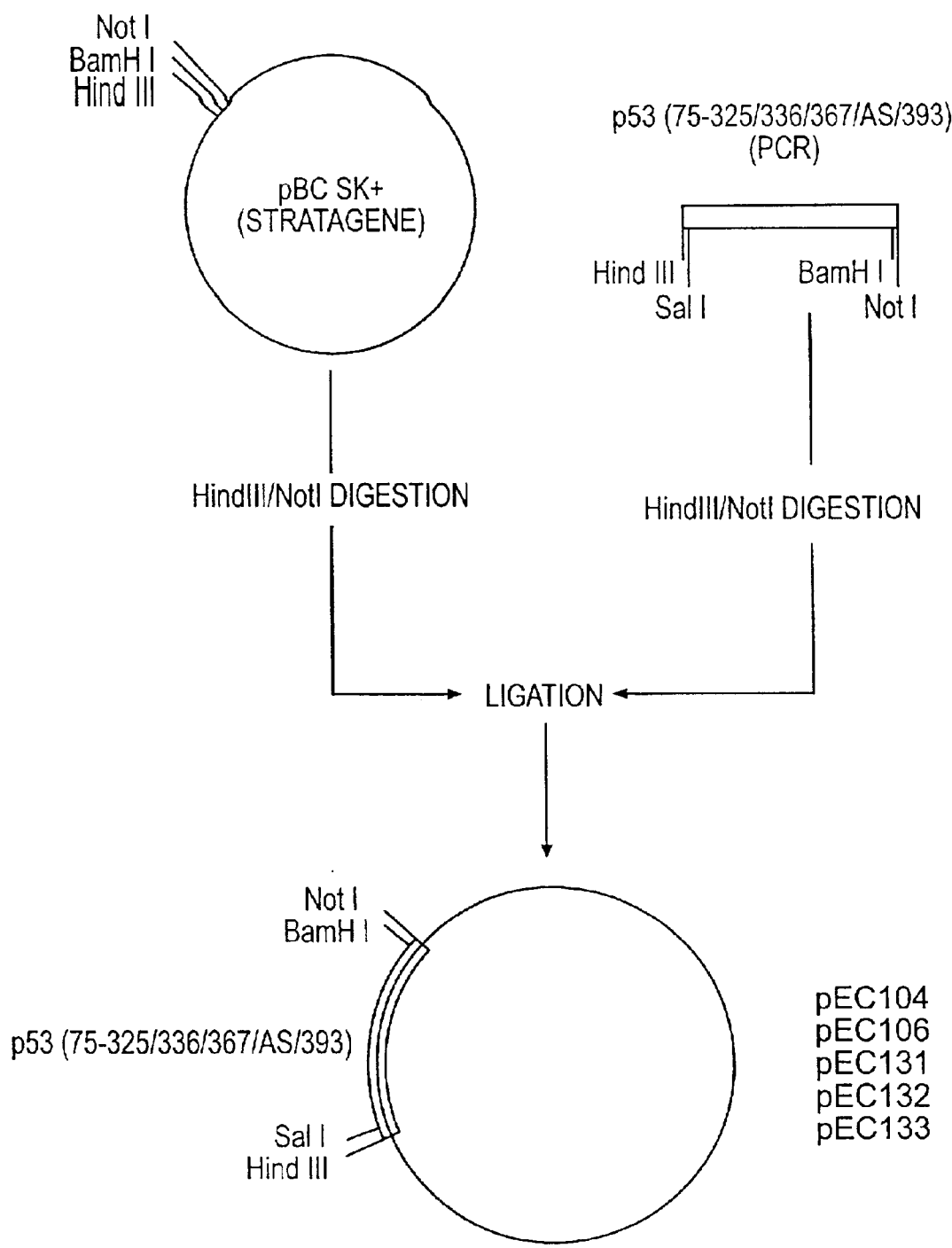

FIG. 3: Cloning of the cDNAs encoding the constructs pEC104, pEC106, pEC131, pEC132 and pEC133 and their variant H182.

Figure 4:
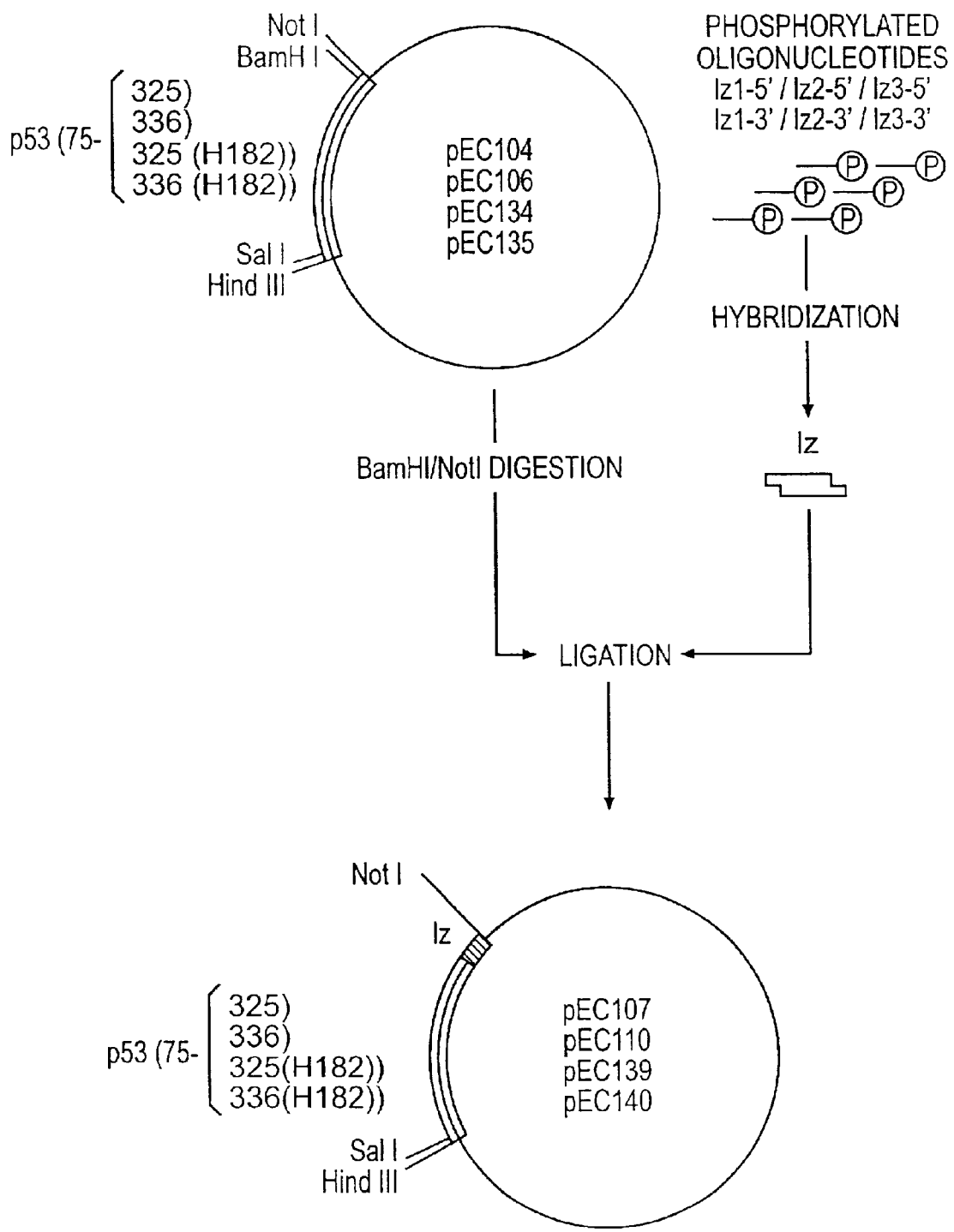

FIG. 4: Construction of the variants pEC107, pEC110, pEC139 and pEC140 by fusion with the artificial oligomerization domain.

Figure 5:
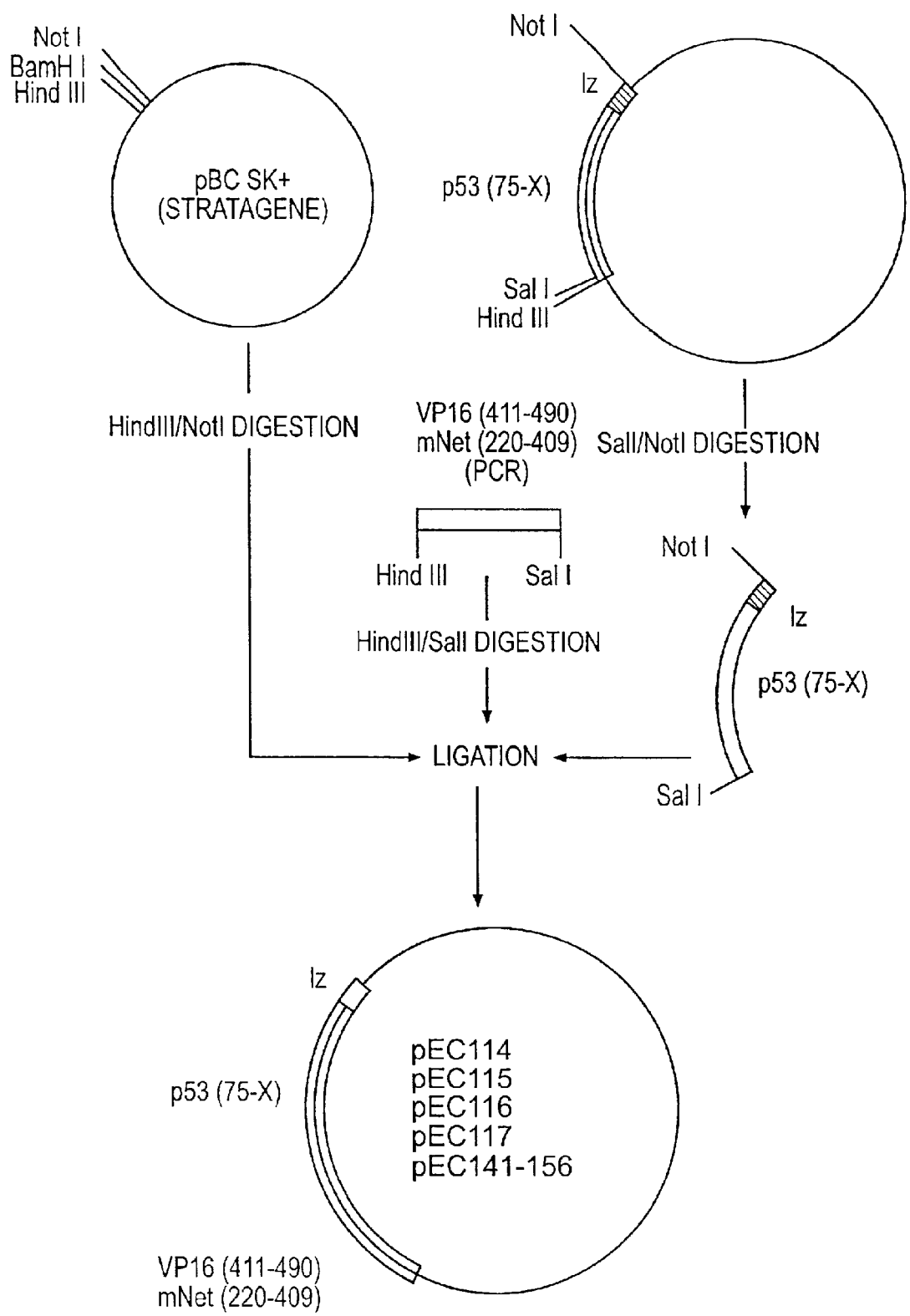

FIG. 5: Construction of the variants pEC114, pEC116, pEC141, pEC143, pEC145, pEC147, pEC149, pEC151, pEC153 and pEC155.

Figure 6:
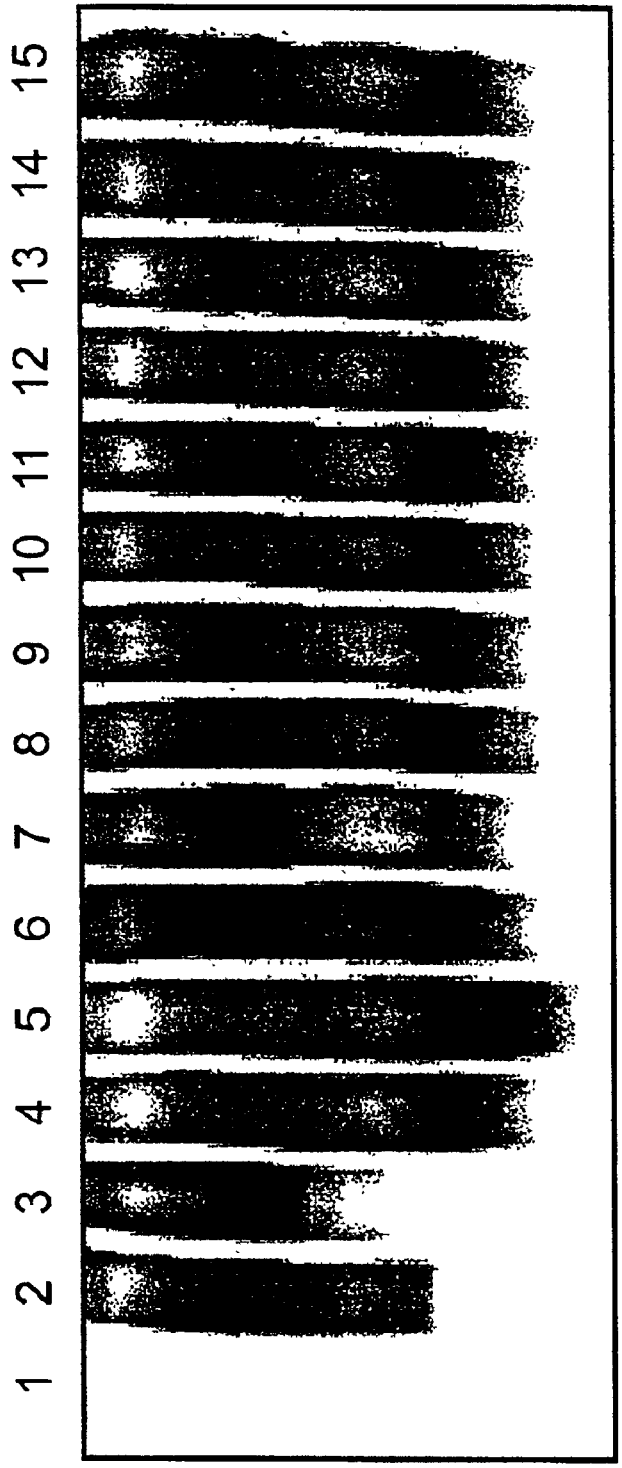

FIG. 6: Recognition of specific double-stranded DNA sequences by the hybrid molecules of the invention. Gel retardation experiment: competition between HisV325 and wild-type p53. column: 1 incubation in the absence of HisV325 and wild-type p53, column 2: 30 ng wild-type p53, column 3: as 2+pAb421, column 4: 30 ng HisV325, column 5: as 4+pAb421, column 6: 30 ng HisV325+30 ng wild-type p53, column 7: as 6+pAb421, column 8: 30 ng HisV325+15 ng wild-type p53, column 9: as 8+pAb421, column 10: 30 ng HisV325+7.5 ng wild-type p53, column 11: as 10+pAb421, column 12: 30 ng HisV325+4.5 ng wild-type p53, column 13: as 12+pAb421, column 14: 30 ng HisV325+3 ng wild-type p53, column 15: as 14+pAb421

Figure 7:
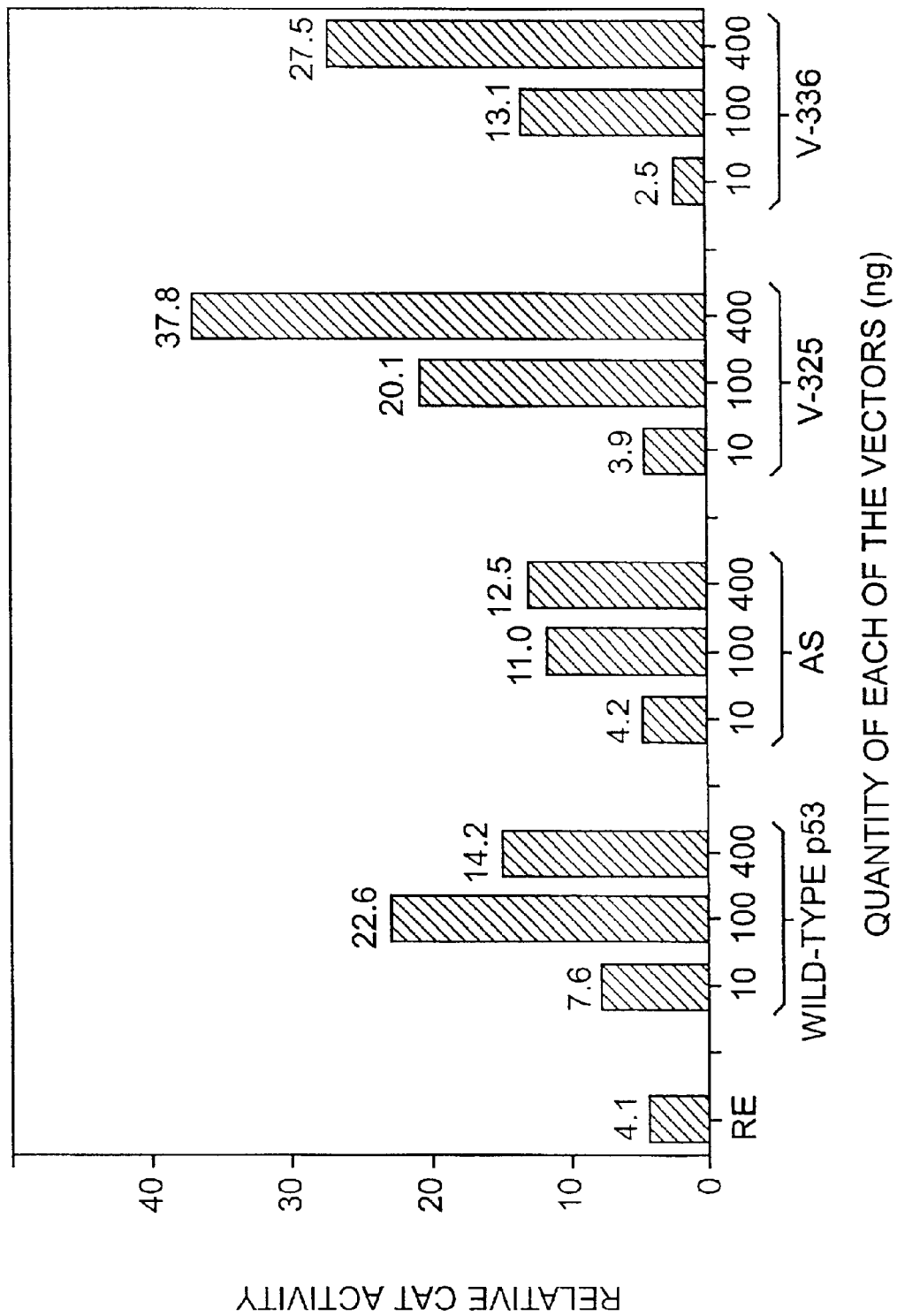

FIG. 7: Transactivating activity of the wild-type p53 protein and of the AS, V-325 and V-336 variants.

Figure 8:
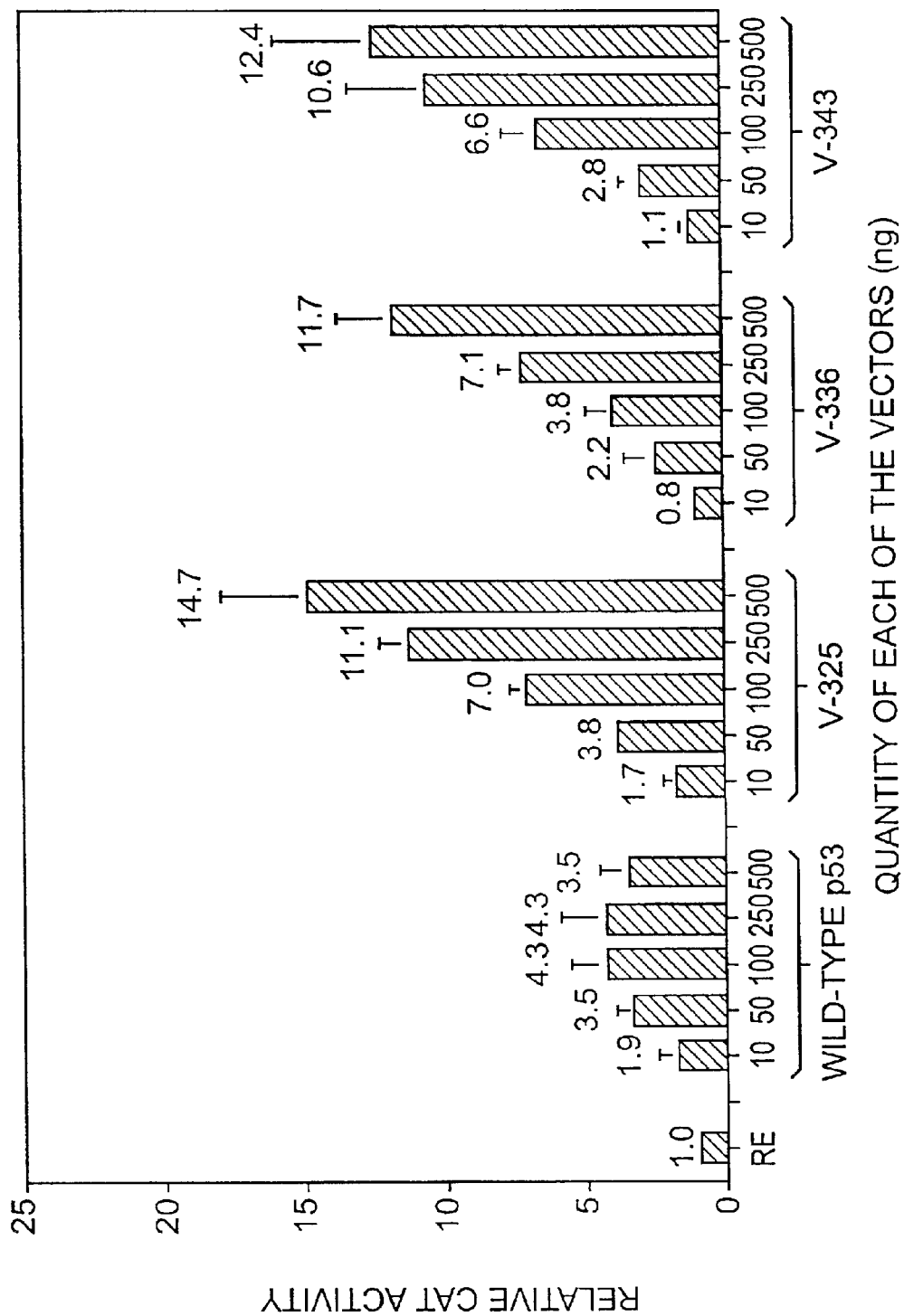

FIG. 8: Transactivating activity of the wild-type p53 protein and of the V-325, V-336 and V-343 variants.

Figure 9:
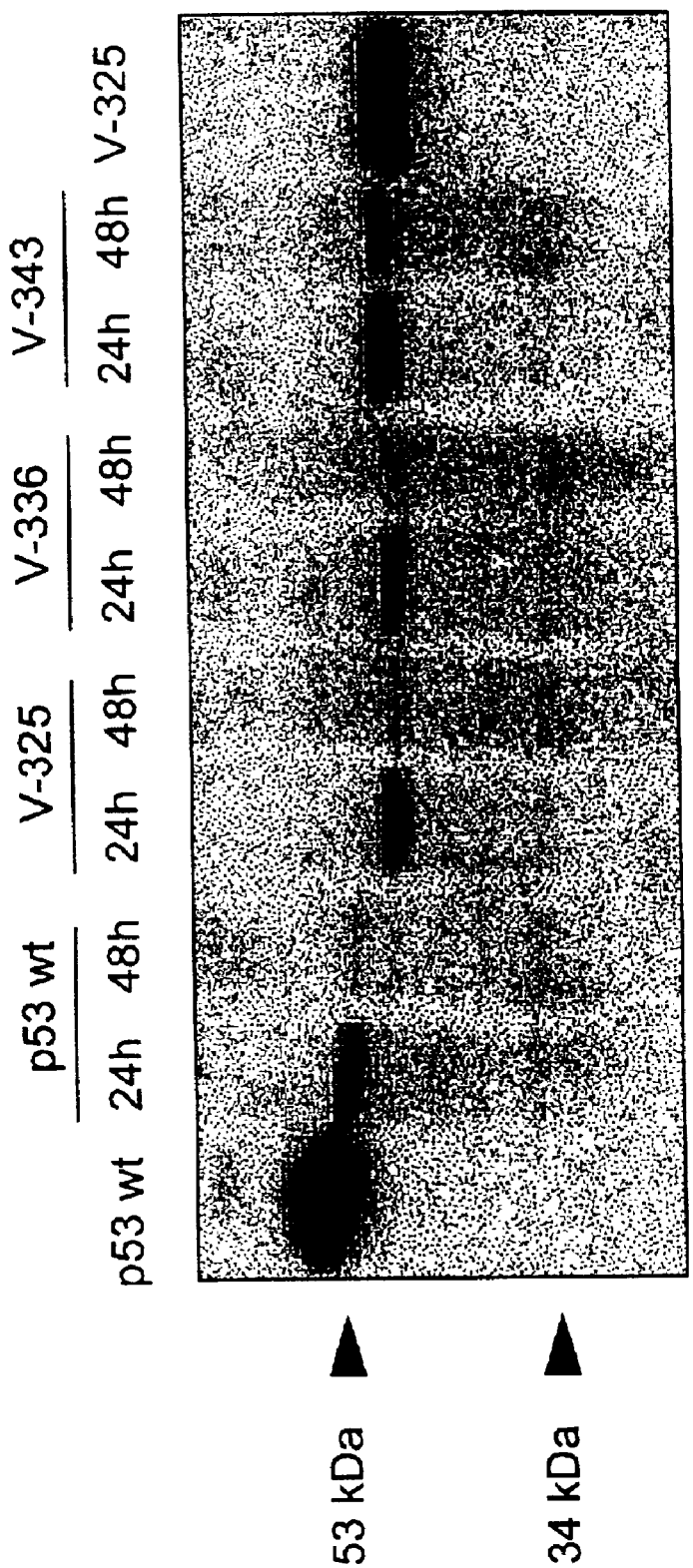

FIG. 9: Expression of the variants of the invention in SAOS-2 cells

Figure 10:
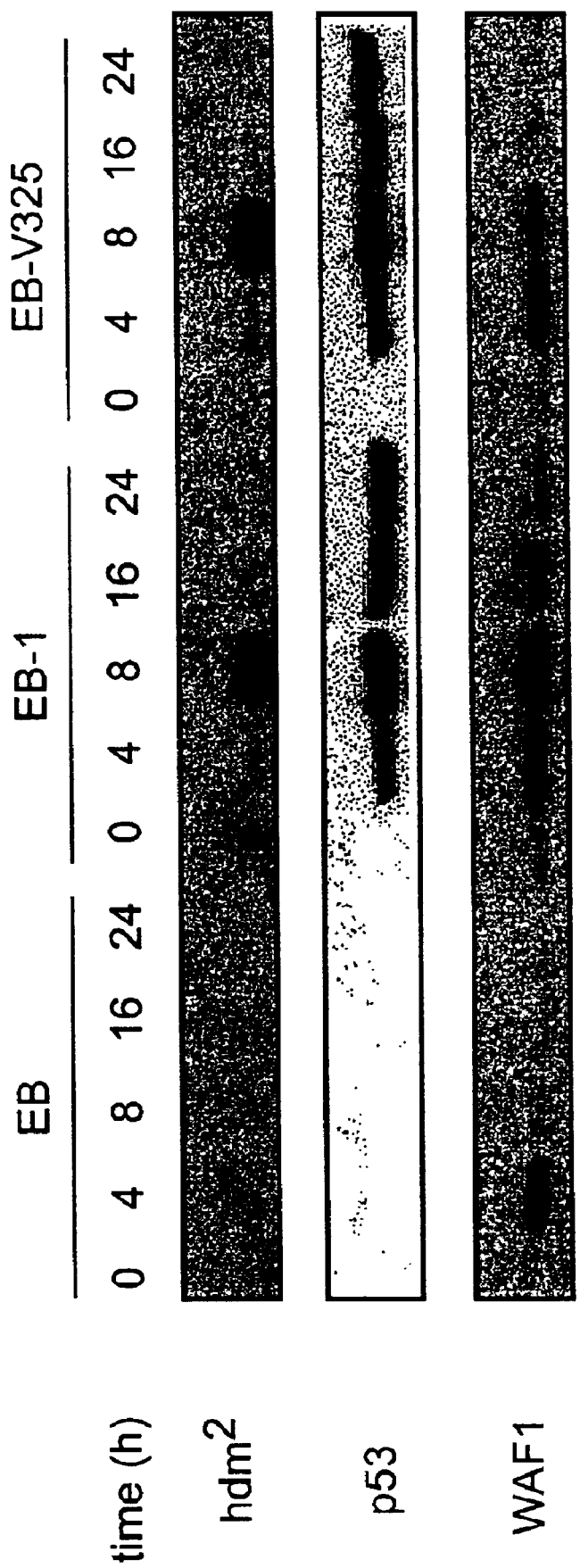

FIG. 10: Induction of the hdm2 and WAF1 genes in EB, EB-1 and EB-V325 cells

Figure 11:
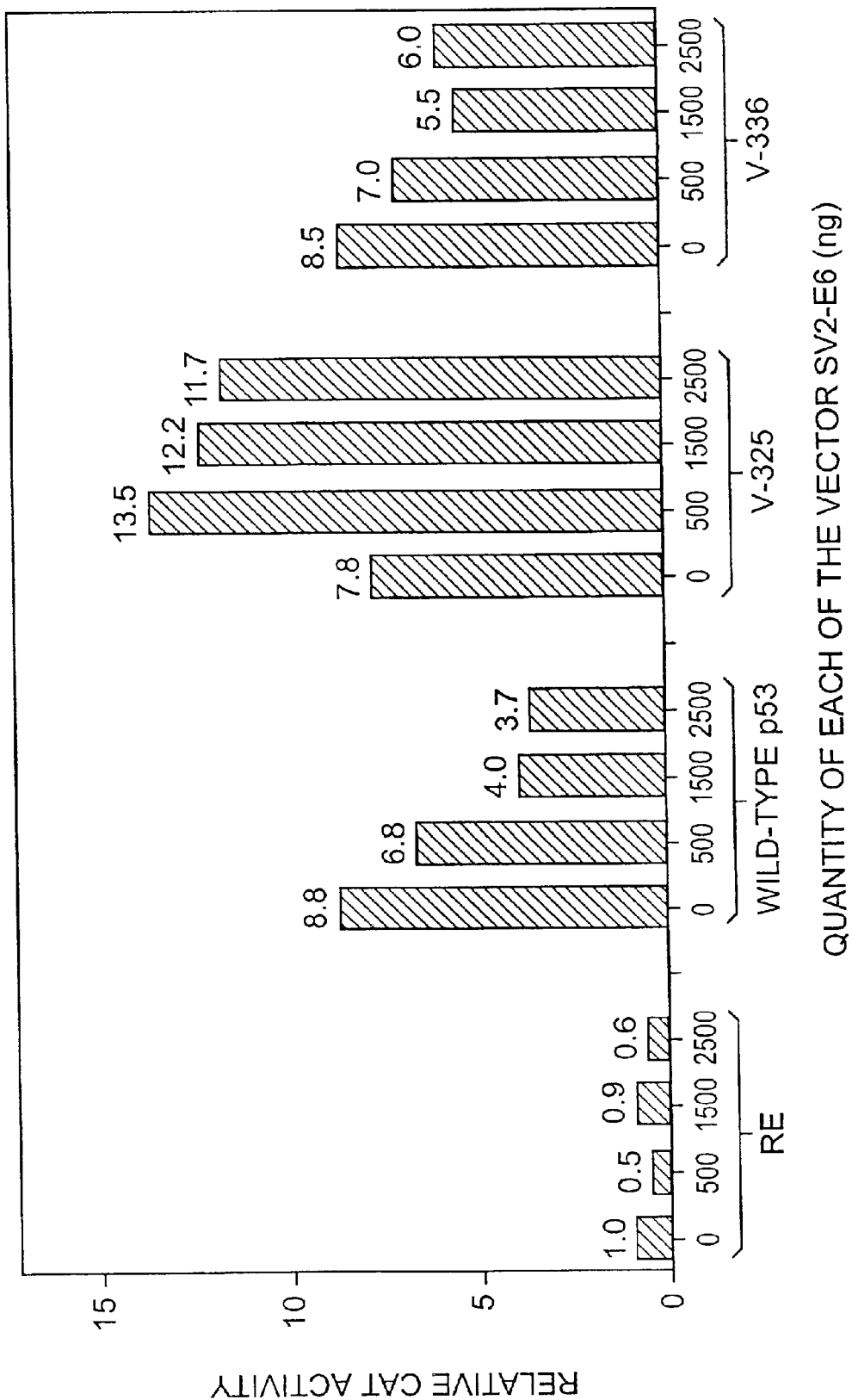

FIG. 11: Effect of the E6 protein on the transactivating function of the p53 protein and of the variants of the invention in SAOS-2 cells. Quantity of the vectors CMV-construct=100 ng FIG. 12: Effect of the E6 protein on the transactivating function of the p53 protein and of the variants of the invention in HeLa cells.

Figure 13A:
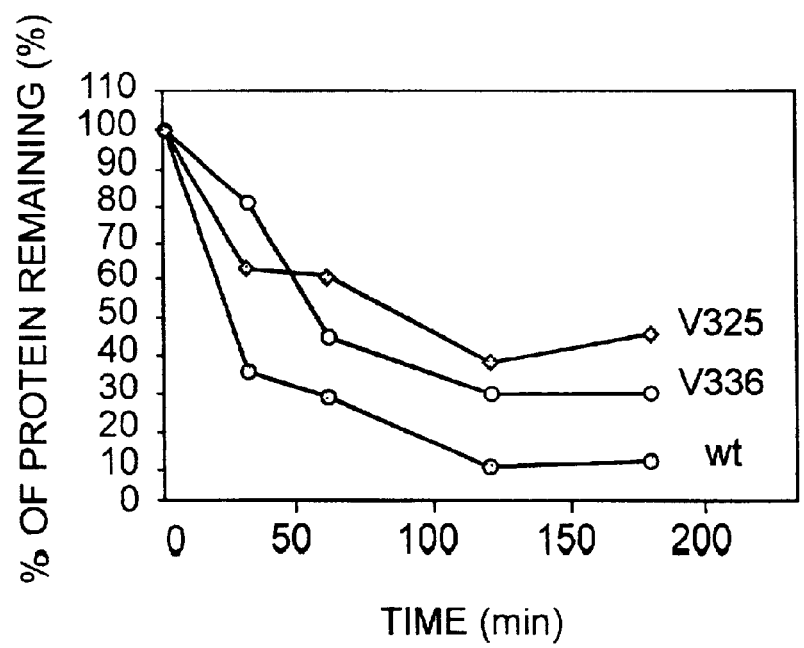
Figure 13B:
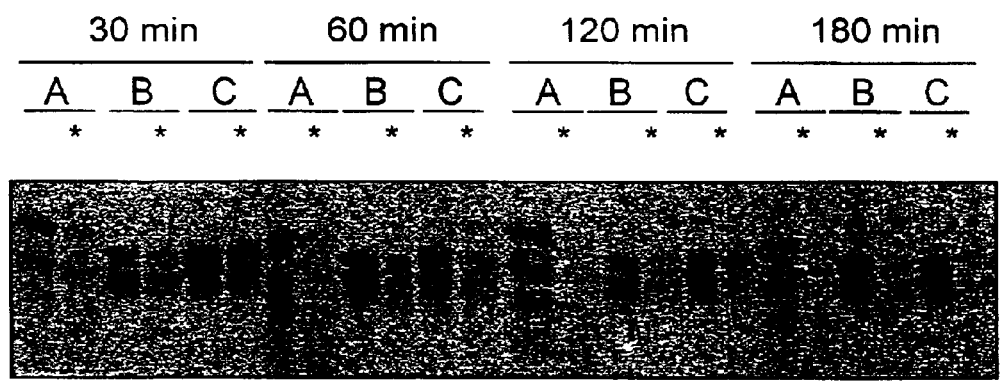

FIG. 13: Sensitivity of the wild-type p53 protein and of the variants of the invention to degradation induced by the E6 protein. Panel A shows the percentage of remaining wild-type and variant p53 proteins at various times in the presence of E6. Panel B shows a polyacrylamide gel electrophoresis analysis of the degradation of wild-type and variant p53 proteins at various times in the absence and presence of E6.

Figure 14:
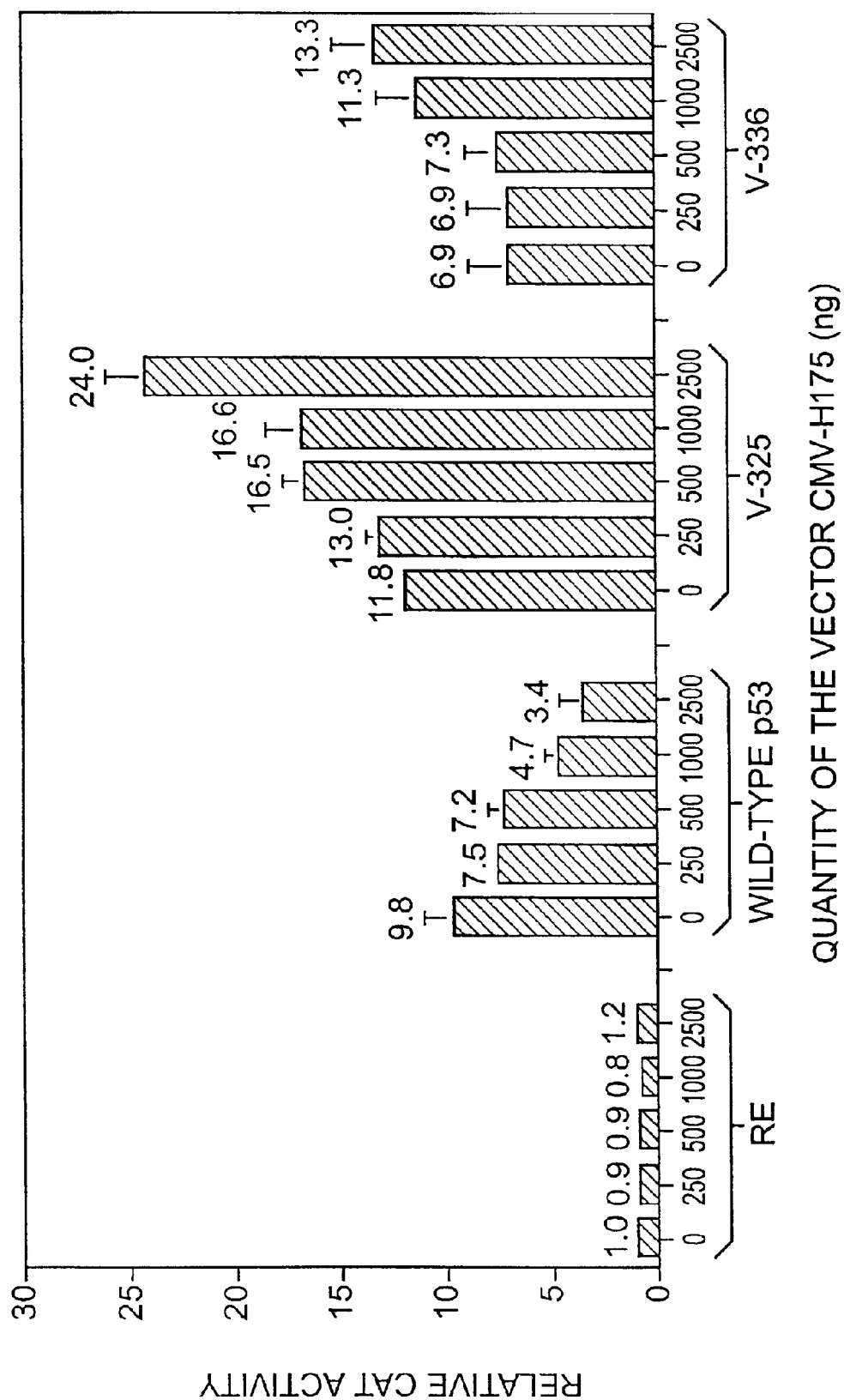

FIG. 14: Effect of the dominant-negative mutant of p53 H175 on the transactivating function of the variants of the invention. Quantity of the vectors CMV-construct=100 ng FIG. 15: Effect of the hdm2 protein on the transactivating function of the p53 protein and of the variants of the invention in SAOS-2 cells. Quantity of the vectors CMV-construct=100 ng FIG. 16: Effect of the wild-type p53 protein and of the V-325 protein on the growth of cells overexpressing the hdm2 protein.

Figure 17:
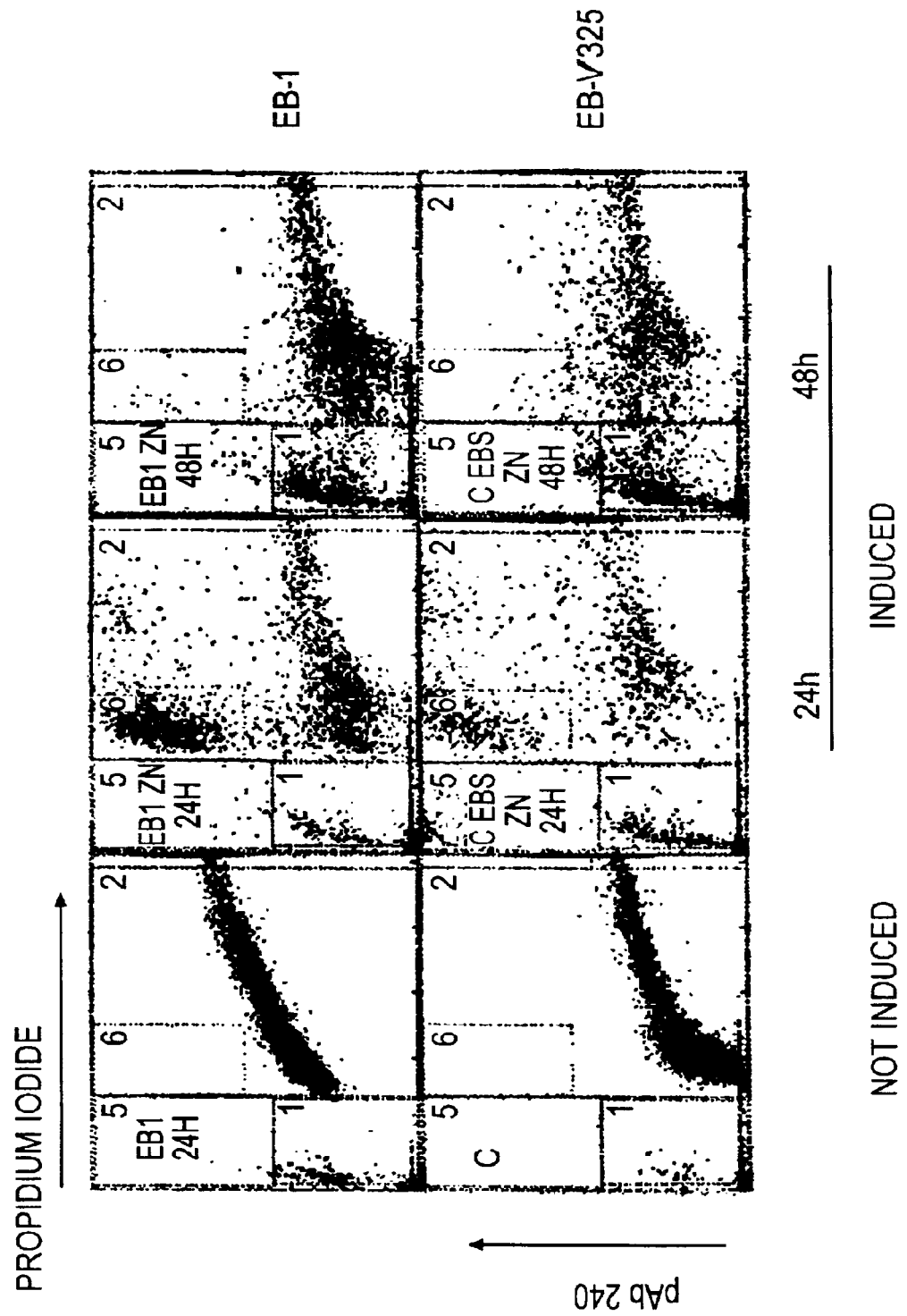

FIG. 17: Induction of apoptosis by the wild-type p53 protein and the V-325 protein.

Figure 18:
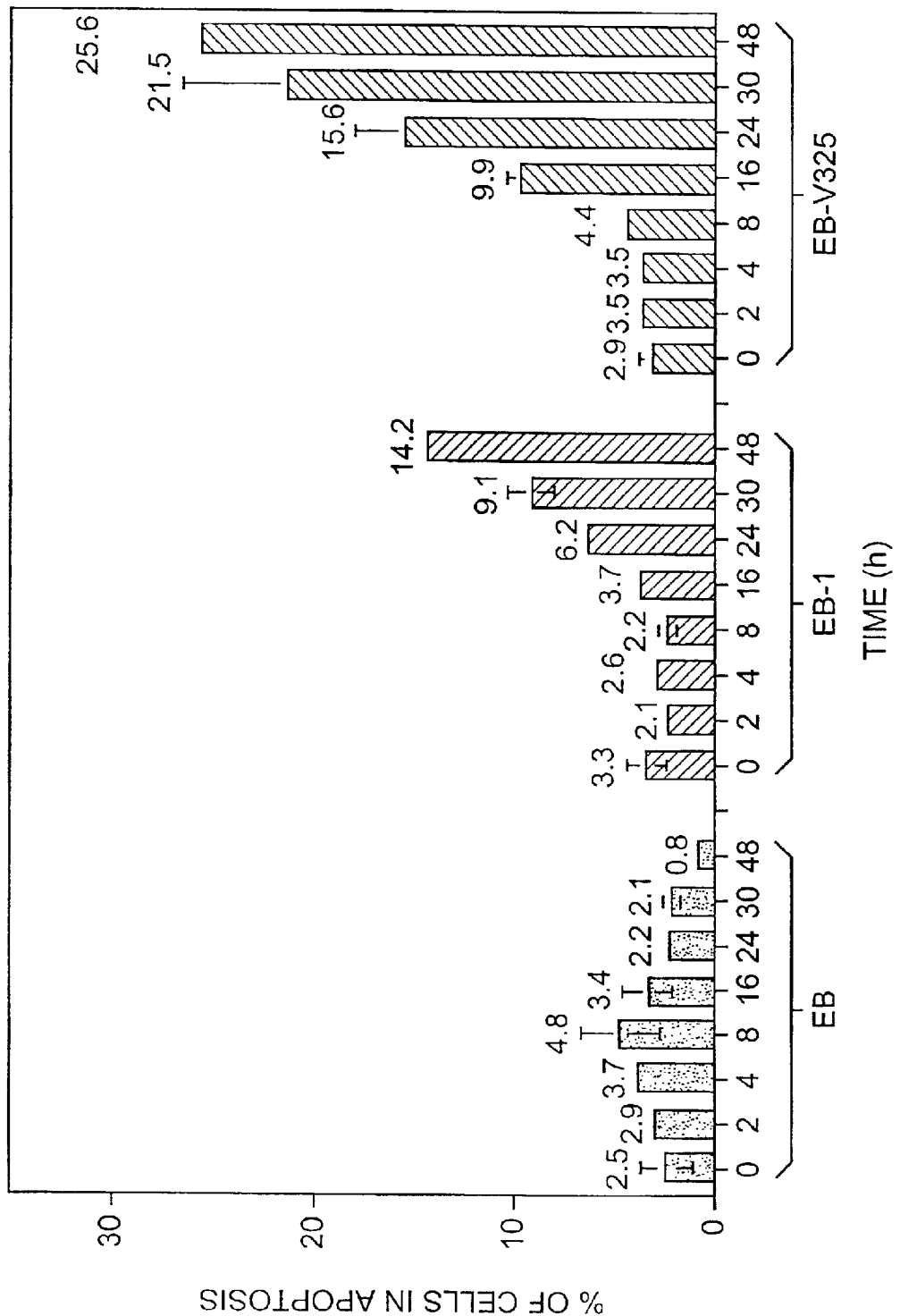

FIG. 18: Kinetics of induction of apoptosis in EB, EB-1 and EB-V325 cells

EXAMPLES

Example A

Construction of Various Nucleotide Fragments Necessary for Preparing the Genes Encoding the Variants of the p53 Protein A1. Construction of the cDNA Encoding the Human Wild-type p53.

The human p53 gene was cloned by polymerase chain reaction (PCR) on DNA from a human placenta library (Clontech) using the oligonucleotides 5'-1 and 3'-393.

```
Oligonucleotide 5'-1 (SEQ ID No. 6):
ATGGAGGAGCCGCAG

Oligonucleotide 3'-393 (SEQ ID No. 7):
GGCGGCCGCGATATCGATTCATCAGTCTGAGTCAGGCCCTTC
```

This product was then cloned directly after PCR into the vector pCRII (Invitrogene).

A2—Construction of a cDNA Encoding the As Form of p53

The AS form of p53 comprises a fragment encoding amino acids 1 to 366 of the human p53 protein supplemented with the last 19 amino acids of the alternative splicing product of the murine p53 protein.

The AS form of p53 was obtained in two stages:

PCR amplification of a fragment encoding amino acids 1 to 367 of the p53 protein using the oligonucleotides 5'-1 (cf. Example A1) and 3'-367.

```
Oligonucleotide 3'-367 (SEQ ID No. 8):
GGCGGCCGCGATATCGATTCATCAGCTCGAGTCAGC
```

The PCR fragment thus obtained was then cloned into the vector pCRII (Invitrogene). The fragment thus cloned has a recognition site for the restriction enzyme XhoI (fragment 1–367).

the oligonucleotides 5'-AS1, 5'-AS2, 3'-AS1 and 3'-AS2 were phosphorylated and then hybridized together in order to constitute the fragment encoding the last 19 amino acids of the alternative splicing product of the murine p53 protein.

```
5'-AS1 (SEQ ID No. 9):
TCGAGCCTGCAGCCTAGAGCCTTCCAAGCCCTCATGAAGGAGG

5'-AS2 (SEQ ID No. 10):
AAAGCCCAAACTGCTGATGAATCGATATCGC

3'-AS1 (SEQ ID No. 11):
TGAGGGCTTGGAAGGCTCTAGGCTGCAGGC

3'-AS2 (SEQ ID No. 12):
GGCCGCGATATCGATTCATCAGCAGTTTGGGCTTTCCTCCTTCA
```

This fragment was then inserted at the level of the XhoI site of fragment 1–367 (see FIG. 2). The gene thus constructed encodes the human variant of the alternative splicing product of the murine p53 protein (AS).

```
              364   367                            386           393
               I     I                              I             I
p53:-    A H S S H L K S K K G Q S T S R H K K L M F K T E G P D S D Z

AS:-     A H S S L Q P R A F Q A L M K E E S P N C Z Z

367:-    A H S S Z Z
```

A3—Construction of cDNA Encoding Various Fragments of the p53 Protein Carrying the DNA-binding Domain.

This example describes the construction of various cDNAs encoding various fragments of the human p53 protein, carrying all or part of the DNA binding domain of p53. These fragments are then used in the construction of the variants of p53. These fragments were obtained by polymerase chain reaction on the templates described in Examples A1 and A2 by means of various oligonucleotides. The amplification reactions were carried out under the conditions described in Example A4.1.

A3.1—Construction of a cDNA Encoding the 75–325 Region of p53 and its Derivative H182

This example describes the construction of a cDNA encoding amino acids 75 to 325 of the wild-type human p53 protein (75–325).

This cDNA was obtained by polymerase chain reaction (PCR) on the p53 DNA (described in Example A1) with the following oligonucleotides 5'-75 and 3'-325:

```
5'-75 (SEQ ID No. 13):
GGGAAGCTTGGGCCGGGTCGACCTGCACCAGCAGCTCCT

3'-325 (SEQ ID No. 14):
GGCGGCCGCGGATCCCCATCCAGTGGTTTCTT
```

A derivative of this fragment, carrying a point mutation on amino acid 182 of the human p53 protein (cysteine->Histidine), was obtained by site-directed mutagenesis by means of the Amersham kit, using the oligonucleotide H182 of sequence:

```
Oligonucleotide H182 3' (SEQ ID No. 15):
ATCTGAATGGCGCTC
```

This fragment was designated 75–325(H182).

A3.2—Construction of a cDNA Encoding the 75–336 Region of p53 and its Derivative H182

This example describes the construction of a cDNA encoding amino acids 75 to 336 of the wild-type human p53 protein (75–336).

This cDNA was obtained by polymerase chain reaction (PCR) on the p53 DNA (described in Example A1) with the oligonucleotides 5'-75 (SEQ ID No. 13) and 3'-336 below:

```
3'-336 (SEQ ID No. 16):
GGCGGCCGCGGATCCTCACGCCCACGGATCTG
```

A derivative of this fragment, carrying a point mutation on amino acid 182 of the human p53 protein (cysteine->Histidine), was obtained by site-directed mutagenesis by means of the Amersham kit, using the oligonucleotide H182 (SEQ ID No. 15). This fragment was designated 75–336 (H182).

A3.3—Construction of a cDNA Encoding the 75–343 Region of p53

This example describes the construction of a cDNA encoding amino acids 75 to 343 of the wild-type human p53 protein (75–343).

This cDNA was obtained by the polymerase chain reaction (PCR) on the DNA for p53 (described in Example A1) with oligonucleotides 5'-75 (SEQ ID No. 13) and 3'-343 which follows:

```
3'-343 (SEQ ID No. 45):
CGGATCCTCTCGGAACATCTCGAA
```

A3.4—Construction of a cDNA Encoding the 75–367 Region of p53 and its Derivative H182

This example describes the construction of a cDNA encoding amino acids 75 to 367 of the wild-type human p53 protein (75–367).

This fragment was obtained by polymerase chain reaction (PCR) on the p53 DNA described in Example A1 with the oligonucleotides 5'-75 (SEQ ID No. 13) and 3'-367 (SEQ ID No. 8).

The fragment thus obtained includes a recognition site for the endonuclease XhoI (75–367).

A derivative of this fragment, carrying a point mutation on amino acid 182 of the human p53 protein (cysteine->Histidine), was obtained by site-directed mutagenesis by means of the Amersham kit, using the oligonucleotide H182 (SEQ ID No. 15). This fragment was designated 75–367 (H182).

A3.5—Construction of a cDNA Encoding the 75-AS Fragment and its Derivative H182

This example describes the construction of a cDNA encoding amino acids 75 to 366 of the wild-type human p53 protein (75–366) supplemented with the last 19 amino acids of the alternative splicing product of the murine p53 protein.

This fragment was obtained by polymerase chain reaction (PCR) on the DNA of the AS fragment described in Example A2 with the oligonucleotides 5'-75 (SEQ ID No. 13) and 3'-AS2 (SEQ ID No. 12).

A derivative of this fragment, carrying a point mutation on amino acid 182 of the human p53 protein (cysteine->Histidine), was obtained by site-directed mutagenesis by means of the Amersham kit, using the oligonucleotide H182 (SEQ ID No. 15). This fragment was designated 75-AS (H182).

A3.6—Construction of a cDNA Encoding the 75–393 Fragment of p53 and its Derivative H182

This example describes the construction of a cDNA encoding amino acids 75 to 393 of the human p53 protein (75–393). This fragment was obtained by polymerase chain reaction (PCR) on the p53 DNA described in Example A1 with the oligonucleotides 5'-75 (SEQ ID No. 13) and 3'-393 (SEQ ID No. 7).

A derivative of this fragment, carrying a point mutation on amino acid 182 of the human p53 protein (cysteine->Histidine), was obtained by site-directed mutagenesis by means of the Amersham kit, using the oligonucleotide H182 (SEQ ID No. 15). This fragment was designated 75–393 (H182).

A4—Construction of cDNA Encoding Various Fragments Carrying a Transcription-activating Domain (Transactivating Domain).

This example describes the construction of various cDNA encoding various fragments carrying a transactivating domain. These fragments are then used in the construction of the variants of p53.

A4.1—PCR Reactions

The various fragments were obtained by polymerase chain reaction on various templates by means of various oligonucleotides. The amplification reactions were carried out under the following conditions: Amplitaq DNA polymerase enzyme (Perkin-Elmer) in the buffer provided by the supplier, with a dNTP concentration of 0.2 mM, 100 ng of template and 500 ng of each of the two oligonucleotides.

| | |
|---|---|
| cycle: | 2 min at 91° C. |
| cycles: | 1 min at 91° C. |
| | min at 55° C. |
| | min at 72° C. |
| cycle: | 5 min at 72° C. |

A4.2—Construction of a cDNA Encoding the 411–490 Region of the Viral Protein VP16 (VP16 TA)

This example describes the construction of a cDNA coding amino acids 411–490 of the viral protein VP16 (VP16 TA). This region carries the transactivating domain of this protein.

The transactivating fragment derived from the viral protein VP16 (411–490) of the herpes simplex virus was obtained by polymerase chain reaction (PCR) using the conditions defined above (cf. A4.1) and the following oligonucleotides 5'-VP16 and 3'-VP16:

```
5'-VP16 (SEQ ID No. 17):
AAGCTTGAATTCGTTAACATGTCCACGGCCCCCCCGACC

3'-VP16 (SEQ ID No. 18):
GGTCGACCACCGTACTCGTCAAT
``` and 100 ng of the plasmid pUHD15-1 (Gossen & Bujard, Proc. Natl. Acad. Sci. USA 89 (1992) 5547)

The fragment thus obtained comprises 334 base pairs whose sequence is represented SEQ ID No. 2. It comprises, in its N-terminal part, a methionine residue provided by the site for initiation of transcription (ATG), added during the PCR cloning step.

A4.2—Construction of cDNA Encoding Various Fragments Capable of Recruiting the Transcription Activating Domain (Transactivating Domain) of an Endogenous p53 Protein.

A4.2.1—Construction of a cDNA Encoding a Single-chain Antibody Capable of Binding the p53 Protein (ScFv 421)

This example describes the construction of a cDNA encoding a single-chain antibody capable of binding the p53 protein (ScFv 421). This construct, which is expressed at the intracellular level, should be capable of binding a wild-type or mutant endogenous p53 protein in order to recruit its transactivating domain.

The cDNA encoding ScFv 421 (Patent Application PCT/FR96/00477) can be extracted in the form of an NcoI/NotI fragment which comprises a site for initiation of translation (ATG) and no sequence for termination of translation.

The fragment thus obtained comprises 766 base pairs whose sequence is given SEQ ID No. 46.

A4.2.2—Construction of a cDNA Encoding the 325–360 Region of the Wild-type p53 Protein (325–360)

This example describes the construction of a cDNA encoding amino acids 325–360 of the wild-type p53 protein (325–360). This region carries the oligomerization domain of this protein. This construct, which is expressed at the intracellular level, should be capable of binding a wild-type or mutant endogenous p53 protein in order to recruit its transactivating domain.

This oligomerization domain, which is derived from the human wild-type p53 protein (325–360), was obtained by polymerase chain reaction (PCR) using the conditions defined above (Cf A4.1) and the Oiigonucleotides 5'-325 and 3'-360 which follow:

```
5'-325 (SEQ ID No. 47):
AAGCTTGAATTCGTTAACGCCACCATGGGAGAATATTTCACCCTT

3'-360 (SEQ ID No. 48):
GGGTCGACCTGGCTCCTTCCCAGC
``` on 100 ng of p53 DNA (described in Example A1).

The fragment thus obtained comprises 141 base pairs whose sequence is given SEQ ID No: 49. It comprises, in its N-terminal part, a methionine residue provided by the site for initiation of translation (ATG). added during the PCR cloning step and no sequence for termination of translation.

A4.2.3—Construction of a cDNA Encoding the 325–393 Region of the Wild-type p53 Protein (325–393)

This example describes the construction of a cDNA encoding amino acids 325–393 of the wild-type p53 protein (325–393). This region carries the oligomerization domain of this protein. This construct, which is expressed at the intracellular level, should be capable of binding a wild-type or mutant endogenous p53 protein in order to recruit its transactivating domain.

This oligomerization domain, which is derived from the human wild-type p53 protein (325–360), was obtained by polymerase chain reaction (PCR) using the conditions defined above (Cf A4.1) and the oligonucleotides 5'-325 (SEQ ID No. 47) and 3'-393.2 which follows:

```
3'-393.2 (SEQ ID No. 50):
GGGTCGACCGTCTGAGTCAGGCCCTTC
``` on 100 ng of the p53 DNA (described in Example A1).

The fragment thus obtained comprises 243 base pairs whose sequence is given SEQ ID No: 51. It comprises, in its N-terminal part, a methionine residue provided by the site for initiation of translation (ATG), added during the PCR doning step and no sequence for termination of translation.

A5—Construction of cDNA Encoding Various Fragments Carrying an Oligomerization Domain.

This example describes the construction of various cDNAs encoding various fragments carrying an oligomerization domain. These fragments are then used in the construction of the p53 variants. These fragments were obtained by polymerase chain reaction on various templates (p53 for the homologous domain and templates of various origins for the heterologous, especially artificial, oligomerization domains) by means of various oligonucleotides. The amplification reactions were carried out under the conditions described in A4.1 above.

A5.1—Construction of a cDNA Comprising an Artificial Oligomerization Domain.

This example describes the construction of a cDNA comprising an artificial oligomerization domain, consisting of an artificial leucine zipper. This cDNA was then used for the construction of variants from fragments 75–325 (Example A3.1) and 75–336 (Example A3.2) of the human p53 protein and of their derivatives modified at the level of the cysteine 182.

This cDNA was constructed from the following 6 oligonucleotides:

```
lz1-5' (SEQ ID No. 19)
GATCTGAAGGCCCTCAAGGAGAAGCTGAAGGCC lz2-5' (SEQ ID No. 20)
CTGGAGGAGAAGCTGAAGGCCCTGGAGGAGAAGCTG lz3-5' (SEQ ID No. 21)
AAGGCACTAGTGGGGGAGCGATGATGAATCGATATCGC lz1-3' (SEQ ID No. 22)
CTCCTCCAGGGCCTTCAGCTTCTCCTTGAGGGCCTTCA lz2-3' (SEQ ID No. 23)
TAGTGCCTTCAGCTTCTCCTCCAGGGCCTTCAGCTT lz3-3' (SEQ ID No. 24)
GGCCGCGATATCGATTCATCATCGCTCCCCCAC
```

These oligonucleotides were synthesized by means of an automatic DNA synthesizer, using the chemistry of phosphoramidites. These six oligonucleotides exhibit complementarity in pairs (lz1-5'/lz-1-3', lz2-5'/lz2-3', lz3-5'/lz3-3') and overlapping complementarities (lz1-3'/lz2-5', lz2-3'/lz3-5') which allow the oligomerization domain to be obtained simply by hybridization and ligation. The resulting LZ sequence is represented SEQ ID No. 1.

A5.2—Construction of a cDNA Comprising the Natural Oligomerization Domain of Human p53.

This example describes the construction of a cDNA comprising the natural oligomerization domain of human p53. This cDNA is represented by the fragment encoding amino acids 325 to 356 of p53 which is contained in the constructs 75–367 (Example A3.3), 75–AS (Example A3.4), 75–393 (Example A3.5) and of their derivatives modified at the level of the cysteine 182.

Example B

Construction of the Genes Encoding Various Variants of the p53 Protein

B1—Cloning of the Various Fragments of p53

Each of the various fragments obtained by PCR described in Example A was cloned after PCR into the vector pBC SK+ (Stratagene) using the recognition sites for the restriction enzymes HindIII and NotI (FIG. 3).

The products of these constructions carry the following numbers:

| | |
|---|---|
| 75-325 | --> pEC 104 |
| 75-336 | --> pEC 106 |
| 75-343 | --> pEC 171 |
| 75-367 | --> pEC 131 |
| 75-AS | --> pEC 132 |
| 75-393 | --> pEC 133 |

From these products and by site-directed mutagenesis using the oligonucleotide-directed in vitro mutagenesis system (Amersham) and the oligonucleotide H182, the corresponding constructs carrying a histidine in position 182 were obtained. These constructs carry the following numbers:

| | |
|---|---|
| 75-325(H182) | --> pEC 134 |
| 75-336(H182) | --> pEC 135 |
| 75-367(H182) | --> pEC 136 |
| 75-AS(H182) | --> pEC 137 |
| 75-393(H182) | --> pEC 138 |

B2—Fusion of the Leucine Zipper to Fragments 75–325, 75–336 and 75–343 and to their Variant H182

The oligonucleotides constituting the leucine zipper (lz1-5', lz1-3', lz2-5', lz2-3', lz3-5' and lz3-3') were phosphorylated with the aid of T4 kinase and they were all hybridized together and inserted into the vectors pEC 104, 106, 134, 135 and 171 previously digested with the restriction enzymes BamHI and NotI (FIG. 4).

The products of these constructions carry the following numbers:

| | |
|---|---|
| 75-325-lz | --> pEC 107 |
| 75-336-lz | --> pEC 110 |
| 75-343-lz | --> pEC 174 |
| 75-325(H182)-lz | --> pEC 139 |
| 75-336(H182)-lz | --> pEC 140 |

B3—Fusion of the Transcription-activating Domain to the Entire p53 Fragments

The final products were obtained by a three-partner ligation carried out in the following manner (FIG. 5):

The transcription-activating domain derived from VP16 which is described in Example A3 was prepared by enzymatic digestion of the PCR products with the restriction enzymes HindIII and SalI.

The various p53 fragments obtained above (75-325-lz, 75-336-lz, 75-343-lz, 75-AS, 75-367, 75-393 and their H182 variants) were isolated after enzymatic digestion of the plasmids containing them with the restriction enzymes SalI and NotI.

The possible combinations (activating domain/p53) were constituted and inserted simultaneously into the vector pBC SK+ (Stratagene) previously digested with the restriction enzymes HindIII and NotI.

The products of these constructions carry the following numbers:

| | | |
|---|---|---|
| VP16-75-325-lz | V-325 | --> pEC 114 (SEQ ID Nos. 25 and 26) |
| VP16-75-336-lz | V-336 | --> pEC 116 (SEQ ID Nos. 27 and 28) |
| VP16-75-367 | V-367 | --> pEC 141 (SEQ ID Nos. 29 and 30) |
| VP16-75-AS | V-AS | --> pEC 143 (SEQ ID Nos. 31 and 32) |
| VP16-75-393 | V-393 | --> pEC 145 (SEQ ID Nos. 33 and 34) |
| VP16-75-343 | V-343 | --> pEC 175 (SEQ ID Nos. 35 and 36) |
| VP16-75-325(H182)-lz | V-325H | --> pEC 147 |
| Vp16-75-336(H182)-lz | V-336H | --> pEC 149 |
| VP16-75-367(H182) | V-367H | --> pEC 152 |
| VP16-75-AS(H182) | V-ASH | --> pEC 153 |
| VP16-75-393(H182) | V-393H | --> pEC 155 |

The corresponding products, carrying a domain which specifically binds a transactivator or a transactivating complex in place of the VP16 domain, are constructed in the same manner. These constructs are designated below:

| | | |
|---|---|---|
| ScFv-75-325-lz | S-325 | --> pEC 176 (SEQ ID Nos. 37 and 38) |
| ScFv-75-336-lz | S-336 | |
| ScFv-75-367 | S-367 | |
| ScFv-75-AS | S-AS | |
| ScFv-75-393 | S-393 | |
| ScFv-75-325(H182)-lz | S-325H | |
| SeFv-75-336(H182)-lz | S-336H | |
| ScFv-75-367(H182) | S-367H | |
| ScFv-75-AS(H182) | S-ASH | |
| ScFv-75-393(H182) | S-393H | |
| (325-393)-75-325-lz | 393-325 | --> pEC 177 (SEQ ID Nos. 39 and 40) |
| (325-393)-75-367 | 393-367 | |
| (325-393)-75-AS | 393-AS | |
| (325-393)-75-393 | 393-393 | |
| (325-393)-75-325(H182)-lz | 393-325H | |
| (325-393)-75-336(H182)-lz | 393-336H | |
| (325-393)-75-367(H182) | 393-367H | |
| (325-393)-75-AS(H182) | 393-ASH | |
| (325-393)-75-393(H182) | 393-393H | |
| (325-360)-75-325-lz | 360-325 | --> pEC 178 (SEQ ID Nos. 41 and 42) |
| (325-360)-75-336-lz | 360-336 | |
| (325-360)-75-367 | 360-367 | |
| (325-360)-75-AS | 360-AS | |
| (325-360)-75-393 | 360-393 | |
| (325-360)-75-325(H182)-lz | 360-325H | |
| (325-360)-75-336(H182)-lz | 360-336H | |
| (325-360)-75-367(H182) | 360-367H | |
| (325-360)-75-AS(H182) | 360-ASH | |
| (325-360)-75-393(H182) | 360-393H | |

The products containing the 325–360 domain of p53, as a replacement for the transactivating domain (1–74) may be subject to the addition of a synthetic separator (Hinge) obtained by insertion, at the Sail site, of a DNA fragment obtained by hybridization of the pair of complementary synthetic oligonucleotides Hinge-up and Hinge-down which follow:

```
Hinge-up (SEQ ID No. 52):
TCGAGGAGGTGGTGGCTCTGGAGGCGGAGGATCCGGCGGTGGAGGTTC

Hinge-down (SEQ ID No. 53):
TCGAGAACCCCTACCGCCGGATCCTCCGCCTCCAGAGCCACCACCTCC
```

The resulting Hinge double-stranded DNA sequence is the following:

```
                                             (SEQ ID No. 52)
TCGAGGAGGTGGTGGCTCTGGAGGCGGAGGATCCGGCGGTGGAGGTTC

CCTCCACCACCGAGACCTCCGCCTCCTAGGCCGCCATCCCCAAGAGCT
``` and the corresponding protein sequence is

```
(SEQ ID No. 54):
Gly-Gly-Gly-Ser-Gly-Gly-Gly-Ser-Gly-Gly-Gly-Ser-
Gly-Gly-Gly-Ser
```

The corresponding products are designated below:

| | | |
|---|---|---|
| (325-360)-Hinge-75-325-lz | 360h-325 | --> pEC 179 (SEQ ID Nos. 43 and 44) |
| (325-360)-Hinge-75-336-lz | 360h-336 | |
| (325-360)-Hinge-75-367 | 360h-367 | |
| (325-360)-Hinge-75-AS | 360h-AS | |
| (325-360)-Hinge-75-393 | 360h-393 | |
| (325-360)-Hinge-75-325(H182)-lz | 360h-325h | |
| (325-360)-Hinge-75-336(H182)-lz | 360h-336H | |
| (325-360)-Hinge-75-367(H182) | 360h-367h | |
| (325-360)-Hinge-75-AS(H182) | 360h-ASH | |
| (325-360)-Hinge-75-393(H182) | 360h-393H | |

Example C

Construction of Expression Vectors for the Variants of p53

This example describes the construction of vectors which can be used for the transfer of the nucleic acids of the invention in vitro or in vivo.

C1—Construction of Plasmid Vectors

For the construction of plasmid vectors, 2 types of vectors were used.

The vector pSV2, described in DNA Cloning, A practical approach Vol. 2, D. M. Glover (Ed) IRL Press, Oxford, Washington D.C., 1985. This vector is a eukaryotic expression vector. The nucleic acids encoding the variants were inserted into this vector in the form of Hpal-EcoRV fragments. They are thus placed under the control of the promoter of the enhancer of the SV40 virus.

The vector pCDNA3 (Invitrogen). It is also a eukaryotic expression vector. The nucleic acids encoding the variants of the invention are thus placed, in this vector, under the control of the early CMV promoter. All the constructs described in Example B3 were introduced into this vector in the form of a HindIII/NotI fragment so as to be tested in the various systems for evaluation in vivo.

C2—Construction of Viral Vectors

According to a specific mode, the invention consists in the construction and the use of viral vectors which allow the transfer and the expression in vivo of the nucleic acids as defined above.

As regards more particularly adenoviruses, various serotypes, whose structure and properties vary somewhat, have been characterized. Among these serotypes, the use of the type 2 or 5 human adenoviruses (Ad 2 or Ad 5) or of the adenoviruses of animal origin (see application WO94/26914) is preferred within the framework of the present invention. Among the adenoviruses of animal origin which can be used within the framework of the present invention, there may be mentioned adenoviruses of canine, bovine, murine (example: MAV1, Beard et al., Virology 75 (1990) 81), ovine, porcine, avian or alternatively simian (example: SAV) origin. Preferably, the adenovirus of animal origin is a canine adenovirus, more preferably a CAV2 adenovirus [Manhattan strain or A26/61 (ATCC VR-800) for example]. Preferably, adenoviruses of human or canine or mixed origin are used within the framework of the invention.

Preferably, the defective adenoviruses of the invention comprise the ITRs, a sequence allowing the encapsidation and a nucleic acid according to the invention. Still more preferably, in the genome of the adenoviruses of the invention, at least the E1 region is nonfunctional. The viral gene considered can be rendered non-functional by any technique known to persons skilled in the art, and especially by total suppression, by substitution or partial deletion, or by addition of one or more bases in the gene(s) considered. Such modifications can be obtained in vitro (on the isolated DNA) or in situ, for example by means of genetic engineering techniques, or alternatively by treating with mutagenic agents. Other regions can also be modified, and especially the region E3 (WO95/02697), E2 (WO94/28938), E4 (WO94/28152, WO94/12649, WO95/02697) and L5 (WO95/02697). According to a preferred embodiment, the adenovirus according to the invention comprises a deletion in the E1 and E4 regions. According to another preferred embodiment, it comprises a deletion in the E1 region, at the level of which are inserted the E4 region and the nucleic acid of the invention (cf. FR94/13355). In the viruses of the invention, the deletion in the E1 region preferably extends from nucleotides 455 to 3329 on the sequence of the Ad5 adenovirus.

The defective recombinant adenoviruses according to the invention can be prepared by any technique known to persons skilled in the art (Levrero et al., Gene 101 (1991) 195, EP 185 573; Graham, EMBO J. 3 (1984) 2917). In particular, they can be prepared by homologous recombination between an adenovirus and a plasmid carrying, inter alia, the DNA sequence of interest. The homologous recombination occurs after co-transfection of the said adenoviruses and plasmid into an appropriate cell line. The cell line used should preferably (i) be transformable by the said elements, and (ii) contain the sequences capable of complementing the defective adenovirus genome part, preferably in integrated form in order to avoid risks of recombination. As an example of a cell line, there may be mentioned the human embryonic kidney line 293 (Graham et al., J. Gen. Virol. 36 (1977) 59) which contains especially, integrated in its genome, the left hand part of the genome of an Ad5 adenovirus (12%) or lines capable of complementing the E1 and E4 functions as described especially in applications Nos. WO 94/26914 and WO95/02697.

Next, the adenoviruses which have multiplied are recovered and purified according to conventional molecular biology techniques as illustrated in the examples.

As regards the adeno-associated viruses (AAV), they are relatively small DNA viruses which become integrated into the genome of the cells which they infect, in a stable and site-specific manner. They are capable of infecting a broad spectrum of cells, without inducing any effect on cell growth, morphology or differentiation. Moreover, they do not seem to be involved in pathologies in man. The genome of the AAVs has been cloned, sequenced and characterized. It comprises about 4700 bases and contains, at each end, an inverted repeat region (ITR) of about 145 bases which serves as replication origin for the virus. The remainder of the genome is divided into 2 essential regions carrying the encapsidation functions: the left-hand part of the genome, which contains the rep gene involved in the viral replication and the expression of the viral genes; the right-hand part of the genome, which contains the cap gene encoding the virus capsid proteins.

The use of vectors derived from AAVs for the transfer of genes in vitro and in vivo has been described in the literature (see especially WO 91/18088; WO 93/09239; U.S. Pat. No. 4,797,368, U.S. Pat. No. 5,139,941, EP 488 528). These applications describe various constructs derived from AAVs, from which the rep and/or cap genes are deleted and replaced by a gene of interest, and their use for the transfer in vitro (on cells in culture) or in vivo (directly in an organism) of the said gene of interest. The defective recombinant AAVs according to the invention can be prepared by co-transfection, into a cell line infected by a human helper virus (for example an adenovirus), of a plasmid containing a nucleic sequence of the invention of interest bordered by two AAV inverted repeat regions (ITR), and of a plasmid carrying the AAV encapsidation genes (rep and cap genes). An example of a cell line which can be used is line 293. The recombinant AAVs produced are then purified by conventional techniques.

As regards the herpesviruses and the retroviruses, the construction of recombinant vectors has been widely described in the literature: see especially Breakfield et al., New Biologist 3 (1991) 203; EP 453242, EP 178220, Bernstein et al. Genet. Eng. 7 (1985) 235; McCormick, BioTechnology 3 (1985) 689, and the like. In particular, the retroviruses are integrative viruses which selectively infect the dividing cells. They therefore constitute vectors of interest for cancer applications. The genome of retroviruses essentially comprises two LTRs, an encapsidation sequence and three coding regions (gag, pol and env). In the recombinant vectors derived from retroviruses, the gag, pol and env genes are generally deleted, completely or partly, and replaced by a heterologous nucleic acid sequence of interest. These vectors can be prepared from various types of retroviruses such as especially MoMuLV (murine Moloney leukaemia virus, also called MOMLV), MSV (murine Moloney sarcoma virus), HaSV (Harvey sarcoma virus), SNV (spleen necrosis virus), RSV (Rous sarcoma virus) or alternatively Friend's virus.

To construct the recombinant retroviruses according to the invention containing a nucleic acid according to the invention, a plasmid containing especially the LTRs, the encapsidation sequence and the said nucleic acid is constructed and then used to transfect a so-called encapsidation cell line capable of providing in trans the retroviral functions which are deficient in the plasmid. Generally, the encapsidation lines are therefore capable of expressing the gag, pol and env genes. Such encapsidation lines have been described in the prior art, and especially the PA317 line (U.S. Pat. No. 4,861,719), the PsiCRIP line (WO 90/02806) and the GP+envAm-12 line (WO 89/07150). Moreover, the recombinant retroviruses may contain modifications in the LTRs so as to suppress the transcriptional activity, as well as extended encapsidation sequences containing a portion of the gag gene (Bender et al., J. Virol. 61 (1987) 1639). The recombinant retroviruses produced are then purified by conventional techniques.

For the implementation of the present invention, it is most particularly advantageous to use a defective recombinant retrovirus or adenovirus. These vectors possess, indeed, properties which are particularly advantageous for the transfer of genes into tumour cells.

C3—Chemical Vectors

Among the synthetic vectors developed, it is preferred to use within the framework of the invention cationic polymers of the polylysine type (LKLK)n, (LKKL)n, polyethyleneimine type and DEAE dextran type or alternatively cationic lipids or lipofectants. They possess the property of condensing DNA and of promoting its association with the cell membrane. Among the latter, there may be mentioned lipopolyamines (lipofectamine, transfectam and the like), various cationic or neutral lipids (DOTMA, DOGS, DOPE and the like) as well as peptides of nuclear origin. In addition, the concept of targeted transfection was developed, mediated by a receptor, which takes advantage of the principle of condensing DNA by means of the cationic polymer while directing the attachment of the complex to the membrane by virtue of a chemical link between the cationic polymer and the ligand for a membrane receptor, present at the surface of the cell type which it is desired to graft. The targeting of the receptor for transferrin and for insulin or of the receptor for the asialoglycoproteins of the hepatocytes has thus been described. The preparation of a composition according to the invention using such a chemical vector is performed according to any technique known to persons skilled in the art, generally by simply bringing the various components into contact.

Example D

Functional Evaluation of the Variants of p53

The variants of p53 according to the invention were evaluated in a cellular test for the following criteria:
  binding to a specific double-stranded DNA sequence
  transactivating function
  antiproliferative activity
  apoptotic activity
  oncogenic potential associated with some p53 mutations The constructs used more particularly for this evaluation are the constructs V-325, V-336, V-343 and AS described in Example B.

D1 Recognition of Specific Double-stranded DNA Sequences by the Hybrid Molecules of the Invention D1.1 Production of the Hybrid Molecules The cDNA of the wild-type p53 was cloned into the vector pBlueBacIII (Invitrogen) at the BamHI site. By inserting into the plasmid pAcHLT-A (Pharmingen) the fragment containing the V325 cDNA obtained by digesting the plasmid pEC114 with the enzymes EcoRI and NotI, a vector was generated which allows the production of a recombinant baculovirus whose aim is the expression of a V325 protein tagged at the N-terminus with a peptide sequence containing, inter alia, a chain of 6 histidine residues. Using these vectors, recombinant baculoviruses were produced and purified according to the manufacturer's instructions (Invitrogen, Pharmingen). The two proteins were purified to homogeneity using nuclear extracts of SF9 insect cells infected with their respective baculoviruses, the nuclear extracts being obtained according to the procedure described by Delphin et al. (C. Delphin, Eur. J. Biochem., 223, 683–692, 1994).

The wild-type p53 is purified by immuno-affinity on the monoclonal antibody pAb421 (Oncogene Sciences, Ab-1) according to the following protocol: the nuclear extract of the infected cells is incubated for 3 h at 4° C. with a protein A-agarose gel onto which the antibody pAb421 has been covalently coupled. After extensive washing of the gel with a 50 mM Tris-HCl buffer pH 7.8, containing 1 M KCl and protease inhibitors, the p53 protein is eluted by the peptide corresponding to the epitope recognized by this antibody on p53 (KKGQSTSRHK), this peptide being used at a concentration of 5 mg/ml in the solution used for the washing. After concentration on Centricon-30 (Amicon Grace), the eluted p53 is separated from the peptide and purified to homogeneity by gel permeation on a Superose 6 HR10/30 column equilibrated with 50 mM Tris-HCl, pH 7.5, 0.2 M NaCl, 0.1 mM EGTA, 0.1 mM ZnCl$_2$, 10 mM DTT, 0.1 mM PMSF, 0.1% NP-40, 5% glycerol. The fractions containing p53 are aliquoted and immediately frozen at −80° C. until they are used.

The V325 protein, tagged at the N-terminals with a peptide sequence containing, inter alia, a chain of 6 histidine residues, henceforth called HisV325, was purified by a procedure adapted from Hochuli et al. (Bio/Technology Vol. 6 (1988) 1321). Before being applied to the Nickel-NTA agarose gel, the nuclear extract of the infected cells is desalted on a PD10 column (Pharmacia) equilibrated in 50 mM sodium phosphate buffer pH 8, containing 5 mM β-mercapto-ethanol, 0.1% NP-40 and a cocktail of protease inhibitors. The incubation of the nuclear extract with the nickel NTA agarose gel was carried out in this buffer for 1 h at 4° C., with stirring. The gel is then washed extensively with the same buffer at pH 6. The HisV325 protein is eluted with 0.3 M imidazole in the latter buffer after washing the gel in 0.1 M imidazole. The fractions containing HisV325 are aliquoted and immediately frozen at −80° C. until they are used.

D1.2 Construction of the Specific Doubled-stranded DNA Sequence

The specific double-stranded DNA sequence used in this experiment consists of two synthetic oligonucleotides whose sequences are the following:

```
Oligo 5568 (SEQ ID No. 55):
GATCCGAACATGTCCCAACATGTTGA

Oligo 5569 (SEQ ID No. 56):
AGCTTCAACATGTTGGGACATGGTTCG
```

These two synthetic oligonucleotides were labelled with phosphorus-33 by a 30-min incubation at 37° C. of 5 pmol of each oligonucleotide in 20 µl of the following reaction medium:

| | |
|---|---|
| Tris-HCl pH 7.6 | 50 mM |
| MgCl$_2$ | 10 mM |
| dithiothreitol | 5 mM |
| Spermidine | 100 µM |
| EDTA | 100 µM |
| [-γ-$^{33}$P]ATP (Amersham) | 50µ Ci (1000–3000 Ci/mmol) |
| T4 kinase (Boehringer) | 10 U |

Next, the two oligonucleotides thus labeled were hybridized in the presence of 100 mM NaCl in order to reconstitute the following double-stranded sequence WAF-Re containing the specific sequence recognized by p53 in the promoter region of the WAF-1 gene (W. S. El-Deiry, Cell Vol75 (1993) 817):

```
GATCCGAACATGTCCCAACATGTTGA        (SEQ ID No. 45)

GCTTGTACAGGGTTGTACAACTTCGA
```

D1.3 Recognition of the Double-stranded Sequence WAF-RE by the Hybrid Molecules of the Invention.

To demonstrate a specific recognition of the double-stranded sequence WAF-RE by the hybrid molecules of the invention, gel retardation experiments were carried out on the principle described below. The DNA binding reaction is carried out in 25 µl of reaction medium (20 mM Tris-HCl pH 7.5, 5 mM MgCl$_2$, 0.05 mM ZnCl$_2$, 5 mM dithiotreitol, 0.1 mg/ml BSA, 10% glycerol, 1% Nonidet P-40, 0.1 M NaCl, 2 µg/ml aprotinin, 2 µg/ml E-64, 2 µg/ml leupeptin, 2 µg/ml pepstatin) by adding the sequence WAF-RE ($2.4\times10^{-9}$ M) prepared according to the preceding example, $1.2\times10^{-6}$ M of the cold competitor oligonucleotide (Promega) used to eliminate nonspecific binding and 30 ng of hybrid molecules to be tested in the presence or otherwise of wild-type p53 (between 3 and 30 ng), it being possible for the wild-type p53 to be activated, for its specific DNA binding activity, by 300 ng of pAb421 antibody (T. R. Hupp, Cell Vol 71 (1992) 875). The reaction mixtures are incubated for 30 minutes on ice and the final mixtures are subjected to a 4% native polyacrylamide gel electrophoresis with migration at 200 V and 16° C. The gel is then dried and autoradiographed.

The result of a representative experiment of competition between wild-type p53 and HisV325 in gel retardation is presented in FIG. 6. This result shows that His-V325 recognizes the double-stranded sequence WAF-RE with a comparable affinity to that of the wild-type p53. It will be noted that HisV325 gives a predominant band in gel retardation which migrates faster than that obtained with the wild-type p53. This could indicate that HisV325 binds in the form of a dimer. Furthermore, as expected, this band is neither displaced nor amplified by the presence of pAb421. Finally, in the absence of pAb421, the wild-type p53 binds much less RE-WAF than does V325.

D2—Evaluation of the Transactivating Function

The transactivating function of the constructs was evaluated in a transactivating system in vivo in SAOS-2 (human osteosarcoma) cells deficient for the two alleles for the p53 protein (cells accessible at ATCC under the number HTB85) and in the tumour lines H358 (Maxwell & Roth, Oncogene 8 (1993), 3421) and HeLa (ATCC CCL 2). This system is based on the use of a reporter gene which can be assayed enzymatically and which is placed in dependence on a promoter containing the nucleotide units for specific recognition by the wild-type form of p53 (cf. experimental procedures).

In this test, the reporter gene is the CAT (chloramphenicol-acetyl transferase) gene and the sequence for recognition by p53 is the consensus sequence (p53RE) defined by Funk et al. (Mol. Cell. Biol. 12 (1992) 2866).

The evaluation of this function was carried out in comparison with that of the wild-type protein for three different types of criteria.

D2.1—Transactivating Activity in Response Dose

The cells ($3.5 \times 10^5$) are inoculated in Petri dishes 6 cm in diameter containing 3 ml of DMEM medium (Gibco BRL) supplemented with 10% heat-inactivated foetal calf serum, and they are cultured overnight in a $CO_2$ (5%) incubator at 37° C. The various constructs are then transfected using lipofectAMINE (Gibco BRL) as transfection agent in the following manner: 3 µg of total plasmid are incubated (of which 0.5 µg of the reporter plasmid) and 10 µl of lipofectAMINE for 30 min with 3 ml of Opti-MEM medium (Gibco BRL) without serum (transfection mixture). During this period, the cells are rinsed twice with PBS and then incubated for 4 hours at 37° C. with the transfection mixture, after which the latter is aspirated and replaced with 3 ml of DMEM medium supplemented with 10% heat-inactivated foetal calf serum and the cells allowed to grow again for 48 hours at 37° C.

Procedure for Assaying the CAT Activity 48 hours after transfection, the cells are washed once with PBS and then scraped and recovered in 100 µl of 0.25 M Tris buffer pH 8 and lysed by three freeze-thaw cycles in an ethanol/solid carbon dioxide bath. The total cellular extract thus obtained is centrifuged for 15 min at 10,000 rpm and the supernatant recovered for the assay of activity. The latter is carried out by adding 20 µl of cellular extract to 130 µl of a reaction mixture whose final composition is the following:

| | |
|---|---|
| Acetyl-coenzyme A | 0.4 mM |
| Chloramphenicol, D-threo-(dichloroacetyl-1,2-$^{14}$C) | 23 µM (200 nCi) |
| Tris | 0.18 M pH 8 |

After incubating for 1 hour at 37° C., the reaction products are extracted with 250 µl of ethyl acetate, of which 20 µl are placed on a silica plate (thin-layer chromatography) which is allowed to run in a mixture containing 95% chloroform and 5% methanol. The chromatography plate thus obtained is finally developed using an instant imager (Packard instruments) which makes it possible to calculate the ratio of the various products of acetylation, which ratio reflects the activity of the enzyme chloramphenicol acetyl-transferase and therefore the transactivating activity of the various constructs.

The results obtained in the SAOS-2 line with the constructs placed under the control of the CMV promoter (pCDNA3) and presented in FIGS. 7 and 8 show the following properties for each of the constructs:

the p53 protein has a dose-dependent activity which tends towards saturation for high doses (from 100 ng of plasmid). This saturation may reflect the need for cofactors which could be limiting under these conditions.

the AS protein conserves the transcription-activating capacity of the wild-type protein.

the V-325, V-336 and V-343 proteins have, just like the p53 protein, a transactivating activity which does not appear, for its part, saturable at high doses. It is therefore possible that this apparent lack of saturation may lead to an overall increase in activity. It appears, in addition, that the construct V-325 is more active than its homologues V-336 and V-343, which suggests that the chimeric proteins carrying the 75–325 region are particularly advantageous.

With the aim of confirming these properties, a similar experiment was carried out in the tumour line H 358 which, just like the SAOS-2 line, is deficient for the two alleles of the p53 gene. In this experiment, each transfection was carried out with 50 ng of each of the constructs placed in dependence on the CMV promoter. The results presented in Table 1 show clearly that the two variants V-325 and V-336 show an improved transactivating activity compared with that of the wild-type p53 protein, with again a better activity for the variant V-325.

TABLE 1

| | Transactivating activity in the cells of the tumour line H 358. | | | |
|---|---|---|---|---|
| | pCDNA 3 | wild-type p53 | V-325 | V-336 |
| Relative CAT activity | 1 | 6 | 25 | 16 |

These two tests confirm that the variants of the invention have at least one of the properties of the improved p53.

In order to verify that this difference in activity is not due to a difference in expression, but indeed to an increased activity of the variants of the invention, the level of expression of the wild-type p53 protein and of the variants V-325, V-336 and V-343 was analysed in SAOS-2 cells. To do this, the cells are transfected with 3 µg of each of the plasmids used in the preceding experiment, and recovered 24 hours and 48 hours after transfection. After two washes in PBS buffer (Gibco BRL), the cells are lysed for 15 minutes at 4° C. in 50 µl of RIPA buffer (10 mM Tris-Hcl pH 8.0, 150 mM NaCl, 1 mM EDTA, 1% Nonidet-P40, 1% sodium deoxycholate, 0.1% sodium dodecyl sulphate) supplemented with 2 mM PMSF, 20 µg/ml aprotinin, 2 µg/ml E64, 2 µg/ml leupeptin and 2 µg/ml pepstatin. After 15 min of centrifugation at 15,000 rpm, the supernatants are collected, supplemented with migration buffer (Laemmli U. K., Nature, 227, 680–685, 1970) and subjected to electrophoresis on a 10% polyacrylamide gel in denaturing medium at 200 V according to the protocol previously described (Laemmli U. K., Nature, 227, 680–685, 1970). Next, the proteins are transferred onto PVDF membrane (NEN Research Products) using the NOVEX semidry transfer system according to the manufacturer's recommendations, and revealed with the aid of the monoclonal antibody pAb 240 (Oncogene Sciences, Ab-3) and of a secondary antibody (anti-mouse rabbit antibody) coupled to peroxidase (Nordic Immunology) using the ECL kit (Amersham).

The result of this experiment which is presented in FIG. 9 shows that the variants V-325 and V-336 are expressed at a comparable level to that of the wild-type p53 protein and that the variant V-343 appears to be slightly better expressed than the previous ones. Furthermore, comparison of the expression levels at 24 and 48 hours appears to indicate that the relative stability of each of the constructs is similar. This result therefore shows that the increased activity of the variants of the invention V-325 and V-336 is not due to a better expression but probably to an increased transcriptional activating potential, contrary to the V-343 variant.

Subsequently, and with the aim of confirming this capacity of the variants of the invention to activate a gene placed under the control of a wild-type p53 recognition element, the study of the activation of endogenous genes was carried out by looking at the expression of the hdm2 and WAF1 genes, which are normally induced by the p53 protein.

This experiment was carried out in the EB cell line (colon cancer) deficient for the two alleles encoding the p53 protein (Shaw et al., PNAS 89 (1992) 4495). A stable clone expressing the p53 protein under the control of the inducible metallothionein promoter was constructed from this line (clone EB-1 (Shaw et al., PNAS 89 (1992) 4495)). Likewise, another stable clone expressing the V-325 protein under the control of the inducible metallothionein promoter was constructed using a plasmid derived from the vector pmIMT1i (obtained from P. Shaw) by insertion of the cDNA encoding the V-325 protein at the EcoRI-NotI sites (pmIMT1i-V325). To do this, the EB cells ($3.5 \times 10^5$ cells) were transfected with 1.3 $\mu$g of the plasmid pmIMT1i-V325 and 200 ng of plasmid pcDNA3 following the procedure described above and the stable clones were selected after transfection by growing in a medium containing 800 $\mu$g/ml of geneticin. A clone expressing V-325 in an inducible manner at a level comparable to the expression of the p53 protein in the EB-1 clone was selected (EB-V325 clone).

The EB-1 and EB-V325 clones as well as the EB parental cells ($10^6$ cells) were subjected to treatment with $ZnCl_2$ (200 $\mu$M) and cell extracts were prepared at various times and subjected to electrophoresis and membrane transfer as described above. The transferred proteins were revealed by three different antibodies; the monoclonal antibody pAb240 directed against the p53 protein, and two polyclonal antibodies, one directed against the hdm2 protein and the other against the WAF1 protein. The results of this experiment, presented in FIG. 10, show that: 1) the p53 protein, absent from the EB, EB-V325 and EB-1 cells in the absence of induction, is expressed in the EB-1 clone as early as 4 hours after the start of the zinc treatment, and the variant V-325 is expressed in the same manner in the EB-V325 clone, 2) the WAF1 protein whose expression appears to be induced in the EB cells by the zinc, treatment 4 hours after starting it, sees its expression prolonged up to 16 hours in the EB-1 and EB-V325 clones, and 3) the induction of the hdm2 protein is observable only in the EB-1 and EB-V325 clones, with an increased expression in the EB-V325 clone.

These results show that the activation of transcription by the V-325 variant results in the induction of the expression of genes normally induced by the wild-type p53 protein, and that this variant indeed exhibits an increased activity in a physiological context relative to the wild-type p53 protein.

D2.2—Effect of the E6 Protein (HPV18) on the Transactivating Function

The procedures used are identical to those described in Example D1.1. In this transfection experiment, the constructs placed under the control of the CMV promoter (pCDNA3) were cotransfected with increasing concentration of a plasmid expressing E6 under the control of the SV40 promoter (pSV2). The results obtained in the SAOS-2 line and presented in FIG. 11 show the following properties for each of the constructs:

the activity of p53 decreases as the concentration of E6 is increased, this decrease being quite probably a reflection of the degradation of p53 induced by E6;

the protein V-336 exhibits a lack of sensitivity to E6;

the protein V-325 appears to be capable of being slightly activated by E6. The protein V-325 is always, and in all the situations observed, more active than p53. To confirm this difference in behaviour towards the protein E6, the transactivating activity of the constructs V-325 and V-336 in HPV18-positive cells (HeLa), which therefore express the protein E6, was tested and compared with that of the wild-type p53.

In this transfection experiment carried out according to the procedure described above, the various constructs were placed under the control of the CMV promoter (pCDNA3).

Figure 12:
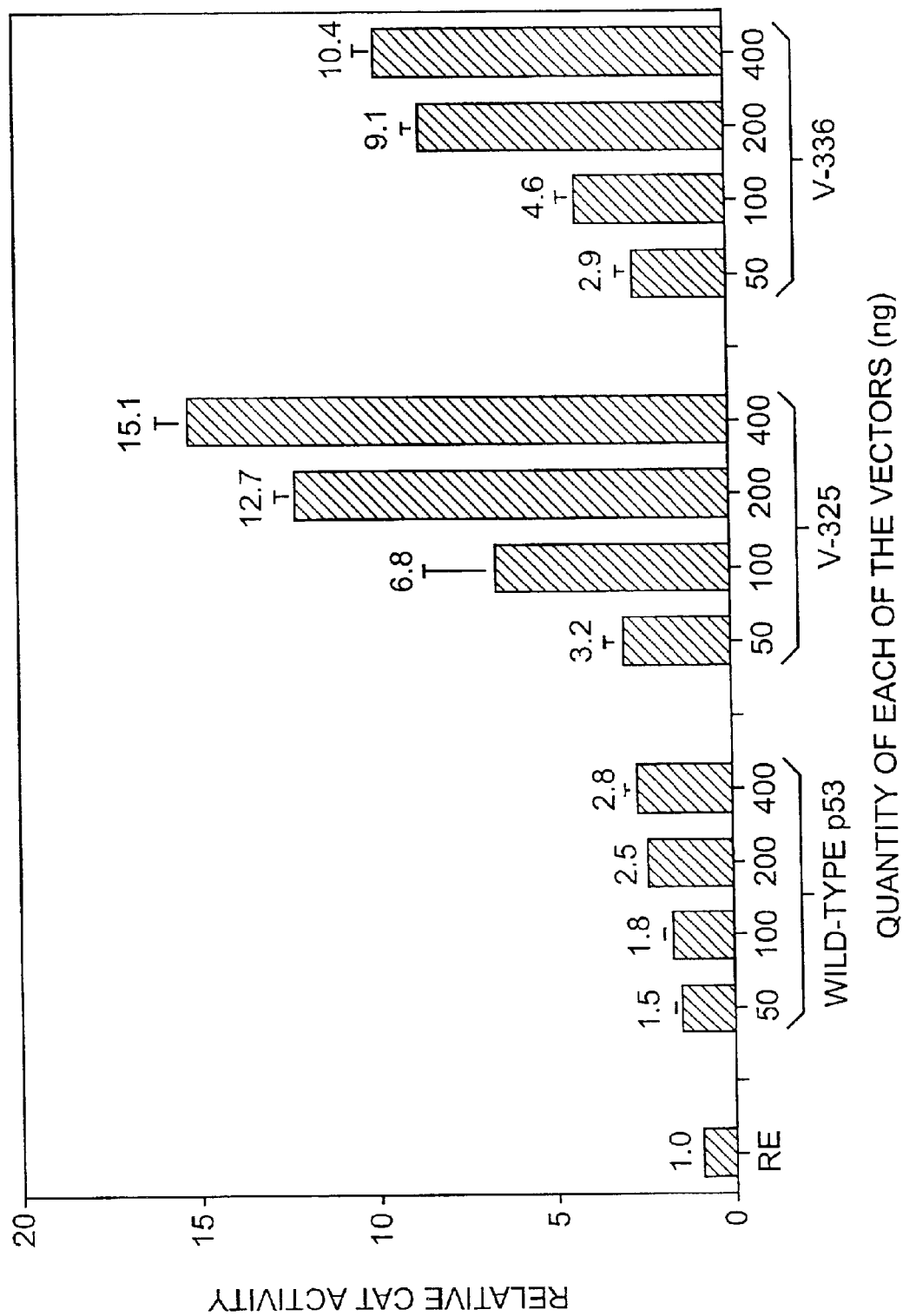

The results presented in FIG. 12 show a very clear transcriptional activity of the two constructs V-325 and V-336, in a context where the wild-type p53 protein is not very active, again suggesting that these two constructs are insensitive to E6 contrary to the wild-type protein.

To test if this absence of sensitivity to the E6 protein is the reflection of a better stability in response to the degradation induced by this protein, an in vitro degradation experiment was carried out.

The various molecules used in this experiment were obtained by translation in vitro, in reticulocyte lysates, of the molecules described in Example C1 (vector pcDNA3) using the TNT Coupled Reticulocyte Lysate Systems kit (Promega) according to the experimental protocol described by the supplier for a total reaction volume of 50 $\mu$l.

For this experiment, the hybrid molecules of the invention, V-325 and V-336 as well as the wild-type p53 protein, are produced by in vitro translation in the presence of 44 $\mu$Ci of $^{35}$S-methionine (Amersham) (1175 Ci/mmol) in order to generate these radioactively labelled hybrid molecules. The E6 protein (HPV18), for its part, is produced under the same conditions but in the absence of $^{35}$S-methionine.

Next, 2 $\mu$l of each of the radiolabelled products (p53, V-325 and V-336) are incubated at 30° C. with 2 $\mu$l of nonradiolabelled E6 protein and 10 $\mu$l of reticulocyte lysate in a final volume of 40 $\mu$l of 25 mM Tris-HCl buffer, pH 7.5, 100 mM NaCl, 3 mM DTT. The reaction is then stopped at various times by removing 7.5 $\mu$l of the reaction medium and adding 7.5 $\mu$l of migration buffer (Laemmli U. K., Nature, 227, 680–685, 1970) and the samples thus prepared are subjected to electrophoresis on a 10% polyacrylamide gel in denaturing medium at 200 V according to the protocol described above (Laemmli U. K., Nature, 227, 680–685, 1970). The gel is then dried and revealed with the aid of an instantimager (Packard instruments) which makes it possible to estimate the quantities of variants of the invention which were not degraded during the reaction.

The result of this experiment, presented in FIG. 13, shows clearly that the V-325 and V-336 variants are much more resistant than the wild-type p53 protein to degradation induced by E6, with again better properties for the V-325 variant in terms of resistance to degradation. These results indeed reflect the differences in sensitivity of the wild-type p53 protein and of the V-325 and V-336 variants to the E6 protein which are observed at the level of the transcriptional activity in the preceding experiments (FIGS. 11 and 12).

This behaviour makes these two constructs super wild-type candidates which are particularly advantageous for the treatment of pathologies linked to infection with HPV16 or HPV18.

D2.3—Effect of a Dominant-negative p53 Mutant on the Transactivating Function

In this experiment, the mutant H175, described as dominant-oncogenic and dominant-negative with respect to the wild-type p53 protein, was used. In this transfection experiment carried out according to the procedure described above, the various constructs as well as the H175 mutant were placed under the control of the CMV promoter (pCDNA3). Each of the constructs was co-transfected with increasing concentrations of the plasmid expressing the mutant H175.

The results presented in FIG. 14 show the following properties for each of the constructs:
- the p53 protein sees its transactivating activity decrease when it is in the presence of an excess of mutated form H175, which indeed corresponds to a physiological situation since it is known that this type of mutant form is much more stable than the wild-type p53 and is therefore always in excess. The dominant-negative effect of this mutant is therefore indeed measured here.
- the AS protein exhibits an increased sensitivity to the dominant-negative effect of the mutant H175, since it is sensitive to lower concentrations of the latter;
- on the contrary, the proteins V-325 and V-336 are not only less sensitive to the dominant-negative effect, but even see their activity increased in a dose-dependent manner in the presence of the mutant form H175. Again, in this test, the protein V-325 exhibits an increased effect compared with the protein V-336, confirming it a little more in its possible status as super wild type.

D2.4—Effect of the hdm2 Protein on the Transactivating Function

Figure 15:
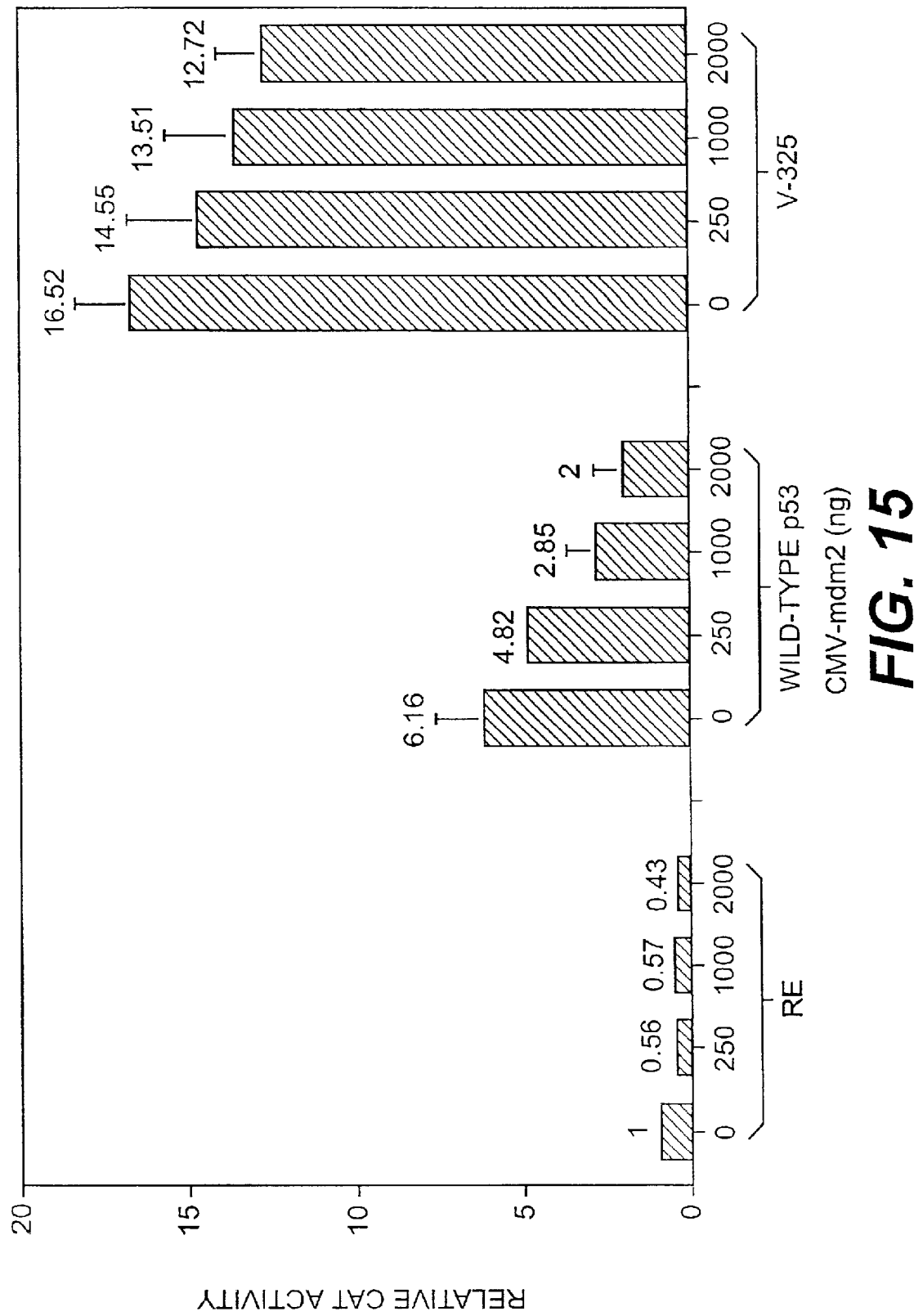

The protocols used are identical to those described in Example D1.1. In this transfection experiment, the constructs placed under the control of the CMV promoter (pcDNA3) are cotransfected with increasing concentrations of a plasmid expressing hdm2 (fragment 1–134) under the control of the CMV promoter (pcDNA3). The results obtained in the SAOS-2 line and presented in FIG. 15 show the following properties for each of the constructs:
- the activity of the p53 protein decreases as the concentration of hdm2 increases, which indeed corresponds to a physiological situation.
- the V-325 protein appears to be insensitive to this inhibition by hdm2.

This behaviour makes the V-325 protein a particularly advantageous superwild-type candidate for the treatment of pathologies linked to an overexpression of hdm2, and more particularly, to the treatment of pathologies linked to the overexpression of cellular proteins which interact with the N-terminal domain of the p53 protein.

The results of these four experiments show clearly that variants according to the invention, especially the variants containing the region 75-325-lz or 75-336-lz, exhibit 1) an increased transactivating activity, 2) a lower sensitivity to the effect of the E6 protein from HPV18, 3) the absence of sensitivity to the dominant-negative effect of some mutants of p53 and even an increase in its activity in such a context, and 4) an absence of sensitivity to the hdm2 protein. These various properties are completely remarkable and unexpected and confer on the variants of the invention considerable therapeutic advantages.

D3—Effect on Cell Growth

The effect of the constructs V-325 and V-336 on cell growth was tested in parallel with p53 on various types of cell lines in an experiment for forming colonies resistant to neomycin following transfection with plasmids expressing these three proteins.

In this transfection experiment carried out according to the procedure described above, the various constructs were placed under the control of the CMV promoter (pCDNA3).

Procedure for formation of colonies resistant to neomycin 48 hours after transfection, the cells are scraped and transferred into Petri dishes 10 cm in diameter and allowed to grow again with 10 ml of DMEM medium supplemented with 10% heat-inactivated foetal calf serum and containing 400 μg/ml of geneticin (G418). Following a selection of 15 days in the presence of G418, the number of Neo$^R$ colonies is determined by counting after staining with fuchsin.

This experiment was carried out on various cell types in which the status of the p53 and Ras proteins is presented in Table 2.

TABLE 2

Status of the cell lines used in the test of formation of Neo$^R$ colonies

| Line | p53 | Ras | hdm2 overexpression | No. ATCC |
|---|---|---|---|---|
| SAOS-2 | –/– | ? | – | HTB 85 |
| HCT 116 | ? | mutated Ki-Ras | – | CCL 247 |
| H 322 | L 248 | ? | – | (*) |
| H 460 | wild-type | mutated Ki-Ras | – | HTB 177 |
| HeLa | wild-type | ? | – | CCL 2 |
| OsA-C1 | ? | ? | + | (**) |

(*) Putnam et al., Surg. Oncol., 1 (1993), 49
(**) Oliner et al., Nature, 358, (1992), 80

Figure 16:
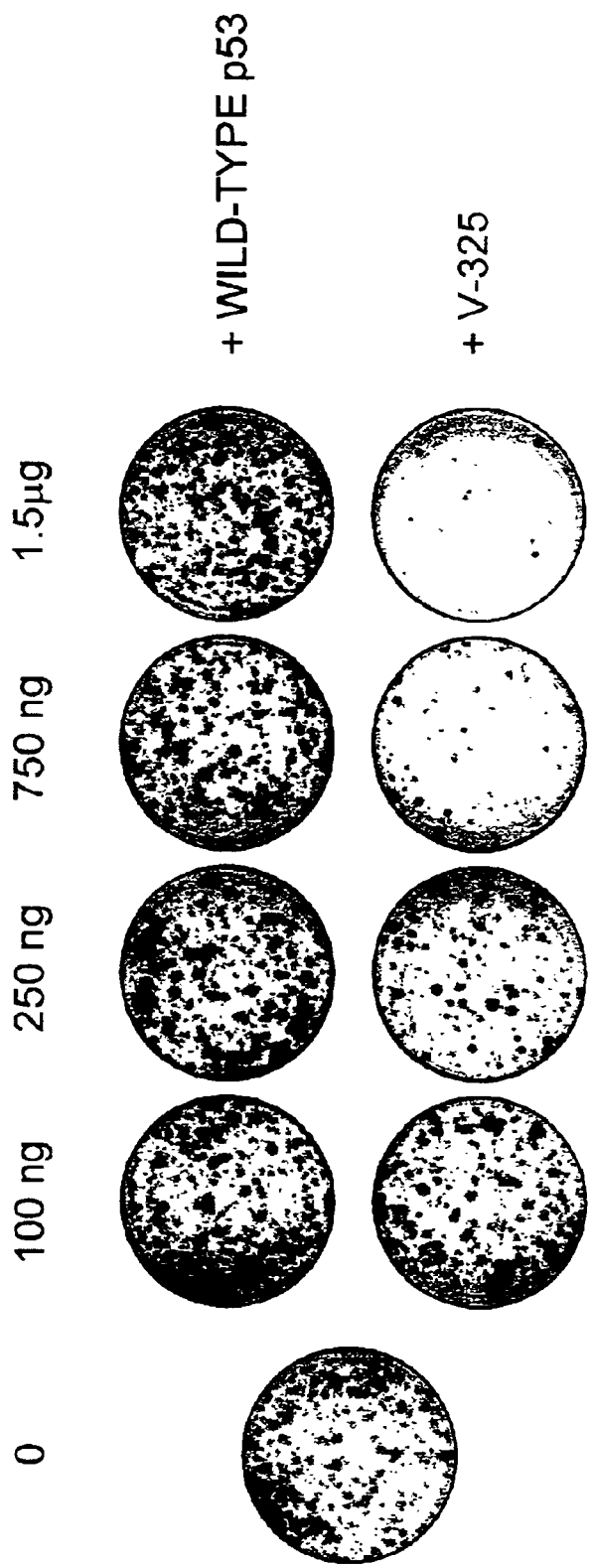

The results of these experiments are presented in Table 3 and in FIG. 16.

TABLE 3

Formation of Neo$^R$ colonies

| Line | Vector | wild-type p53 | V-325 | V-336 |
|---|---|---|---|---|
| SAOS-2 | 253 | 17 | 12 | 13 |
| HCT116 | 112 | 62 | 58 | 61 |
| H 322 | 93 | 5 | 2 | 3 |
| H 460 | 153 | 110 | 87 | 92 |
| HeLa | 172 | 151 | 31 | 47 |

These results show that the constructs V-325 and V-336 possess the capacity to block cell growth in a manner which is at least as effective as the wild-type p53 protein in cellular situations where the latter can function normally (wild-type p53 or double deletant), but especially that they conserve this activity even in cellular situations where the wild-type p53 protein has very little activity (HeLa cells expressing the E6 protein from HPV18 and OsA-CL cells showing overexpression of the hdm2 protein). This property confers on the variants of the invention considerable therapeutic advantages.

D4—Apoptotic Activity of the Variants of the Invention

The apoptotic activity of the variants of the invention was studied using the EB, EB-1 and EB-V325 cells and the induction conditions described above (Example D1).

The cells thus induced ($10^6$ cells) are fixed and permeabilized by a 40-minute incubation in 1 ml of Permeafix (Ortho Diagnostic Systems Inc.), then washed twice in buffer A (PBS (Gibco BRL) supplemented with 0.5% Tween 20), before being resuspended and incubated for one hour at room temperature in 100 µl of buffer A supplemented with 2% BSA (PBS-BSA) and 1 µg of the monoclonal antibody pAb240. After two new washes in PBS-BSA buffer, the cells are incubated for 1 hour at room temperature in 100 µl of the same buffer supplemented with 1 µg of a secondary polyclonal antibody coupled to fluorescein (GAM-FITC (Immunotech)). Next, the cells are washed twice in buffer A, resuspended in 1 ml of the same buffer containing 5 µg of propidimiodide and 1 mg of RNase (DNase-free), and incubated for 30 mn at room temperature before being analysed by flow cytometry.

The result s of a 24- and 48-hour induction experiment, carried out on the EB-1 and EB-V325 cells, are presented in FIG. 17. Under these conditions, the cells expressing the wild-type p53 protein or its variant V-325 (detected by the antibody pAb240) are predominantly distributed in the G1 and sub-G1 phase (apoptosis) after 24 hours of induction, then essentially in sub-G1 after 48 hours. This result clearly indicates that the V-325 protein is capable just like the wild-type p53 protein, of inducing apoptosis.

The results of a kinetic induction experiment carried out on the EB cells and the EB-1 and EB-V325 clones presented in FIG. 18 show that the V-325 variant appears to induce apoptosis more rapidly and more massively than the wild-type p53 protein. Taking A into account the fact that the two proteins appear to be expressed at comparable levels in these clones (cf § D1), this result strengthens the idea of an improved activity of the V-325 variant relative to that of the wild-type p53 protein.

What is claimed is:

1. A nucleic acid encoding a variant of p53 protein wherein
   the C-terminal portion of the protein is deleted from residue 326 or from residue 337 and is replaced by an artificial leucine zipper comprising residues 334–363 of SEQ ID NO: 26; and
   the transactivation domain is deleted and replaced by a VP16 transactivaton domain.

2. The nucleic acid according to claim 1, which is a DNA or an RNA.

3. The nucleic acid according to claim 1, wherein said nucleic acid comprises p53 wildtype domains as well as synthetically produced sequences.

4. The nucleic acid according to claim 1, wherein the variant encoded is SEQ ID NO: 26.

5. The expression cassette comprising the nucleic acid according to claim 1, a promoter allowing expression of said nucleic acid, and a transcription termination signal.

6. A vector comprising the nucleic acid according to claim 1.

7. The vector according to claim 6, which is a viral vector.

8. The vector according to claim 7, wherein the vector is a recombinant defective adenoviral vector, recombinant defective retrovirus vector, recombinant defective adeno-associated virus vector (AAV), or recombinant defective herpes simplex virus vector (HSV).

9. The vector according to claim 6, which is a chemical vector.

10. A composition comprising the nucleic acid according to claim 1 and a pharmaceutically-acceptable carrier.

11. A composition comprising the vector according to claim 6 and a pharmaceutically-acceptable carrier.

12. The composition according to claim 10, wherein the nucleic acid has the sequence of SEQ ID NO; 25.

* * * * *